(12) United States Patent
Ben-Oren et al.

(10) Patent No.: US 6,656,127 B1
(45) Date of Patent: Dec. 2, 2003

(54) BREATH TEST APPARATUS AND METHODS

(75) Inventors: Ilan Ben-Oren, Jerusalem (IL); Ephraim Carlebach, Raanana (IL); Julian Daich, Jerusalem (IL); Lewis Colman, Jerusalem (IL); Gershon Levitsky, Jerusalem (IL); Boaz Givron, Jerusalem (IL); Daniel Katzman, Brookline, MA (US)

(73) Assignee: Oridion Breathid Ltd., Jerusalem (IL)

( * ) Notice: Subject to any disclaimer, the term of this patent is extended or adjusted under 35 U.S.C. 154(b) by 0 days.

(21) Appl. No.: 09/542,768

(22) Filed: Apr. 4, 2000

(30) Foreign Application Priority Data

Aug. 6, 1999 (IL) ................................. 130370
Aug. 6, 1999 (IL) ................................. 130372

(51) Int. Cl.$^7$ ................................. A61B 5/08
(52) U.S. Cl. ........................... 600/532; 600/529
(58) Field of Search ................ 600/529, 531, 600/532, 533, 538, 543; 73/23.3; 128/920, 923, 924, 925

(56) References Cited

U.S. PATENT DOCUMENTS

| | | | |
|---|---|---|---|
| 4,390,483 A | 6/1983 | Willems et al. | |
| 4,448,058 A | 5/1984 | Jaffe et al. | |
| 4,490,482 A | 12/1984 | Mathieu | |
| 4,639,432 A | 1/1987 | Holt et al. | |
| 4,680,956 A | 7/1987 | Huszczuk | |
| 4,684,805 A | 8/1987 | Lee et al. | |

(List continued on next page.)

FOREIGN PATENT DOCUMENTS

| | | |
|---|---|---|
| DE | 19714903 | 10/1998 |
| DE | 19735599 | 3/1999 |
| EP | 0 253 927 | 1/1988 |
| EP | 0 415 600 | 3/1991 |
| EP | 0 512 535 | 11/1992 |
| EP | 0 908 187 | 4/1999 |
| EP | 0 860 170 | 3/2000 |
| GB | 1 591 709 | 6/1981 |
| JP | 05 010955 | 5/1993 |
| WO | WO 96/14091 | 5/1996 |
| WO | WO 98/21579 | 5/1998 |
| WO | WO 98/30888 | 7/1998 |
| WO | WO 99/12471 | 3/1999 |
| WO | WO 99/14576 | 3/1999 |

OTHER PUBLICATIONS

Israeli, E. et al., "Continuous, Real Time Measurement with a Novel 13C–Breath Analyzer: Faster Urea Breath Test Results with High Accuracy", *Gastroenterology*, vol. 116(4), Apr. 1999, p. A–195.

(List continued on next page.)

*Primary Examiner*—Max F. Hindenburg
*Assistant Examiner*—Navin Natnithithadha
(74) *Attorney, Agent, or Firm*—Morgan & Finnegan LLP

(57) ABSTRACT

Breath test methods and apparatus for increasing accuracy and reducing the time taken to achieve diagnostically useful results. In order to determine when an increase in isotopic ratio of the exhaled breath is clinically significant, methods are described for the use of a variable and multiple threshold level; for reducing the time taken to determine an accurate baseline level; and for avoiding the effects of oral activity when making measurements. To increase measurement accuracy, methods are described, using the results of the breath tests themselves, of continuous and automatic self-calibration to correct for drifts in the gas spectrometer absorption curves. A method for increasing the spectral stability of cold cathode discharge infra-red light sources for use in breath test instrumentation is described. Calibration checking devices and methods of mandating their use at regular time intervals are described, to ensure maintenance of the accuracy of breath tests.

47 Claims, 26 Drawing Sheets

U.S. PATENT DOCUMENTS

| | | | |
|---|---|---|---|
| 4,723,435 | A | 2/1988 | Huszczuk |
| 4,756,000 | A | 7/1988 | Macken |
| 4,757,512 | A | 7/1988 | Macken |
| RE33,493 | E | 12/1990 | Lee et al. |
| 5,146,294 | A | 9/1992 | Grisar et al. |
| 5,300,859 | A | 4/1994 | Yatsiv et al. |
| 5,317,156 | A | 5/1994 | Cooper et al. |
| 5,394,236 | A | 2/1995 | Murnick |
| 5,479,019 | A | 12/1995 | Gross |
| 5,486,699 | A | 1/1996 | Fabinski et al. |
| 5,501,231 | A * | 3/1996 | Kaish ..................... 600/538 |
| 5,543,621 | A | 8/1996 | Sauke et al. |
| 5,640,014 | A | 6/1997 | Sauke et al. |
| 5,657,750 | A | 8/1997 | Colman et al. |
| 5,747,809 | A | 5/1998 | Eckstrom |
| 5,787,885 | A | 8/1998 | Lemelson |
| 5,818,580 | A | 10/1998 | Murnick |
| 5,908,789 | A | 6/1999 | Weckstrom |
| 5,944,670 | A | 8/1999 | Katzman |
| 5,957,858 | A | 9/1999 | Micheels et al. |
| 5,961,470 | A | 10/1999 | Wagner et al. |
| 5,962,335 | A | 10/1999 | Katzman |
| 5,964,712 | A | 10/1999 | Kubo et al. |
| 6,067,989 | A | 5/2000 | Katzman |
| 6,096,558 | A | 8/2000 | Stock |
| 6,106,479 | A | 8/2000 | Wunderlich et al. |
| 6,186,958 | B1 * | 2/2001 | Katzman et al. ........... 600/532 |

OTHER PUBLICATIONS

NASA, "Low–Temperature Oxidation Catalysts", Oct. 1995, pp. 1–2 http://tag–www.larc.nasa.gov/tops.

Schoeller, et al., "$^{13}$C Abundances of Nutrients and the Effect of Variations in $^{13}$C Isotopic Abundances of Test Meals Formulated for $^{13}CO_2$ Breath Test $^{1-3}$", *American Journal of Clinical Nutriton*, chap. 33, Nov. 1980, pp. 2375–2385.

"The ABC–NT Gas Isotope Ratio Mass Spectrometer", 510(k) Summary, K974322, Nov. 1997, pp. 1–9.

Kalach, et al., "The $^{13}$Carbon Urea Breath Test for the Noninvasive Detection of Helicobacter Pylori in Children: Comparison with Culture and Determination of Minimum Analysis Requirements", *Journal of Pediatric Gastroenterology and Nutrition*, vol. 26, Mar. 1998, pp. 291–296.

STC Catalysts, Inc., "Catalysts for Long–Life $CO_2$ Lasers", Nov. 1996, pp. 1–4, http://www.stenet.com.

U.S. patent application Ser. No. 089/961,013, entitled FLUID ANALYZER WITH TUBE CONNECTOR VERIFIED, filed Oct. 30, 1997.

Graham, D.Y. et al., "Citric Acid as the Test Meal for the $^{13}$C–Urea Breath Test", *American Journal of Gastroenterology*, vol. 94, May 1999, pp. 1214–1217.

Alimeterics, "Pylori–Chek Breath Test Kit", 08–0190 Rev OC, USA, 1999, pp. 1–18.

Oridion Medical Ltd., "BreathID Profile", pp. 1–8, Feb. 1999, Israel.

Haisch, "Quantitative Isotope–Selective Infra–Red Spectroscopy for Determining the Isotopic Ratio of Carbon Dioxide in Breath", Haisch Inaugural Dissertation, Heinrich Heine Universitaet, Duesseldorf, 1995, pp. 1–10.

U.S. patent application Ser. No. 08/961,013 entitled "FLUID ANALYZER WITH TUBE CONNECTOR VERIFIER".

* cited by examiner

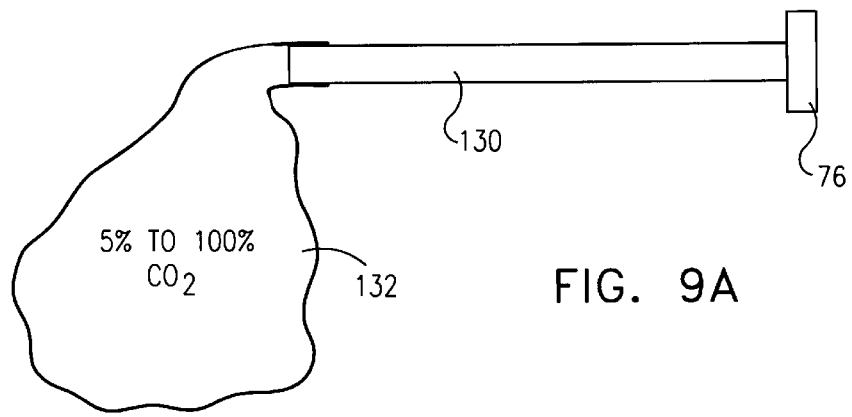
FIG. 9A
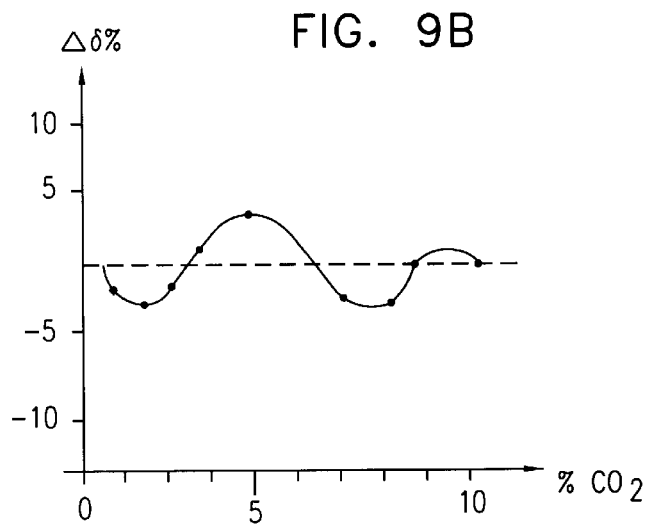
FIG. 9B
FIG. 10
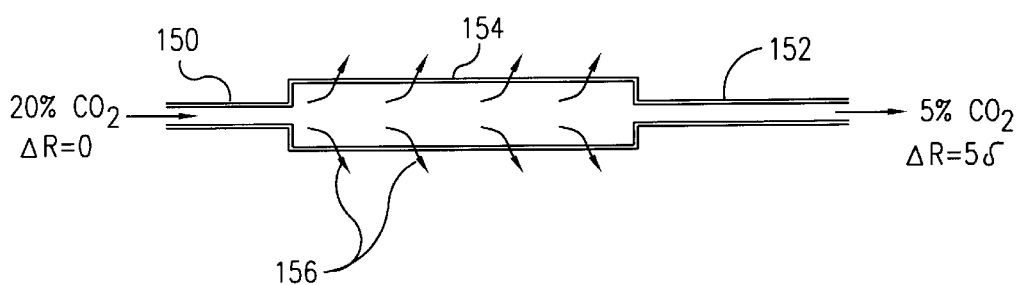

$$\Delta(^{12}CO_2) = (^{12}CO_2)_{in} - (^{12}CO_2)_{out}$$
$$(^{12}CO_2)_{out} = 5\% = \text{constant}$$
$$Q = 250\text{ml/min} = \text{constant}$$

BREATH TEST APPARATUS AND METHODS

FIELD OF THE INVENTION

The present invention relates to the field of breath test instrumentation and methods of use, especially in relation to their accuracy, reliability and speed.

BACKGROUND OF THE INVENTION

Gas analyzers are used for many measurement and monitoring functions in science, industry and medicine. In particular, gas spectrometry is becoming widely used in diagnostic instrumentation based on the use of breath tests for detecting a number of medical conditions present in patients. Descriptions of much breath test methodology and instrumentation are disclosed in PCT Publication No. WO99/12471, entitled "Breath Test Analyzer" by D. Katzman and E. Carlebach, some of the inventors in the present application. Methods of constructing and operating gas analyzers such as are used in breath test instrumentation are disclosed in PCT Publication No. WO99/14576, entitled "Isotopic Gas Analyzer" by I. Ben-Oren, L. Coleman, E. Carlebach, B. Giron and G. Levitsky, some of the inventors in the present application. Applications of some breath tests for detecting specific medical conditions are contained in patents issued to one of the inventors of the present application, namely U.S. Pat. No. 5,962,335 to D. Katzman on "Breath Test for Detection of Drug Metabolism", and U.S. Pat. No. 5,944,670 to D. Katzman on "Breath test for the Detection of Bacterial Infection", and in allowed U.S. patent application Ser. No. 08/805415 now U.S. Pat. No. 6,067,989, by D. Katzman on "Breath test for the Diagnosis of Helicobacter Pylori Infection in the Gastrointestinal Tract". Each of the above documents is hereby incorporated by reference in its entirety.

Such breath tests are based on the ingestion of a marker substrate, which is cleaved by the specific bacteria or enzymic action being sought, or as a result of the metabolic function being tested, to produce marked by-products. These by-products are absorbed in the blood stream, and are exhaled in the patient's breath, where they are detected by means of the gas analyzer.

One well known method of marking such substrates is by substituting one of its component atoms with an isotopically enriched atom. Such substrates and their by-products are commonly called isotopically labeled. One atom commonly used in such test procedures is the non-radioactive carbon-13 atom, present in a ratio of about 1.1% of naturally occurring carbon. Using $^{13}C$ as the tracer, the cleavage product produced in many such tests is $^{13}CO_2$, which is absorbed in the bloodstream and exhaled in the patient's breath. The breath sample is analyzed, before and after taking this marker substrate, typically in a mass spectrometer or a non-dispersive infra-red spectrometer. Detected changes in the ratio of $^{13}CO_2$ to $^{12}CO_2$ may be used to provide information about the presence of the specific bacteria or enzymic action being sought, or as a measure of the metabolic function being tested.

Since the amount of $CO_2$ arising from the process under test may be a very small proportion of the total $CO_2$ production from all of the bodies' metabolic processes, the breath test instrumentation must be capable of detecting very small changes in the naturally occurring percentage of $^{13}CO_2$ in the patient's breath. Typically, the instrument should be capable of detecting changes of a few parts per million in the level of $^{13}CO_2$ in the patient's exhaled breath, where the whole $^{13}CO_2$ content in the patient's exhaled breath is only of the order of a few hundred ppm. For this reason, the sensitivity, selectivity and stability of the gas analyzers used in such tests must be of the highest possible level to enable accurate and speedy results to be obtained.

Furthermore, since the instrument is intended to operate in a point-of-care environment, where there is generally no continuous technician presence, the instrument must have good self-diagnostic capabilities, to define whether it is in good operating condition and fit for use. For similar reasons, it should also have a level of self calibration capability, to correct any drift in calibration level revealed in such self-diagnostic tests or otherwise.

The use of the instrument in a point-of-care environment adds additional importance to the speed with which an accurate diagnosis can be given to the patient following the test. Consequently, to increase patient compliance, the methods used in the breath test for analyzing the results of the measurements in terms of meaningful diagnostic information should be designed to provide as conclusive and reliable a result in as short a time as possible. Furthermore, the execution of the test in the physician's office is greatly facilitated by the use of simple patient and substrate preparation procedures.

In order to maintain the reliability of such tests, it is necessary to ensure that the calibration of the gas analyzer is maintained at the correct level. For this reason, in order to ensure maintenance of the high accuracy levels required, many of the prior art instruments necessitate the performance of complex and time-consuming calibration procedures, some of which have to be laboratory performed, rather than user-performed in the field. Since the advent of compact and low cost breath test instrumentation is making breath testing a widely used medical office procedure, instead of a hospital or laboratory procedure, the need for simple, user-performed, periodic calibration checks is becoming of prime importance.

Furthermore, the breath exhaled by patients always contains a naturally high level of humidity, and in the case of intubated patients, could also contain a high level of moisture and other secretions. The presence of such extraneous fluids can severely affect the ability of the gas analyzer to accurately measure the sought-after gas. Furthermore, constant exposure to high levels of humidity can have an adverse effect on the component parts of the gas analyzer, and especially on the measuring sensor itself. For these reasons, moisture and humidity filters are advisable to maintain the accuracy of the instrument. Since the operator may have a tendency to use the filters provided with the instrument beyond the recommended number of times, thereby impairing the accuracy of the measurement, it is important that means be adopted to ensure that the filtration unit is not used beyond its stated lifetime.

There therefore exists a need to ensure the maintenance of the accuracy of breath test instrumentation, both by means of regular mandated calibration checks, and by ensuring regular mandated changes of the moisture filter used with the instrument. Furthermore, there is a need for the calibration check procedure to be capable of simple and preferably semi-automatic execution by the user, rather than requiring the intervention of a technician, or shipment to a calibration laboratory.

The unique characteristics of the breath test analyzer described in the above mentioned PCT Publication No. WO 99/12471, are due in large measure to the use of electrodeless cold gas discharge infra-red lamp sources, as described in U.S. Pat. No. 5,300,859, entitled "IR-Radiation Source and Method for Producing Same" to S. Yatsiv et al., hereby incorporated by reference in its entirety. One of the important advantages of such lamp sources is that they emit very narrow spectral lines at discrete frequencies characteristic of the molecular rotational-vibrational to ground state transitions of the excited gas species contained in the lamp. This is achieved in a source which is sealed-off, is compact, has a good level of conversion efficiency from electrical to optical power, and has a long life compared with previously available sealed-off lamps sources.

The unique spectral properties and the narrowness of the emission lines of such lamps provides such gas analyzers with high levels of selectivity, sensitivity and stability, which are many times better than gas analyzers of similar complexity, which use lamp sources of alternative technologies, such as hot blackbody sources. The other advantages mentioned above enable the production of compact and cost effective instrumentation using such sources.

The lamp sources described in U.S. Pat. No. 5,300,859 have found particularly advantageous applications as sources of the $CO_2$ spectral emission lines, for gas analysis of exhaled breath, to determine the levels of $CO_2$ therein. Such $CO_2$ sources have been used to great advantage in capnography and breath testing instrumentation.

In U.S. Pat. No. 5,300,859, there is a thorough discussion regarding the parameters affecting the lamp emission rise and decay time, efficiency, excitation and output, and the lamp lifetime as a function of chemical methods used to clean the lamp before sealing. On the other hand, the question of the spectral stability of the lamp source is not addressed. However, when used as a frequency selective source in NDIR spectroscopic applications, spectral stability may even be more important than the above parameters. Intensity changes over time can easily be monitored and corrected by using a reference path, since lamp intensity is a single valued quantity. On the other hand, spectral changes can not be easily monitored or corrected for, because of the huge amount of information contained in a spectrum. Changes in the lamp spectrum cause changes in the absorption cell absorption characteristics. If these changes are not known, then it is impossible to accurately measure gas concentrations using such lamp sources. There therefore exists a serious need for a method of maintaining a high level of spectral stability in electrode-less cold gas discharge infra-red lamp sources. A high level of spectral stability would make an important contribution to the maintenance of accurate calibration levels in breath test instruments using such lamps.

The disclosures of all publications mentioned in this section and in the other sections of the specification, are hereby incorporated by reference, each in its entirety.

SUMMARY OF THE INVENTION

The present invention seeks to provide new methods and devices for ensuring the accuracy, speed and reliability of breath tests. A number of separate aspects of the invention are disclosed herein, including but not limited to subjects related to:

(i) system checking devices and methods of ensuring their periodic use;
(ii) methods of patient preparation and substrate ingestion;
(iii) methods of analysis of the results of breath tests to provide accurate diagnoses in the minimum possible time;
(iv) self-diagnostic facilities and calibration of breath test instruments; and
(v) the spectral stability for electrode-less cold gas discharge infra-red lamps, such as those used in NDIR gas spectrometers typically used in breath testers.

The term "system check" is generally used throughout this specification and claimed, to describe methods for determining that multiple aspects of the measurement system are functioning correctly, including primarily calibration of the gas analyzer, but also possibly including such functions as the radiation source stability, the input capnograph calibration, the gas handling system, the intermediate chamber system for collecting and diluting accumulated breath samples, and the detector operation.

The term "calibration check" is generally used in this specification and claimed, to refer to a measurement of the absolute calibration of the isotopic ratios measured by the breath tester, referred to a zero base line level, by the use of calibration checking gases with known isotopic concentrations or ratios, input to the instrument from externally supplied containers. Since a calibration check is part of a system check, overlapping use of these terms may have been made on occasion, according to the context under discussion.

The use of the term "calibration" of the instrument, on the other hand, is generally used in this specification and claimed, to describe a process whereby the parameters of the absorption curves used for the infra-red absorption measurements of the gases are corrected so that they compensate for drift or other environmentally induced changes occurring in the instrument. Changes in the absorption curves are indeed generally the major cause for changes in the calibration of the instrument. According to this nomenclature, a calibration procedure, as opposed to a calibration checking procedure, does not use externally supplied gases with known isotopic concentrations or ratios, but typically relies on checks for internal inconsistency in the results obtained in actual measurements performed by the breath tester. The usual inconsistency revealed is an unjustified correlation of measured values of isotopic ratio with gas concentration, as will be further expounded hereinunder.

The present invention first of all seeks to provide a new system checking device for use with gas analyzer-based breath test instrumentation, including the ability to perform a calibration check of the instrument against known calibrating gases. The use of the device with breath tests is particularly important, because of the high sensitivity, selectivity and accuracy, which must be maintained to ensure the success of such tests. The use of the device is simple, and ensures that the overall functionality and accuracy of the gas analyzer is checked at regular predetermined periods, without the need for the operator to perform complex calibration procedures. At the same time, the calibration checking device may also comprise a fluid filter, and is so constructed that its use ensures efficient fluid filtering.

There is thus provided in accordance with a preferred embodiment of the present invention, a calibration checking sampling line unit with a built-in filter, particularly for use with breath test instrumentation. In order to maintain the guaranteed accuracy of the breath test, it is important both to perform regular calibration checks of the gas monitor, and to ensure that the humidity level of the sampled gas is kept below a specified level, and that there is no liquid penetration into the gas analyzer. Each calibration check device is designed to be used for a predetermined number of tests, with a separate disposable oral/nasal part for each individual test performed. After first connection of a new calibration check device, according to one preferred embodiment of the present invention, a volume of known calibration checking gas is released into the instrument, and a calibration checking measurement is initiated. At the same time, a signal is sent to a counting mechanism which both enables the use of the instrument, and commences a count of the number of tests performed by the breath tester. The counting mechanism can be located either on the calibration checking device or in the instrument itself. When the predetermined number of tests have been performed, after which a new calibration check is recommended, the counting mechanism provides operator warning thereof, or preferably even prevents continued operation of the instrument until a new calibration check is performed. A preferred method for performing this control function is disclosed in a further embodiment of the present invention.

According to another preferred embodiment of the present invention, the signal transmitted after first connection of a new calibration check device and performance of a calibration check procedure, is sent to a timing mechanism which both enables the use of the instrument, and begins accumulating the amount of time that the breath tester has been in operation since the last calibration checking procedure. When a predetermined operation time has been exceeded, after which a new calibration check is recommended, the timer mechanism provides operator warning thereof, or preferably even prevents continued operation of the instrument until a new calibration check is performed.

According to a further preferred embodiment of the present invention, the built-in moisture filter also has an interface with the instrument, which prevents its operation if the filter is used beyond the recommended number of times, or if excess moisture renders it saturated. As an alternative to a multiple-use filter unit, the disposable oral/nasal part supplied for each individual test could be provided with a built-in section of moisture filtering or moisture absorbing material, to ensure the use a fresh filter element for every patient test. According to this embodiment of the invention, the use of a fresh filter, while not mandated, should be performed automatically if normal hygienic clinical procedures of using a new cannula for every test are followed. In this case, to give additional assurance that a new cannula would be used for every test, each calibration check unit is preferably supplied as a kit with the number of disposable oral/nasal parts, which would suffice for the number of tests expected to be performed within the recommended changing period of the calibration check unit.

In accordance with further preferred embodiments of the present invention, where the particular circumstances of the test conditions allow it, the calibration check device can incorporate a calibration check unit only, without a filter device, or a filter device only, without any calibration check unit. Alternatively and preferably, the calibration check device can contain both a calibration check unit and a filter unit, and the enable or count signal transmitted to the instrument from only one or other of the two units.

According to further preferred embodiments of this aspect of the present invention, the calibration checking device is used in co-operation with a breath simulating device inside the breath tester, the combination operating as a complete system checking device. From the calibration checking device gas fill, a series of gas samples is produced which simulate all aspects of the breath of a subject undergoing a breath test. According to these embodiments, the breath simulator provides samples of (i) ambient air with the natural level of the breath test gas, to simulate the inhaled breath, (ii) a sample of the gas to be detected in the breath test with a known low isotopic ratio, to simulate the exhaled breath of a subject before ingestion of the isotopically labeled substrate, and (iii) a sample of the breath test gas having an isotopic ratio of the detected component somewhat increased, to simulate the exhaled breath of a subject having a detectable response to the breath test. The timing of the supply of these three types of calibration check input gases is preferentially provided by means of a pneumatic system using solenoid valves to route the gases through the correct paths, and at the correct timing rate to simulate human respiration rate. According to alternative preferred embodiments, the calibration checking gas with the slightly raised isotopic ratio component is generated either by means of a porous tube device, able to preferentially change the isotopic content of a gas flowing through it, or by means of two separate calibration checking gas containers, each containing a gas fill with a slightly different isotopic ratio.

According to a second aspect of the present invention, there is provided in accordance with further preferred embodiments of the present invention, methods relating to the patient preparation before administration of the breath test. These methods are made possible only because of the method of virtually continuous sampling and analyzing of breaths, as described in this application, and in the documents described in the background section. In addition, methods of preparation and administration of the substrate for ingestion before the breath test are described.

It is to be understood that, throughout this specification and as claimed, the use of terms to describe sampling and/or analyzing, such as "virtually continuous sampling" or "virtually continuous analyzing" or equivalent descriptive expressions, such as "substantially continuously", are meant to refer to methods of sampling or analyzing capable of being performed repeatedly and repetitively at a rate which is sufficiently high that a number of samplings and/or analyses are performed within the time taken for useful clinical information to be determined from the physiological effects under investigation by the breath test. This rate is thus highly dependent on the type of breath test involved. In the case of a breath test such as that for the detection of *Helicobacter pylori,* for instance, where a meaningful clinical result may already be obtained in a matter of a few minutes, "virtually continuous sampling" could be taken to mean a rate as fast as almost every exhaled breath of the subject. On the other hand, with breath tests such as that for liver function, in which it could be several hours before a meaningful result is obtained, the condition of "virtually continuous sampling" or equivalent terms, may be fulfilled by means of a breath sample collection and/or analysis every half hour, for instance.

It is this feature of virtually continuous sampling or analysis which provides the present invention with many of its advantages over prior art methods of sampling and analyzing individual bags of breath. From a practical point of view, it is difficult, if not well-nigh impossible, to perform such prior art methods "virtually continuously", and it is this feature which thereby enables the present invention to provide clinically significant results both earlier and with a higher level of reliability than by prior art methods.

According to a third aspect of the present invention, there are also provided in accordance with more preferred embodiments of the present invention, methods for analysis of the results of breath tests to provide accurate diagnoses within times significantly shorter than those possible by use of prior art methods. These methods include the use of a method for detecting the presence of oral activity in the subject, arising from the direct interaction of the labeled substrate with bacteria in the oral cavity, unrelated to the physiological state being tested for. It is important to detect such oral activity, and to delay the analysis of the collected breaths until after its subsidence. Otherwise the breath test's ability to detect by-products of the labeled substrate exhaled in the subject's breath after traversing a metabolic path through the subject's blood stream and lungs, would be severely degraded.

Further novel methods are disclosed for calculating the change in isotopic ratio over the baseline isotopic ratio, which enable more reliable test results to be obtained in situations where there may be interference or excessive noise in the measurement. A further method is described for combating the effects of drift in the breath test instrumentation, which may limit the ability to accurately compare currently collected samples with a baseline sample collected earlier. According to this preferred embodiment of the present invention, the sample collected at each sampling point is compared with the sample collected at the previous sampling point, rather than with a baseline sample or an external reference gas.

Further preferred embodiments are disclosed in which the changes in isotopic ratio detected are analyzed using a newly proposed parameter, called the Relative Change in Isotopic Ratio, or RCIR, which compares the fractional change in the currently obtained ratio, normalized to a variety of isotopic ratios, each of which has its own specific advantages. A method is also disclosed of using alternating definitions for the RCIR parameter, according to the progress of the test results, in order to reduce the effects of physiological or instrumental noise in the test results. A method for more accurate detection of the baseline level is also disclosed, whereby multiple baseline measurements are made to eliminate the possible negative effects of a single rogue measurement point.

The operational function in a breath test is to determine when a change in the isotopic ratio of a component of breath samples of the subject is clinically significant with respect to the effect being sought. The criterion for this determination, as used in much of the prior art, is whether or not the isotopic ratio has exceeded a predefined threshold level, at, or within the allotted time for the test. According to another preferred embodiment of the present invention, in order to achieve the highest sensitivity and specificity in the shortest possible measurement time, the breath test analyzer does not use fixed criteria for determining whether the change in the isotopic ratio of a patient's breath is clinically significant. Instead, the criterion is varied during the course of the test, according to a number of factors manifested during the test, including, for instance, the elapsed time of the test, the noise level of the instrument performing the test, and the physiological results of the test itself.

Furthermore, although in many of the prior art procedures, the measurement used for the change in the isotopic ratio has been the level of the ratio over a baseline level, according to further preferred embodiments of the present invention, the measurement could be the change over a previous measurement point other than a baseline level, or the rate of change of the isotopic level, or any other suitable property which can be used to plot the course of the change.

As an example of the execution of such a variable criterion, the crossing of a threshold level by the isotopic ratio is used to illustrate the advantages of these preferred embodiments of the present invention. A calculation method is disclosed for the more accurate use of the threshold level, above which, according to the methods of the prior art, a test result is assumed to be positive, or below which it is assumed to be negative. The method makes use of a dynamically variable threshold, whose value changes according to the progress of the breath test. It is optionally and preferably made dependent on the elapsed time of the test, on the physiological meaning of the results, on the scatter or quality of the results themselves, and on the noise level or drift of the instrument being used. In addition, further preferred embodiments using multiple thresholds are disclosed.

According to a fourth aspect of the present invention, there are also provided, in accordance with other preferred embodiments of the present invention, methods for self-diagnostic analysis of a breath test instrument, and for system checking of the instrument. According to these preferred embodiments, novel methods are disclosed for calibration of the instrument according to the data being collected, either automatically, or by means of operator intervention. Such methods generally are based on the assumption that if the absorption curve of the gas analyzer is accurately known, then the isotopic ratio measured in the gas being detected, according to the supposedly correct absorption curve, will show no dependence on changes in the concentration of the sample being measured. Any such dependence found is reduced by means of an iterative correction method, which changes the parameters of the absorption curve in such a manner as to reduce any such correlation.

Another preferred method disclosed according to this aspect of the present invention is operative for correcting any inaccuracy in the capnographic measurement performed at the entrance to a breath tester, by means of comparison with an accurate measurement performed by the self-calibrating gas analyzer, as summarized above. The capnographic measurement is used in order to determine which parts of the breath waveform are collected for analysis by the gas analyzer in the breath tester.

According to a fifth aspect of the present invention, there is provided, in accordance with another preferred embodiment of the present invention, a new method of producing cold gas discharge infra-red lamp sources with improved spectral stability, especially for those lamps operating with a carbon dioxide fill. A catalyst is used to induce recombination of the dissociation products of molecules of the fill gas broken down by the action of the electrical discharge, and the resulting maintenance of the level of self absorption of the lamp emission, results in a concomitant maintenance of the spectral shape of the lamp emission. As a result of this maintained spectral purity, a breath tester utilizing such a lamp has improved resolution and improved accuracy, resulting from the more accurate and better resolved absorption measurement made on the isotopic gas mixture.

BRIEF DESCRIPTION OF THE DRAWINGS

The present invention will be understood and appreciated more fully from the following detailed description, taken in conjunction with the drawings in which:

FIG. 4A shows a connector incorporating a simple electrical contact interface and FIG. 4B shows a connector with an optical interface.

FIGS. 9A and 9B illustrate schematically the operational concepts which are the basis of the calibration checking methods according to preferred embodiments of the present invention. FIG. 9A shows a representation of a source of a calibrating gas of known concentrations, which can come from a variety of sources, while FIG. 9B shows a schematic graph of results typically obtained from a series of dilutions of the calibrating gas, and measurements of the isotopic ratio at each dilution;

FIG. 10 schematically shows a preferred embodiment of a porous tube for generating a gas sample with a different isotopic ratio to that input to the tube;

FIG. 18A shows the closed container, while FIG. 18B shows the calibration checking gas released by the act of screwing the container into the front panel connector of the breath tester. FIG. 18C shows a device for ensuring that the gas container is correctly located in the front panel input connector, when use is made of an alternative embodiment whereby the container is inserted by means of linear motion;

DETAILED DESCRIPTION OF PREFERRED EMBODIMENTS

Overall Breath Test System Construction and Operation

Figure 1:
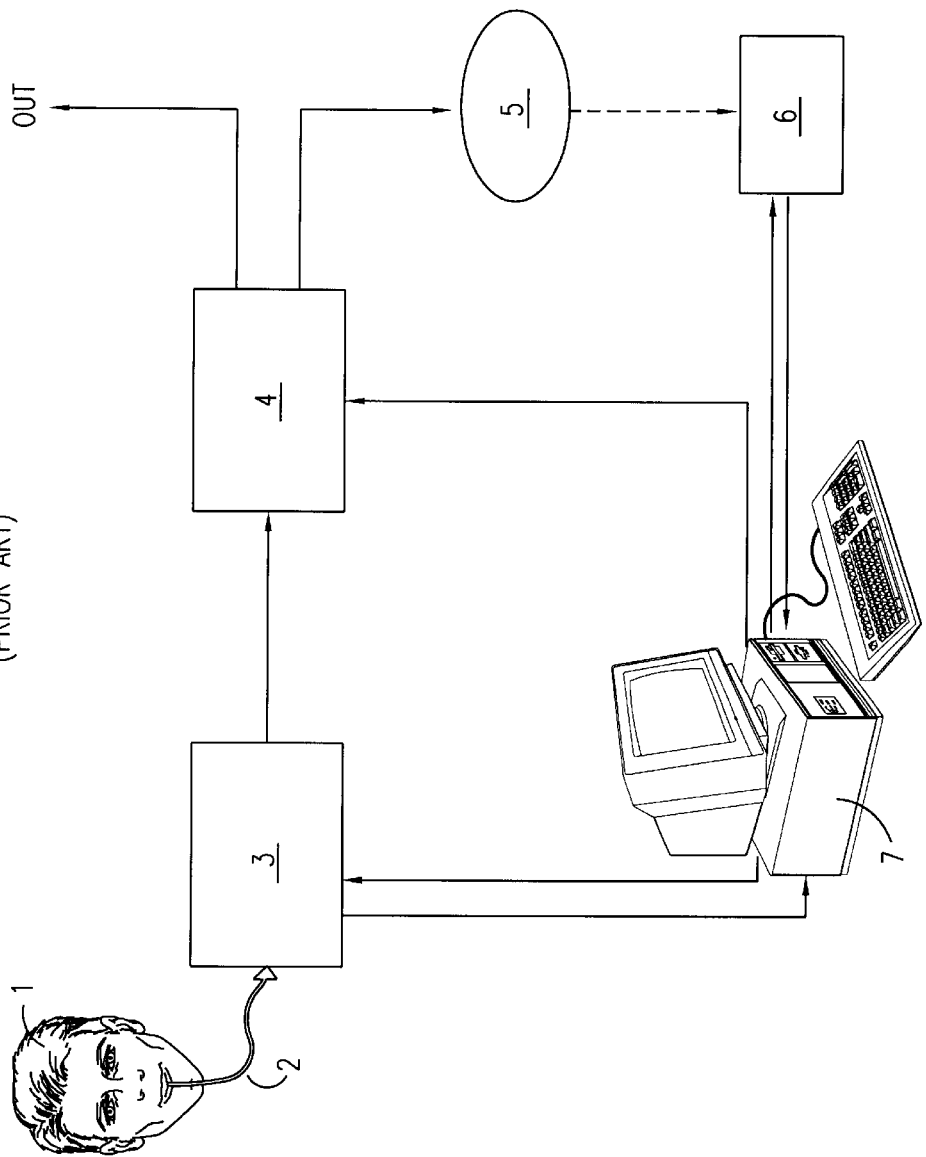
FIG. 1 is a schematic block diagram of the constituent parts of a breath tester as disclosed in PCT Publication No. WO99/14576, incorporating an intermediate chamber system for accumulating and manipulating breath samples.
Figure 2:
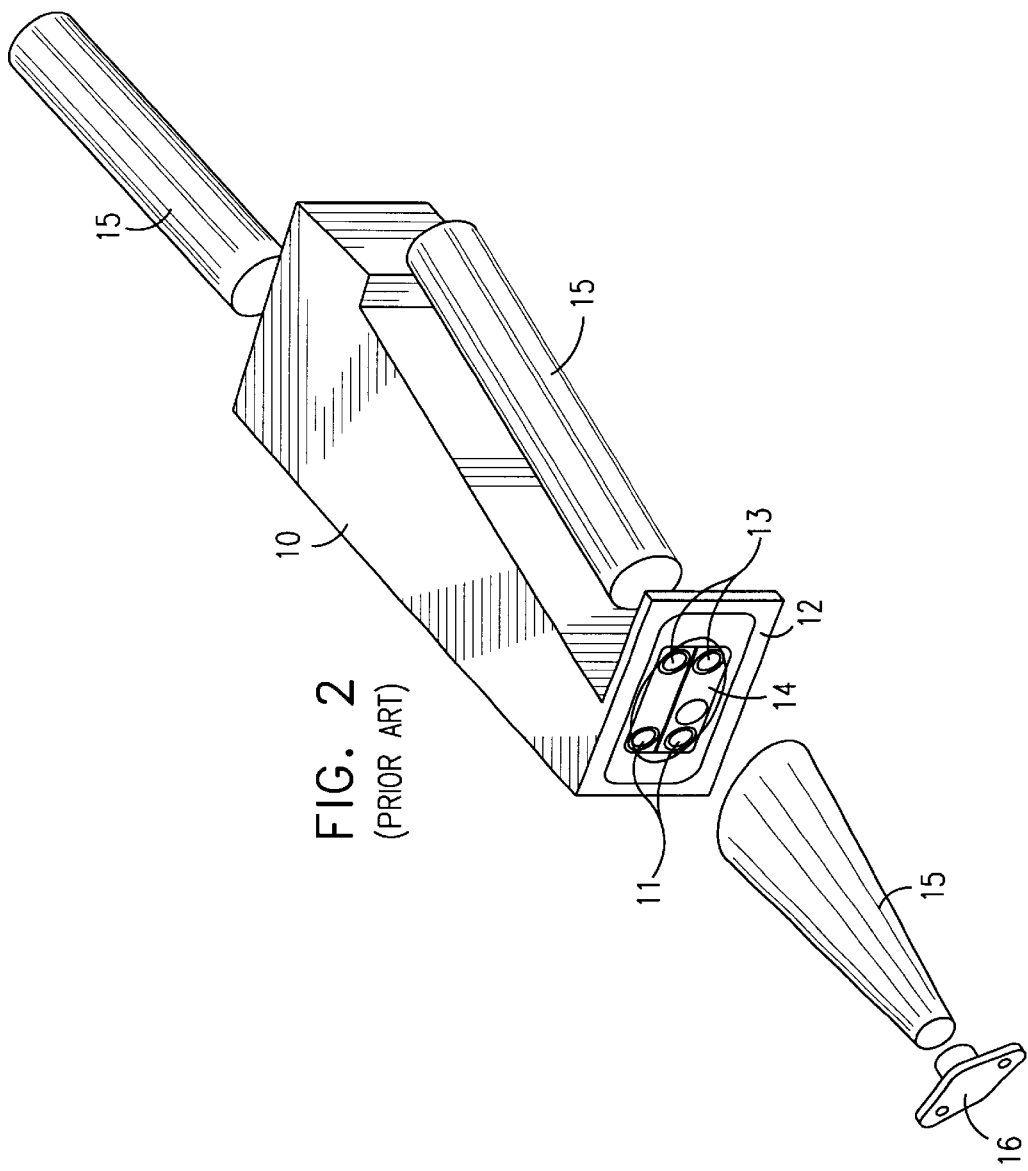
FIG. 2 is an isometric view of a NDIR molecular correlation spectrometer, of the type used in the breath tester shown in FIG. 1.

Reference is now made to FIGS. 1 and 2, which are schematic illustrations of parts of a prior art breath test instrument, of a type in which can be incorporated many of the methods and devices of the various embodiments of the present invention. The illustrations are taken from PCT Publication No. WO99/14576, mentioned in the background section of this application. FIGS. 1 and 2 are presented solely for the purpose of illustrating and clarifying certain aspects of the present invention, and it is not to be construed that the methods and devices of the present invention are limited to applications in breath testers of the type illustrated in FIGS. 1 and 2. The component parts and operation of the breath tester shown in FIGS. 1 and 2 are described in terms of their use for performing $^{13}CO_2$ breath tests.

Reference is now made to FIG. 1, which is a schematic block diagram of the constituent parts of a breath tester incorporating an intermediate chamber system for accumulating and manipulating breath samples, in order to bring them to the desired concentration for analysis. The subject 1 undergoing the breath test breathes or blows into a nasal or oral cannula 2. The breath samples are input into a breath sensor module 3, which is an input capnographic probe whose function is to monitor the waveforms of individual sample breaths, and to determine which parts of each breath to accumulate for analysis, and which parts to discard. The intermediate chamber gas handling system 4, which includes a system of sensors and solenoid valves, is operative to direct parts of the sample breaths either into the sample accumulation chamber 5, or if unneeded, out into the room. As soon as enough gas has been collected, and at the desired concentration, the sample gas is transferred from the accumulation chamber 5 to the NDIR molecular correlation spectrometric measurement cell 6, for measurement of the isotopic concentrations in the gas. A computer-based control system receives and processes the results of the absorption measurements, calculates the isotopic ratios of the samples, and generally controls the complete operation of the intermediate chamber system.

Reference is now made to FIG. 2, which is an isometric view of a prior art NDIR molecular correlation spectrometer, of the type used in the breath tester shown in FIG. 1. The analysis chambers are built into an aluminum block 10. There are two chambers for each isotopic analysis, one sample chamber and one reference chamber. The minority isotope chambers 11 for the $^{13}CO_2$, the ends of which are visible in the end plate 12 of the analyzer block 10, are much longer than those 13 of the majority isotope $^{12}CO_2$. A thin shutter 14 is used for switching the measurement between the sample and reference channels. In the spectrometer embodiment shown in FIG. 2, the isotopically specific sources 15, and the absorption chambers 11, 13, are directed such that the output beams from all four channels are directed by means of a light cone 15 into a single detector 16.

System Check System

Figure 3:
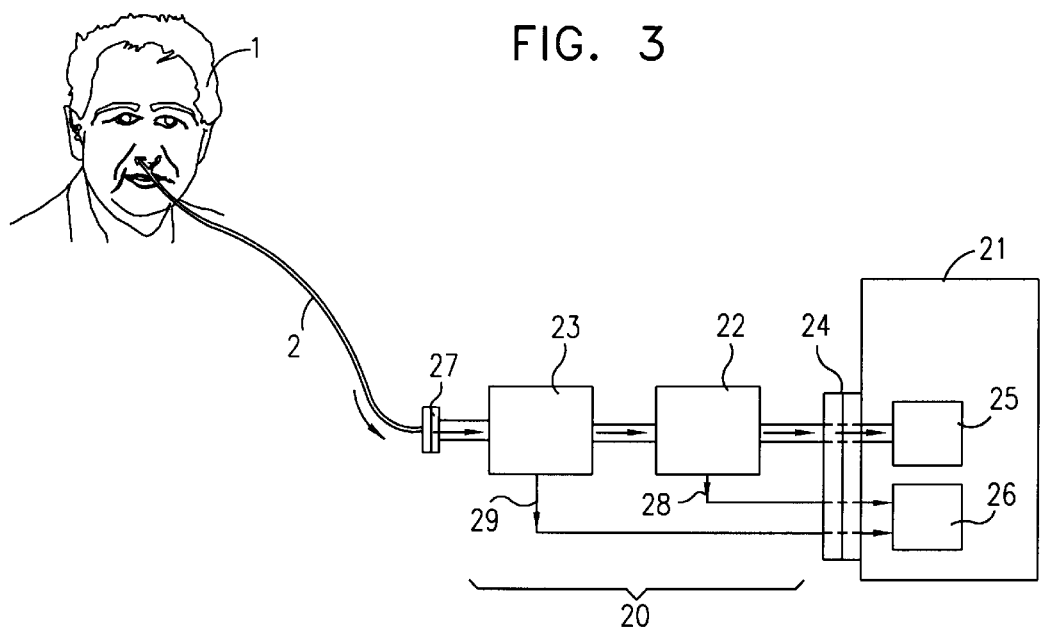
FIG. 3 is a schematic illustration of a gas analyzer system checking device, constructed and operative according to a preferred embodiment of the present invention, connected to a breath tester.

Reference is now made to FIG. 3, which illustrates schematically a gas analyzer system checking device 20, constructed and operative according to a preferred embodiment of the present invention, connected to a breath tester 21. The device consists of two separate components, the calibration checking unit 22, and the fluid filter unit 23. The subject 1 is connected to the device by means of a disposable nasal or oral sampling tube 2, into which he breathes. This sampling tube is connected to the filter unit 23 of the device by means of a mating connection 27. The sampling tube is preferably of a simple nasal/oral cannula type, such that it is a low cost disposable item.

The filter unit 23 is attached to the calibration checking unit 22, or is built-into the calibration checking unit, such that the exhaled breath, after having moisture and/or fluids removed from it, passes through the calibration checking unit 22, into the gas analyzer section 25 of the breath tester 21. The complete gas analyzer system checking device 20 is connected to the breath tester by means of a special flange connector 24, whose function is twofold. Firstly, it provides passage of the exhaled breath to be tested into the gas analyzer 25. In addition, it provides one or more of electrical, electronic, optical, magnetic, gaseous and mechanical interfaces, according to the particular embodiment used, between the gas analyzer system checking device and the breath tester.

The interface mechanism fitted to the system checking unit is preferably constructed such that the first time it is connected to the breath tester, a momentary signal is inputted by means of control line 28 to a controller unit 26 within the breath tester 21, which resets an accumulator unit which counts the number of breath tests performed with each system checking unit. The actual count is performed by the breath tester program, and a count could be added to the total, for example, for every occasion that the "Start Test" command is given to the system.

According to a further preferred embodiment of the present invention, the controller unit 26 within the breath tester 12 is operative to start a timing device which accumulates the total time of operation of the breath tester from first connection of a specific system checking device. In this embodiment, the criterion for use of one system checking device is not the number of tests performed using it, but rather the length of time the breath tester is in operation before a calibration check is considered necessary.

According to another preferred embodiment of the present invention, the signal to reset the test counting mechanism to zero could be provided by the entry of the calibration checking gas itself. According to this embodiment, the analyzer is programmed to detect that the gas entering its input port does not have a conventional breath waveform, and the system thus assumes that the gas entering is from a system checking procedure. Alternatively, a marker gas could be included with the calibration checking gas, and detected by the gas analyzer.

The filter unit, according to other preferred embodiments of the present invention, may also have an interface control connection 29 to the controller unit 26 within the breath tester 21. This control signal could be used for instance, for warning the user when the filter unit is saturated and no longer efficient, or even to prevent operation of the instrument, even before its replacement is mandated by the elapsed time or number of tests performed. For instance, an accidental ingestion of fluid into the sampling tube from the patient before commencement of the breath test, may render the filter useless for continued use, and without a warning to this effect, the subsequent breath test would be unreliable. This control signal could be preferably generated either by optical detection of the change in color of a moisture absorbing material, such as silica gel, or by the closure of electrical contacts when the accumulated fluid reaches a certain level.

Figure 4A:
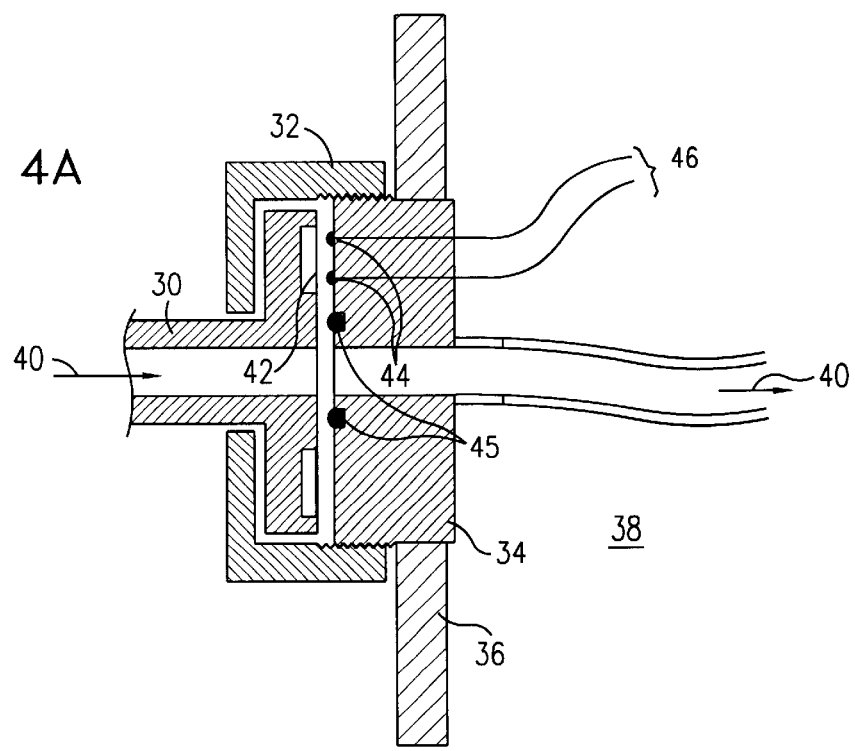
FIGS. 4A and 4B are schematic cut-away illustrations of preferred connector embodiments for interfacing between the gas analyzer system checking device, and a breath testing instrument, where

FIG. 4A shows a cut away drawing of a connector incorporating a simple single-use electrical contact interface. The connector flange 30 on the system checker fluid filter device is screwed by means of a knurled nut 32 onto the mating connector flange 34 mounted on the input panel 36 of the breath tester enclosure 38. An O-ring 45 ensures gas tight closure. Once the connector is closed, the gas being analyzed 40 can flow via the calibration checking unit into the gas analyzer of the breath tester. Mounted on a machined hollow or groove in the mating surface of the flange is a thin metallic foil 42, which, on first instantaneous contact with the connector, touches two contact pins 44. This closes an input signal circuit 46 in the controller unit, thereby enabling the commencement of the count of the number of tests performed with that particular system checking unit installed. However, on screwing the connector completely home, the foil is ruptured, such that subsequent disconnection and reconnection of the system checking unit will not remake the contacts 44, and the clock count cannot therefore be reset to zero using that system checking unit connector. In this way, it is impossible for the operator to attempt to use each system checking unit beyond the recommended number of times by attempting to reconnect it anew after expiry.

Figure 4B:
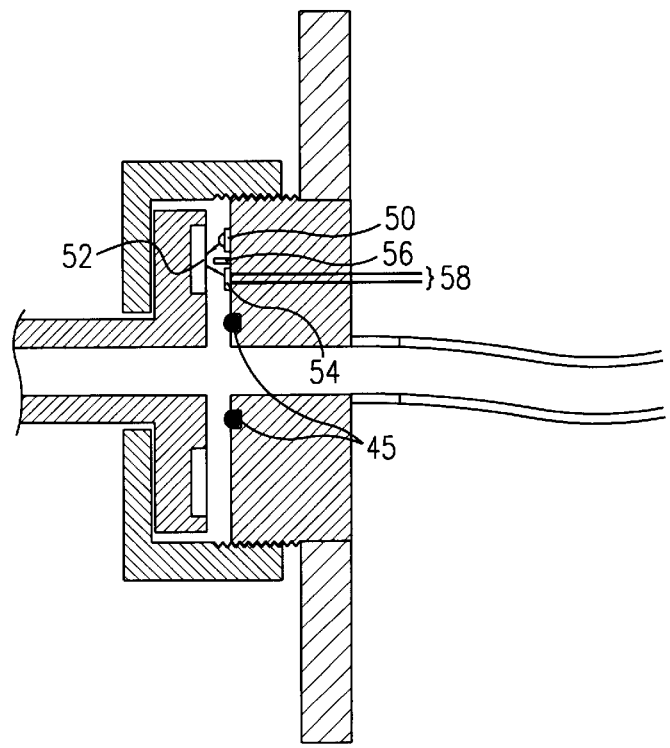

FIG. 4B shows a simple optical interface, which operates in a similar way to the electrical interface shown in FIG. 4A. The trigger signal 58 to commence counting is given by means of the reflection of a light signal transmitted from a source 50 such as a LED, located in the breath tester flange of the interface connector, off a reflective surface such as a metallic foil 52 located in the calibrator flange of the connector, and back to a detector 54 located on the breath tester side. Re-use of the system checking unit after expiry is prevented by a mechanism designed to degrade the reflective properties of the calibrator connector surface so that after first connection, the unit no longer delivers the required signal if reconnected. In the embodiment shown in FIG. 4B, a projection or pin 56, which tears the reflective foil, fulfills this function. Mechanisms similar to those described in FIGS. 4A and 4B can be proposed using magnetic or mechanical interfaces for ensuring that the system checking unit can only be connected once to the breath test unit in an unused state.

Figure 4C:
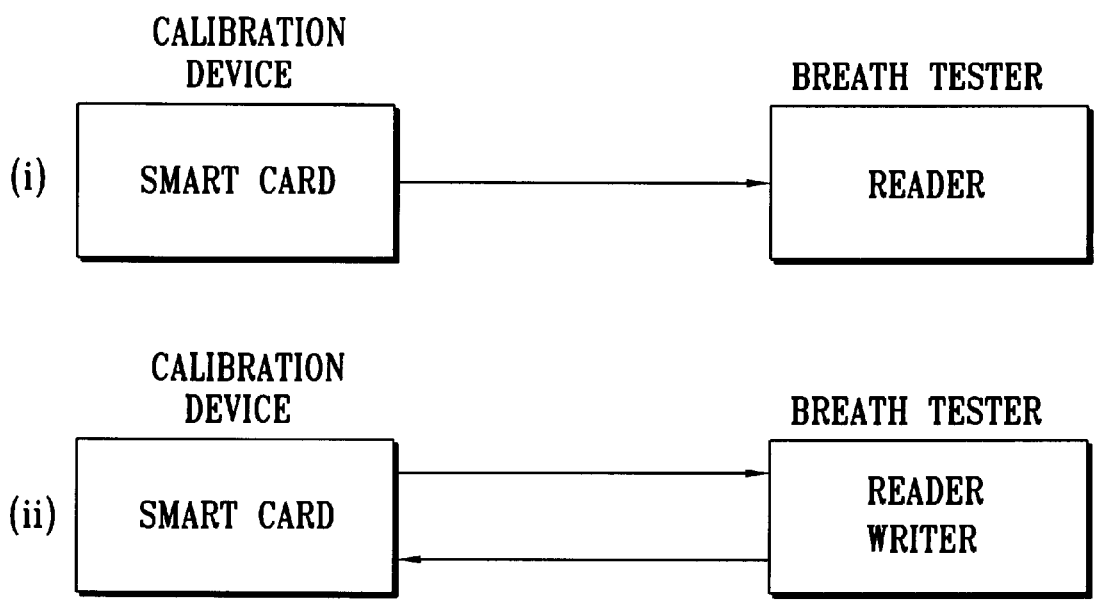
FIG. 4C is a block diagram of the method of interfacing an electronic interface which incorporates an active semiconductor integrated circuit on the calibration checking unit connector.

FIG. 4C now shows block diagrams of methods of interfacing an electronic interface, which incorporates an active semiconductor integrated circuit on the system checking unit. A storage device such as a commercially available smart card can be used, to allow an identification of a specific calibration checking unit through appropriate communication. The same storage device could also be used to store information relevant to the calibration checking process such as instrument serial number, calibration date, number of performed tests. The storage of the instrument number could be used to prevent the storage device from being mistakenly used with another instrument, whose calibration had not been checked.

The IC can function in a number of alternative modes. According to one preferred embodiment, shown in FIG. 4C (ii), the count of the number of tests performed by the particular calibrator is performed and stored in the IC itself, by means of routines well known in the art. According to another preferred embodiment shown in FIG. 4C (i), the IC does not play any part in the counting procedure, but simply has a code, which is unique to the particular calibrator unit to which it is attached. On first connection to a breath tester, this code is interrogated, and is stored in the count register of the breath tester. So long as the permitted number of tests with that particular code number has not been exceeded, the breath tester allows another test to be performed.

Communication between the IC in the system checking unit and the breath tester can be achieved either by a multipin connector, which is engaged when the calibrator unit is attached to the breath tester, or by means of a radio link, or by any other suitable connection means. In the case of a radio link, there is no need to use a special flange on the system checking unit and breath tester.

The above embodiments have been described in terms of an interface designed to commence a count of the number of breath tests that can be performed after each new system checking unit has been used. According to yet further embodiments of the present invention, the interface flange can be constructed to provide an interface between the filter unit and the controller circuit, such that the filter unit is the element which actuates the count as to the specified number of breath tests permissible before stopping operation of the tester until filter replacement is made. The design of the flange could then be identical to that shown in FIGS. 4A and 4B, except that the circuit closing elements are associated with the filter unit.

According to yet another preferred embodiment, the filter unit can be constructed to provide a warning signal to the controller circuit through the interface flange, such as is described above, if the absorbed fluid rises to a level above which the filter no longer operates satisfactorily, or if the moisture absorber becomes saturated, even before the permitted number of breath tests has been performed with it. In this way, the filter function is doubly protected, both in terms of frequency of replacement, and in terms of efficacy.

Figure 5:
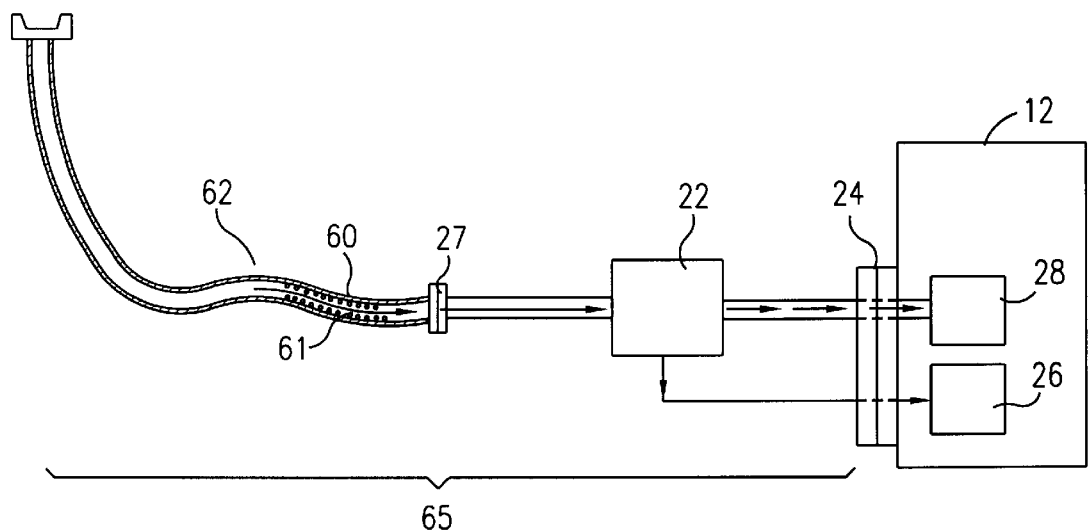
FIG. 5 is a schematic representation of another preferred embodiment, in which the filter function is performed by means of a dedicated section of the disposable oral/nasal cannula sampling tube, which has built-in filtering properties.

Reference is now made to FIG. 5, which illustrates schematically a system checking fluid filter device 65, constructed and operative according to another preferred embodiment of the present invention. According to this embodiment, the filter unit is of low cost, simple construction, such that it is intended to be an built-in part of the sampling tube 62, and is, therefore, disposable like a regular sampling tube. In FIG. 5, the filter is a section 60 of the sampling tube, designed to dry the gas by absorbing moisture, such as by coating the inside walls 61, or partially filling the volume, with a water absorbent material such as silica gel. In this respect, the "filter" does not fulfill the generally accepted functions of removing bulk moisture, and should thus strictly be called a dryer and not a filter. For every new breath test, a new sample line with dryer section is used, being connected to the system checking unit by means of a connection 27. The electronic interface for preventing operation of the instrument is then operative only from the system checking unit. As in the previous embodiments described, the system checking unit 22, is preferably interfaced with the breath tester 21 by means of a "smart" connector 24, which allows control of the number of breath tests performed with each system checking unit.

If a capnographic measurement is to be made of the breath exhaled by the patient, it is important that the waveform of the breath be maintained in passage through the filter unit, to ensure an accurate capnographic measurement. The preferred embodiment shown in FIG. 5 fulfills this requirement, since the gas flow down the sample tube flows in a smooth laminar manner without any significant obstructions or perturbations, and without any pockets or corners of void volume which could disturb the waveform.

Figure 6:
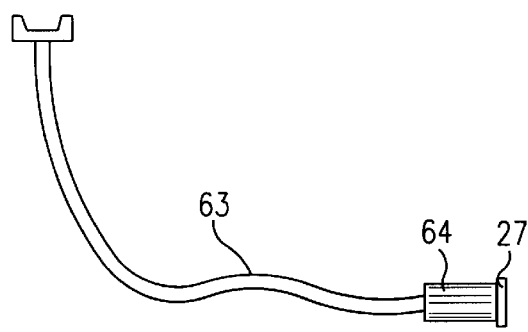
FIG. 6 is a schematic illustration of a sampling filter line whose filter section is preferably one of those described in U.S. Pat. No. 5,657,750, incorporated by reference in its entirety.

Alternatively and preferably, any of the true fluid filtering devices described in U.S. Pat. No. 5,657,750 could also be used for this purpose. The filters disclosed therein are constructed so as to avoid significant disturbance to the waveform. FIG. 6 illustrates a sampling filter line 63 whose filter section 64 is preferably of the type disclosed in U.S. Pat. No. 5,657,750. The sampling filter line is attached to the system checking unit by means of the flange 27.

According to another preferred embodiment of the present invention, the filter unit can be constructed with a color marker which changes color when the filter is saturated, thus providing the user with visible warning that the filter should be replaced, even before the permitted number of breath tests has been performed with it, and the instrument interface would prohibit its further use.

Figure 7:
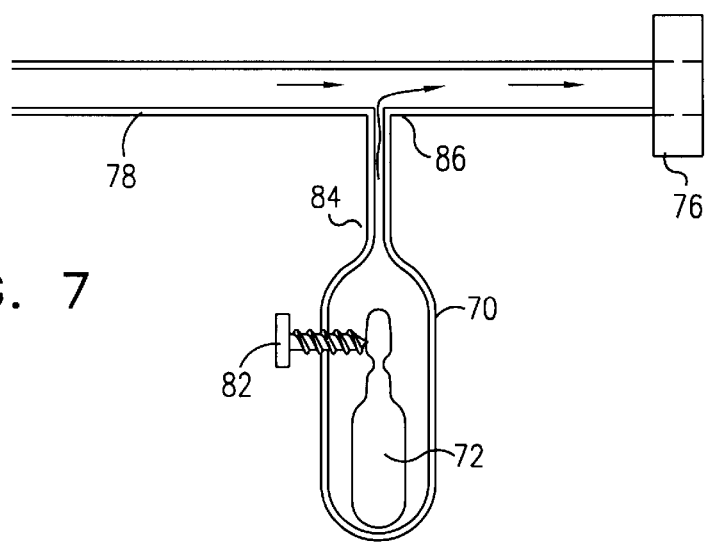
FIG. 7 is a cut-away schematic diagram of an embodiment of a calibration checking unit, showing a glass ampoule containing premixed calibration gases.
Figure 8A:
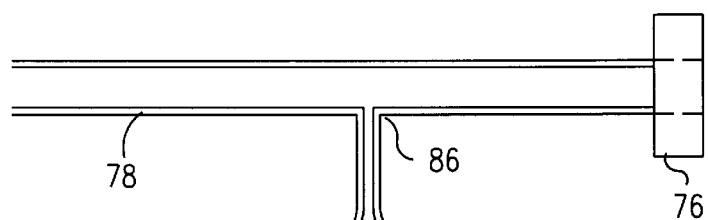
FIGS. 8A and 8B are cut-away schematic diagrams of two preferred embodiments of calibration checking units, with two glass ampoules, each containing premixed calibration gases.
Figure 8B:
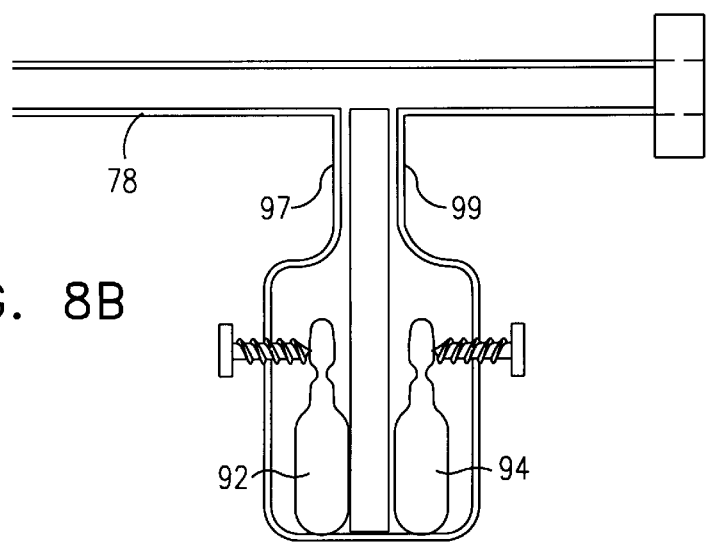

Reference is now made to FIGS. 7 and FIGS. 8A and 8B, which show cut-away schematic diagrams of system checking units, constructed and operative according to preferred embodiments of the present invention. The system checking units incorporate one or more containers of a premixed calibration checking gas, and can be used in any of the system checking devices described in the previous embodiments, regardless of which filter configuration is used. With one exception, the system checking units are in interactive control contact with the gas analyzer control system, such that they either cannot be used without transmitting a start signal to the control system of the gas analyzer, or they themselves are actuated by means of a control signal received from the gas analyzer control. The one exception is the embodiment wherein detection of the calibration checking gas itself by the gas analyzer provides the start signal for the counting or timing process for use of that particular calibration checking device. It is understood that the embodiments shown in FIG. 7 and FIGS. 8A and 8B are schematic only, and serve only to illustrate the operational method. In practice, the shape, dead volume, method of gas release and other details are suited to the gas containers used, such as is described hereinbelow in the embodiments shown in connection with FIGS. 15 to 18.

The operation of the system checking units is described for use with a breath test for the detection of changes in the level of $^{13}CO_2$ in the patient's breath, after ingestion of a $^{13}C$-labeled substrate. It is to be understood, however, that the units can be equally well applied for use in breath tests with other isotopically replaced atoms, such as nitrogen-15 and oxygen-18.

In the embodiment shown in FIG. 7, the system checking unit housing 70 incorporates a glass ampoule 72 containing the system checking gas, though it could be provided in any form of container capable of being hermetically sealed yet easily opened on demand, such as a metallic cylinder with a foil seal or a depressable check valve. The system checking unit is connected through a narrow bore tube 84 by means of a T-connector 86 into the sampling line 78, which is connected to the breath tester preferably by means of an interface connector 76, such as those described in relation to FIGS. 4A to 4C. In the preferred embodiment shown, a plunger 82 is incorporated in the wall of the system checking unit housing 70, such that when the plunger is depressed, the ampoule is broken and the system checking gas mixture released. Though shown otherwise for clarity, the system checking unit housing 70 and the glass ampoule 72 should be constructed in such a way as to leave a minimum of dead space between them, to avoid diluting the released calibration checking gas with residual gas in the dead space.

The long narrow bore tube 84 now acts as a flow restrictor to prevent the calibration checking gas from being released too rapidly into the sampling line 78. This ensures that no overpressure effects are produced in the sampling line. An overpressure may overcome the effect of the system vacuum pump located in the breath tester, and allow some of the calibration checking gas to escape from the system towards the patient's end of the sampling line. Furthermore, the delivery of the calibration checking gas in sidestream fashion to the sampling line via a T-connector avoids any significant disturbance to the breath waveform, since the small entry hole and the long narrow bore connection tube do not present any appreciable perturbation or void volume to the sample gas flow. This is very important for use with any instrument in which capnographic measurements must be made, in order to avoid damage to the waveform of the breath.

Alternative and preferable methods of releasing the calibration checking gas include solenoid plungers electrically operated on demand by the breath tester calibration checking program, or mechanical needles or projections incorporated into the breath tester input flange, which cause mechanical breakage of the gas container seal or depression of a check valve on the calibration gas cylinder as the system checking unit flange is screwed home onto the breath tester flange. Preferred examples are described hereinbelow, and provide more specific details of the schematic examples outlined hereinabove. The operating mechanism of any gas release device not actuated by the control system of the gas analyzer, can be constructed to send its own "calibration check start" control signal when actuated, to the gas analyzer.

When the time comes to perform a system check, a new system checking unit, with or without a filter unit attached, is connected to the breath tester. No subject should be connected to the sample tube, since natural air from the environment is required for the system checking procedure. The calibration check gas is released, either by operation of the plunger, or by another of the methods mentioned above, or by any other suitable method, and the calibration checking gas allowed to mix with the incoming stream of ambient air, and to enter the breath tester.

The ampoule contains a known volume of $CO_2$ such that, with the flow rate ingested by the breath tester, the final percentage of $CO_2$ in the ingested gas is of the order of 5%, which is just above the chosen concentration of operation of the gas analyzer. This level can be achieved, for instance, by defining the volume of gas in the ampoule such that when diluted by the known flow rate of the instrument, the correct concentration is achieved, or by means of an intermediate chamber system, such as that described in the above-mentioned PCT Publication No. WO 99/14576. Since the volume of the intermediate cell described in PCT Publication No. WO 99/14576 is of the order of 300 ml., then the ampoule should have a volume of the order of 15 ml of 100% $CO_2$ at atmospheric pressure, to ensure that a 5% $CO_2$ intermediate cell concentration is reached. If a typical flow rate of 250 ml/min. is ingested, the chamber should be full of gas ready for the measurement in a little over 1 minute.

It should be emphasized here that it is not necessary to achieve the exact target $^{12}CO_2$ concentration level for performing a system check. The important factor for achieving accurate calibration is the isotope ratio present in the gas. This is why it is possible to use a small ampoule of calibration checking gas for dilution with the ambient flow, instead of requiring a monitored flow of accurately diluted gas from the ampoule alone.

The carbon dioxide calibration gas used contains a small added volume of $^{13}CO_2$ above the level of the ambient air. This added volume is calculated to be sufficient to cause the isotopic ratio of $^{13}CO_2$ in the carbon dioxide entering the breath tester to show a slight increase over that expected from a patient showing a negative response to the breath test. Typically, a value of 5δ is used for the calibration check procedure, where δ is 10 parts per million. A value of 5δ enables a clear calibration check to be made, yet at a level close to the typical detection levels demanded of the breath tester in normal use.

The system check is performed by the use of a stream of flowing ambient air, which generally contains no more than 1000 ppm of $^{12}CO_2$ and 10 ppm of $^{13}CO_2$, to which is added a small volume of the calibrating gas at its full concentration level. As an alternative, an ampoule full of ready mixed calibration checking gas at the correct dilution could be used, containing a sufficiently high volume of gas to fill the complete system. This, however, would make the system check more costly, and would also result in a sudden rush of gas into the system as such a large volume of gas is released, which would make it difficult to operate at ambient pressure, without allowing the overpressure to dissipate, thus requiring an even larger volume of calibration checking gas. Furthermore, a container with 300 ml of gas, even if somewhat compressed, would occupy valuable space in such an instrument, compared with a 9 ml sample.

FIG. 8A now shows an additional preferred embodiment for performing the instrument system check, in that the system checking unit housing 90 incorporates two ampoules 92, 94 of calibration checking gas. In the first ampoule 92 is contained a quantity of natural carbon dioxide, whose volume is such that its release into the flow of air through the system will result in the predetermined percentage of $CO_2$ for the measurement system to operate optimally. The level of $^{13}CO_2$ contained is that of the sample used, and the release of the gas from inside the ampoule, such as by operation of the first plunger 96, or by any of the methods described hereinabove, enables a system check of the base line of the measurements, against which all future measurements are made. The second ampoule 94 contains natural carbon dioxide calibration checking gas containing a small added volume of $^{13}CO_2$ in comparison to the gas in the first ampoule 92. This additional volume is sufficient to cause the percentage of $^{13}CO_2$ in the carbon dioxide entering the breath tester to be slightly higher than that of the baseline, which contains $^{13}CO_2$ at a typically naturally occurring level. Typically, a value of $20\delta$ is used. Once the baseline system check has been performed, the second ampoule 94 is opened by means of plunger 98, and a system check at the pre-chosen $20\delta$ level is performed. This embodiment therefore allows the measurement span of the breath tester to be correctly calibrated, in addition to the point system check performed in the single ampoule embodiment. In use, the frequency of performance of a system check, will be determined by local conditions of use of the instrument.

FIG. 8B is a schematic drawing of an embodiment similar to that of FIG. 8A except that the gases from the two ampoules are preferably conveyed to the sampling line 78 in separate tubes 97, 99, in order to avoid any mixing of residual gas remaining from the first ampoule 92, when the second ampoule 94 is broken. Such mixing could interfere with an accurate calibration.

For use in the complete system checking device of the present invention, the system checking unit described in this embodiment may be combined with any of the interfaces or moisture filters described in the previously mentioned embodiments brought hereinabove.

Reference is now made to FIGS. 9A and 9B, which illustrate schematically the operational concepts which are the basis of the system checking methods according to further embodiments of the present invention. FIG. 9A schematically shows a representation of a source of calibrating gas 132, shown for the preferred example of a carbon dioxide breath test, connected by means of a tube 130 to the interface connector 76, where the gas is input to the breath tester. The source 132, can preferentially be either one or more containers of calibrating gas with known concentrations and isotopic ratios, or a system checking device as described hereinbelow, capable of generating samples of calibrating gas of known concentration and isotopic ratio from a reservoir, or alternatively, even an accumulated sample of the breaths taken from subjects either before ingestion of the isotopic labeled substrate, or from subjects whose breath tests show them to be negative, or alternatively, an accumulated sample of breath from a single subject showing a positive result of his breath test. In all of these cases, the breath tester checking system is operative to take the sample of gas, and to dilute it down by means of the intermediate chamber system in the breath tester, into a number of different samples, each of different concentration, but with the same isotopic ratio, since each sample originated from the same, single, calibration sample of higher concentration. The isotopic ratio of each of these samples is then measured in the breath tester. FIG. 9B shows a schematic graph of results typically obtained from such a series of dilutions and measurements. The change in isotopic ratio from the average value, marked as $\Delta\delta=0$, shows a small $\pm 3\delta$ cyclic variation about the average value. Though ideally, a straight line at the average value should be obtained, the realities of experimental and measurement noise are such that the typical result shown in FIG. 9B is acceptable as the output of a reasonably well calibrated instrument. If the curve in FIG. 9B were to show a monotonic dependence on $CO_2$ concentration, this would be symptomatic of a systematic calibration error in the instrument, probably arising from a shift in the absorption curve parameters used to convert luminous transmission into gas concentration.

According to more preferred embodiments of the present invention, the breath tester is capable of performing an independent system check of all of its major functions, including a system calibration check, which is performed by means of a pseudo-breath test on samples of calibrating gas. The pseudo-breath test is accomplished using a breath simulator device, which generates a breath sample with its major characteristics similar to those expected in the normal operation of a real breath test. The characteristics which the device simulates are:

(a) flow rate,
(b) maximum and minimum levels of total $CO_2$ concentration,
(c) $^{13}CO_2/^{12}CO_2$ ratio, and
(d) respiration rate.

The order of magnitude of the values of these parameters of the samples which the breath simulator should preferentially provide are:

(a) Approximately 250 m/min.
(b) Samples of approximately 0 and 5% $CO_2$.
(c) Samples with a ratio typical of breaths tested, and with a $5\delta$ deviation therefrom.
(d) Approximately 15 min$^{-1}$.

Several methods of generating and using such a calibrating gas flow device have been mentioned hereinabove. One of the most convenient devices, according to a further preferred embodiment of the present invention, utilizes a tube of porous material which behaves as a diffusive membrane. Because of the small size of the porous holes, 0.5 $\mu$m or less, there is very little bulk mechanical flow of gas through the wall, but gases, including $CO_2$ can pass through with a relatively high diffusion rate. As an alternative to the non-selective diffusive membrane, a selective membrane with a preferred rate of penetration of carbon dioxide can also be preferably used. One example of such a material is RTV silicone, which has a diffusion rate for carbon dioxide about 8 times higher than for nitrogen, though a much small difference in the diffusion rate for the $^{13}CO_2$ and $^{12}CO_2$, commensurate with the differences in their molecular weights. An advantage of the use of a selective membrane over a porous tube is the comparative lack of interference from the reverse diffusion of air, compared with carbon dioxide.

It should be understood that though these preferred embodiments are described in terms of diffusion of isotopes of carbon dioxide, they are equally applicable to preferential diffusion of any gaseous isotopic cleavage product which appears in the exhaled breath of a patient. Each gas breath tested will in general require its own different porous material, to provide a suitable diffusion ratio for the gases to be measured.

Reference is now made to FIG. 10, which schematically shows a preferred embodiment of such a porous tube device. The gases flow through the tube from one end 150 to the other 152. The wall material 154 is made of a porous material chosen such that the gases flowing within, including carbon dioxide, undergo diffusion 156 out through the wall. If the wall material is a selective membrane, then the carbon dioxide diffuses through it at a significantly higher rate than other gases. If it is a diffusive membrane, the carbon dioxide diffuses through it at a rate, not very different from that of other gases of similar molecular weight, such as oxygen and nitrogen. Whichever embodiment is used, the wall thickness of the porous section, its length and the flow rate of gas through it can be conveniently and preferentially chosen such that in passage down the porous section, the desired proportion of the carbon dioxide content diffuses out.

However, because of the different molecular weights of $^{13}CO_2$ and $^{12}CO_2$, the $^{13}CO_2$ diffuses out more slowly than $^{12}CO_2$ and the result is a small enrichment of the $^{13}CO_2$ level in the gas after its passage through the porous tube. The diffusion constant is inversely proportional to the square root of the molecular weight, M, of the diffusing molecule. By means of mass diffusion calculations, it can be shown that the relative change $\Delta R$ in the isotopic ratio R of $^{13}CO_2$ to $^{12}CO_2$ in passage of the gas down such a porous tube is given by a functional expression of the general form:

$$\Delta R = 1000*(R_{out}-R_{in})/R_{in} = f\{\Delta(^{12}CO_2), (^{12}CO_2)_{in}, D(^{12}CO_2)/D(^{13}CO_2)\}$$

where:

$R_{in}$=isotopic ratio at input to tube $R_{out}$=isotopic ratio at output of tube $D(^{12}CO_2)$=diffusion coefficient of $^{12}CO_2$ $\alpha \sqrt{M}(^{12}CO_2)$ $D(^{13}CO_2)$=diffusion coefficient of $^{13}CO_2$ $\alpha \sqrt{M}(^{13}CO_2)$ $\Delta(^{12}CO_2)$=change in percentage of $^{12}CO_2$ in passage down the tube, and $(^{12}CO_2)_{in}$=percentage of $^{12}CO_2$ at the tube input.

Figure 11:
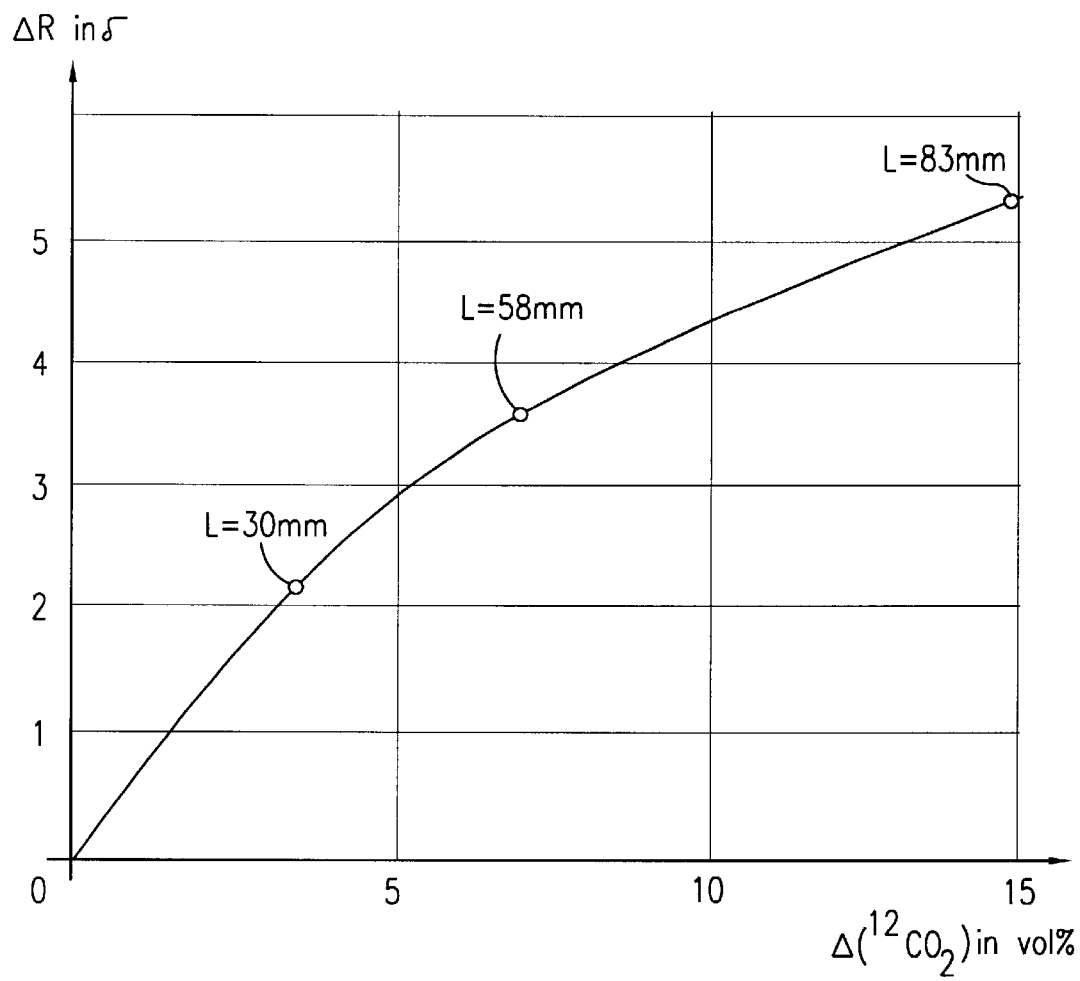
FIG. 11 shows a graph of experimental results of the change in isotopic ratio obtained in the passage of carbon dioxide down a porous tube of the type shown in FIG. 10, as a function of the $CO_2$ concentration and of the length of the tube used.

Reference is now made to FIG. 11, which shows a graph of experimental results of the change in isotopic ratio obtained in the passage of carbon dioxide down a porous tube, according to preferred embodiments of the present invention, as a function of $\Delta(^{12}CO_2)$ and of the length of the tube used. The tube is preferably constructed of a polypropylene material and has an inner diameter of 1.4 mm, an outer diameter of 2.2 mm, and an average pore size of 0.37 $\mu$m. The flow rate of gas is approximately 250 ml/min. The abscissa of the graph depicts $\Delta(^{12}CO_2)$, the change in percentage of $^{12}CO_2$ in passage down the tube, and the ordinate is $\Delta R$, the resulting fractional isotopic increase in the ratio of $^{13}CO_2$ in the gas after passage through the porous tube. The results are plotted for the situation which results in a 5% concentration at the outlet. The length, L, of porous tube used is marked beside each point obtained.

As an example of the use of this graph in the selection and operation of such a porous filter, in order to obtain a 5% concentration $CO_2$ sample flow with a $^{13}CO_2$ isotopic ratio decrease of approximately $5\times10^{-5}$ i.e. $5\delta$, the input concentration of carbon dioxide must be approximately 18%, and the length of tube used approximately 80 mm. This change of $5\delta$ in the level of $^{13}CO_2$, is close to the lower limit of detected level changes, which enable a positive diagnosis to be made using the breath tester. A tube of such dimensions is thus suitable for use in supplying a sample of gas, of known concentration and flow rate, and with a known isotopic ratio change, close to practically detected threshold level changes, for use as a calibrating element.

Though the embodiment shown in FIG. 10 is inexpensive to construct and simple to operate, the presence of ambient air at the outer wall of the porous tube results in one disadvantage in its operation. Because of the likely lack of positive ventilation around the tube, there may be an accumulated carbon dioxide content in the air around the tube, thus creating a different carbon dioxide gradient across the tube wall and a change in the rates of diffusion of the isotopic gases outwards. This will thus cause a change in the calibration factor of the tube.

Figure 12:
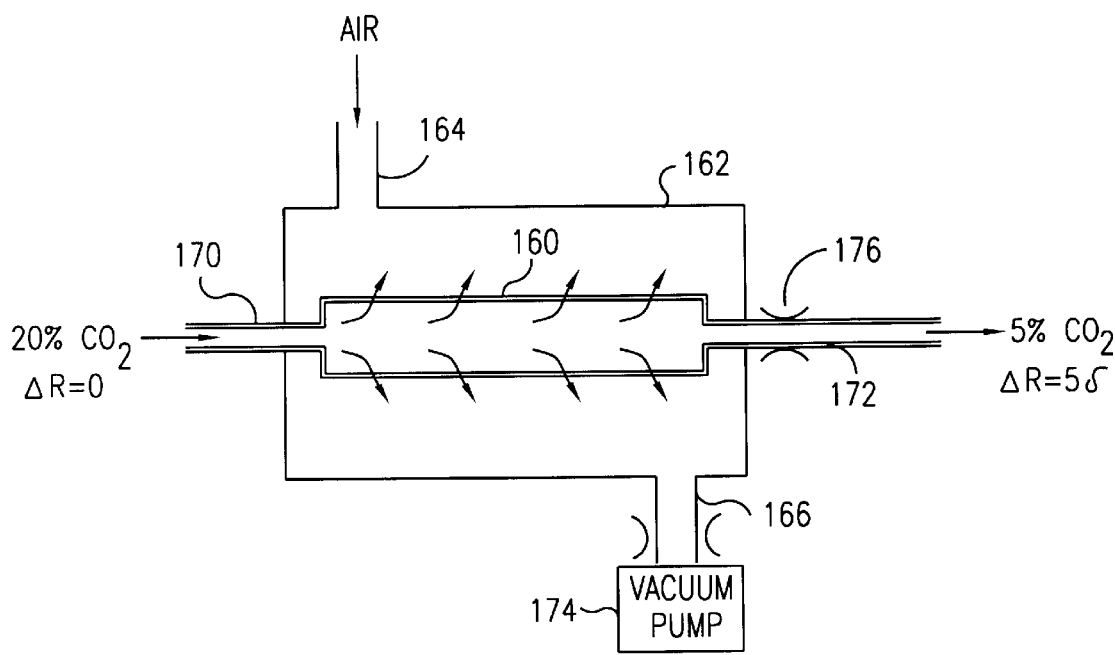
FIG. 12 illustrates a double-stream porous tube calibrator, in which the rate of diffusion is more closely controlled than in the embodiment shown in FIG. 10.

Reference is thus now made to FIG. 12, which schematically illustrates an alternative and preferred embodiment of the porous tube device according to the present invention, wherein the above-mentioned problem is overcome and the rates of diffusion are more closely controlled. This embodiment is known as the double-stream porous tube calibrator. The porous tube 160 is enclosed within an outer housing 162, through which air flows, from the outer housing input 164 to the outer housing output 166. A steady air flow is maintained by means of a vacuum pump 174. The air flow must be sufficient to avoid the generation of an appreciable carbon dioxide gradient across the wall, which would affect the diffusion rate of carbon dioxide through it. A flow of carbon dioxide, as in the embodiment of FIG. 10, passes through the porous tube, from its entrance 170 to its exit 172. The carbon dioxide preferentially originates from a gas source with 20% carbon dioxide, and a flow restrictor 176 determines the flow rate.

In use, carbon dioxide from the porous tube 160 diffuses out through the tube wall and into the inside volume of the outer housing, from where it is removed by the flowing air. The quantity of carbon dioxide diffusing out is determined, as in the simple embodiment shown in FIG. 10, by the tube dimensions and the pore sizes. After its passage through the porous tube, the $^{13}CO_2$ enriched gas flow is used as the calibration checking gas of known concentration, flow rate and amended isotopic ratio, thereby simulating a real breath test sample. The advantage of this embodiment over the simpler embodiment shown in FIG. 10 is that the rate of diffusion across the porous tube wall is now independent of environmental conditions, since both sides of the wall have known and controlled conditions.

Figure 13:
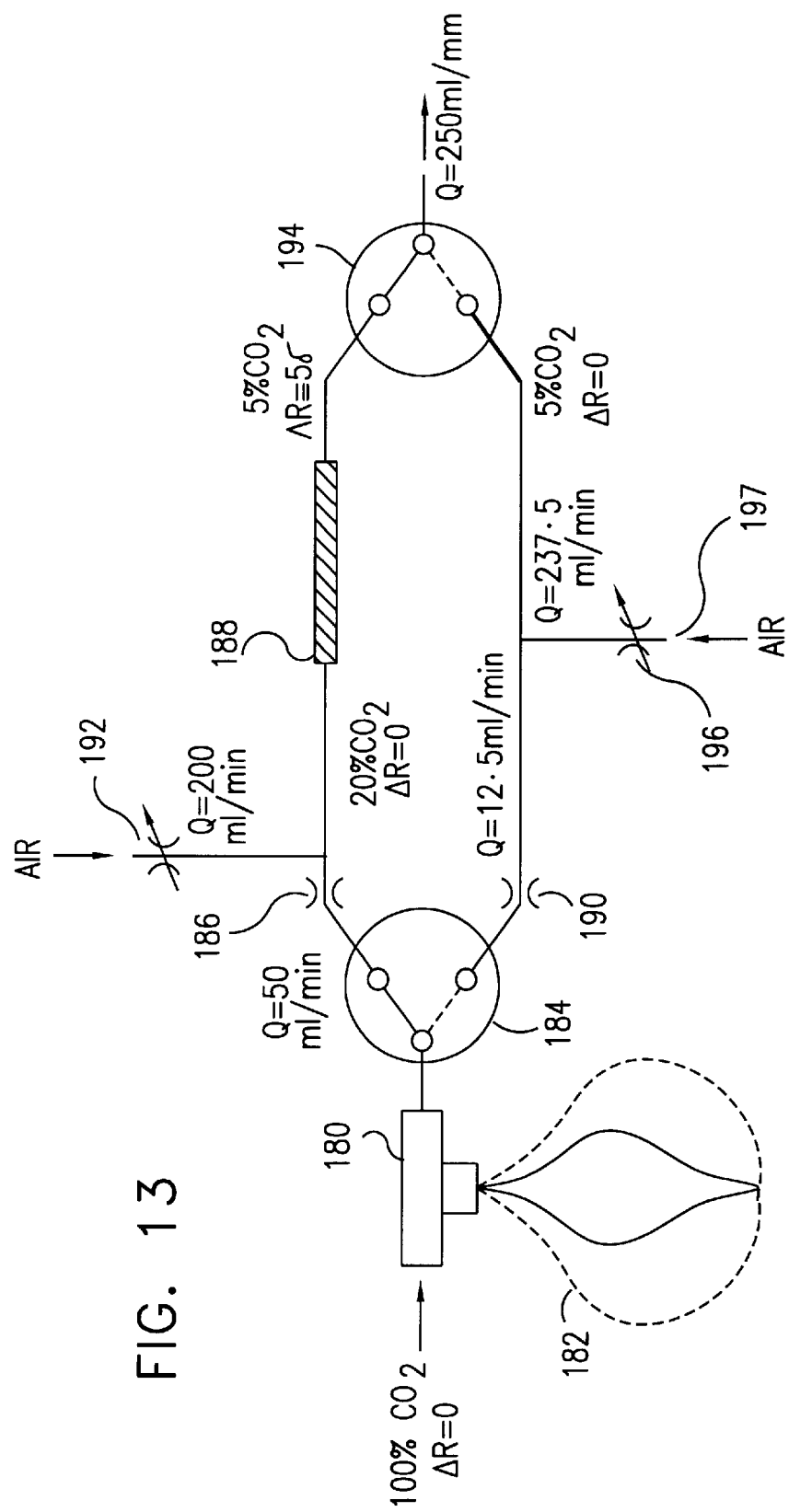
FIGS. 13 and 14 which schematically show different embodiments of flow systems with dynamic isotopic ratio control, for supplying a breath tester with calibration gas samples, incorporating the porous tube devices depicted in FIG. 10 and FIG. 12 respectively.
Figure 14:
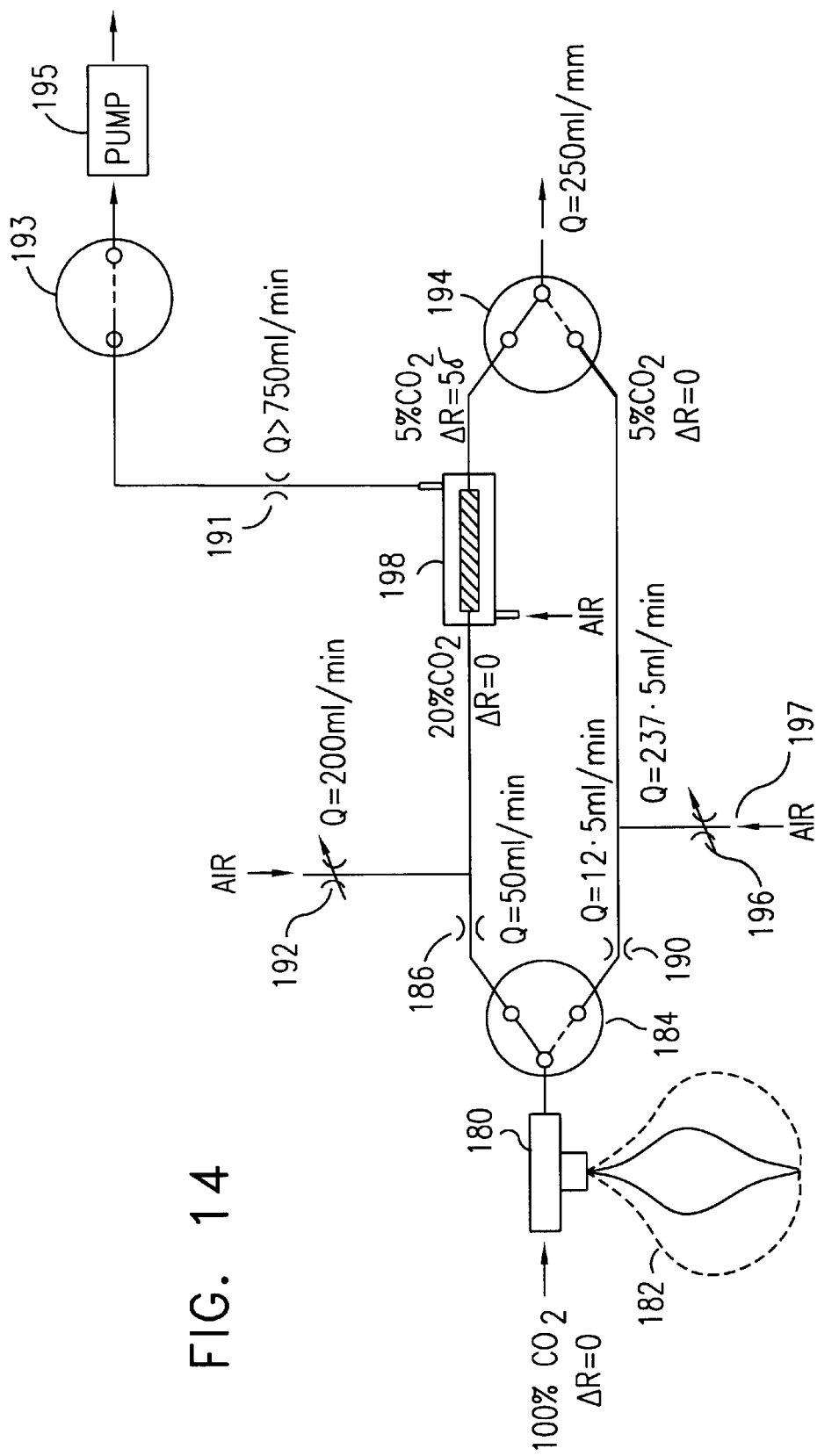

Reference is now made to FIGS. 13 and 14 which schematically show the porous tube devices depicted in FIGS. 10 and 12 respectively, incorporated, according to preferred embodiments of the present invention, into flow systems with dynamic isotopic ratio control, for supplying the breath tester with calibration gas samples. In both of the embodiments shown, the carbon dioxide is supplied in containers filled with 100% carbon dioxide, and at a pressure of up to 5 bar. The use of 100% carbon dioxide enables the smallest feasible volume of gas container to be used, thereby increasing user convenience.

In FIG. 13, the carbon dioxide is input to the flow system through a T-piece 180, to the third arm of which is connected an inflatable bladder 182. The function of this bladder is to regulate the flow of the carbon dioxide into the system when the cylinder or container, typically pressurized at 5 bar, is connected. The initial input flow of higher pressure gas inflates the bladder, which then slowly deflates as it drives the gas gradually into the flow system. In addition to the effect of the expanded bladder, the breath tester itself is fitted with a vacuum pump which provides suction for inputting the gas samples. The carbon dioxide then reaches a switchable solenoid valve 184, which directs the carbon dioxide either into the upper arm via a flow restrictor 186 to the porous tube 188, or into the lower arm, known as the by-pass arm, also through a flow restrictor 190. Before it enters the porous tube 188, the carbon dioxide content of the gas in the porous tube arm is diluted by means of air, input into that arm through a variable flow restrictor 192. This air is preferentially obtained from the line used for inputting the breath samples, since air drawn in through that line undergoes a drying process by means of a fluid filter located in the line. Means are provided for sensing when a nasal cannula is attached to the input connector, and disabling the calibration procedure, to ensure that the porous tube calibrating device is not actuated when a patient is connected to the instrument, since in that situation, the patient's breath rather than air may be ingested.

The single flow porous tube device is able to provide an isotopic divergence as high as 5δ only if the concentration drop through it is limited to about 25%. Consequently, in order to achieve 5% concentration at the output, the carbon dioxide concentration must be reduced before entry into the porous tube device to approximately 20%. The flow restrictor 192 is adjusted to provide the exact concentration of carbon dioxide needed at the input to the porous tube 188. By selection of the correct type of porous tube, the gas, after passage through it, contains 5% carbon dioxide with a 5δ isotopic ratio deviation from the reservoir gas. This calibrating sample is then routed through an output solenoid valve 194, for entry into the breath tester during the calibration procedure.

Gas directed by the solenoid valve 184 into the by-pass branch, passes through the flow restrictor 190, and is then diluted down to 5% concentration by means of air which is admitted through an adjustable restrictor 196. Since the gas in the by-pass arm does not undergo any preferential diffusive process, the isotopic ratio remains unchanged, and ΔR=0. The switchable solenoid valve 194, in its alternate position, routes this gas sample to the breath tester for use in the calibrating procedure.

The flow rate of the gas mixtures is preferably maintained at 250 ml/min, as typically used by the breath tester. For the 5δ sample from the porous tube branch, the settings of flow restrictors 186 and 192 jointly maintain this desired flow rate, with 50 ml/min carbon dioxide flow, and 200 ml/min. air flow. For the zero ΔR sample in the by-pass arm, this desired flow rate is determined by the settings of flow restrictors 190 and 196, with 12.5 ml/min carbon dioxide flow, and 237.5 ml/min air flow.

The flow system shown in FIG. 14 is operationally similar to that shown in FIG. 13, except that a double stream porous tube device 198, such as that in FIG. 12 is used instead of the single flow porous tube of FIG. 10. Components of FIG. 14 with functions identical to those of FIG. 13, are identically labeled. The flow rate of the flushing air in the outer housing of the double stream porous tube device 198 is set at the preferable desired level of more than 750 ml/min by means of the flow restrictor 191. A solenoid valve 193 is located before the exit from the device to the vacuum pump 195, in order to isolate the device from the pump action except when a calibration is required.

Figure 15:
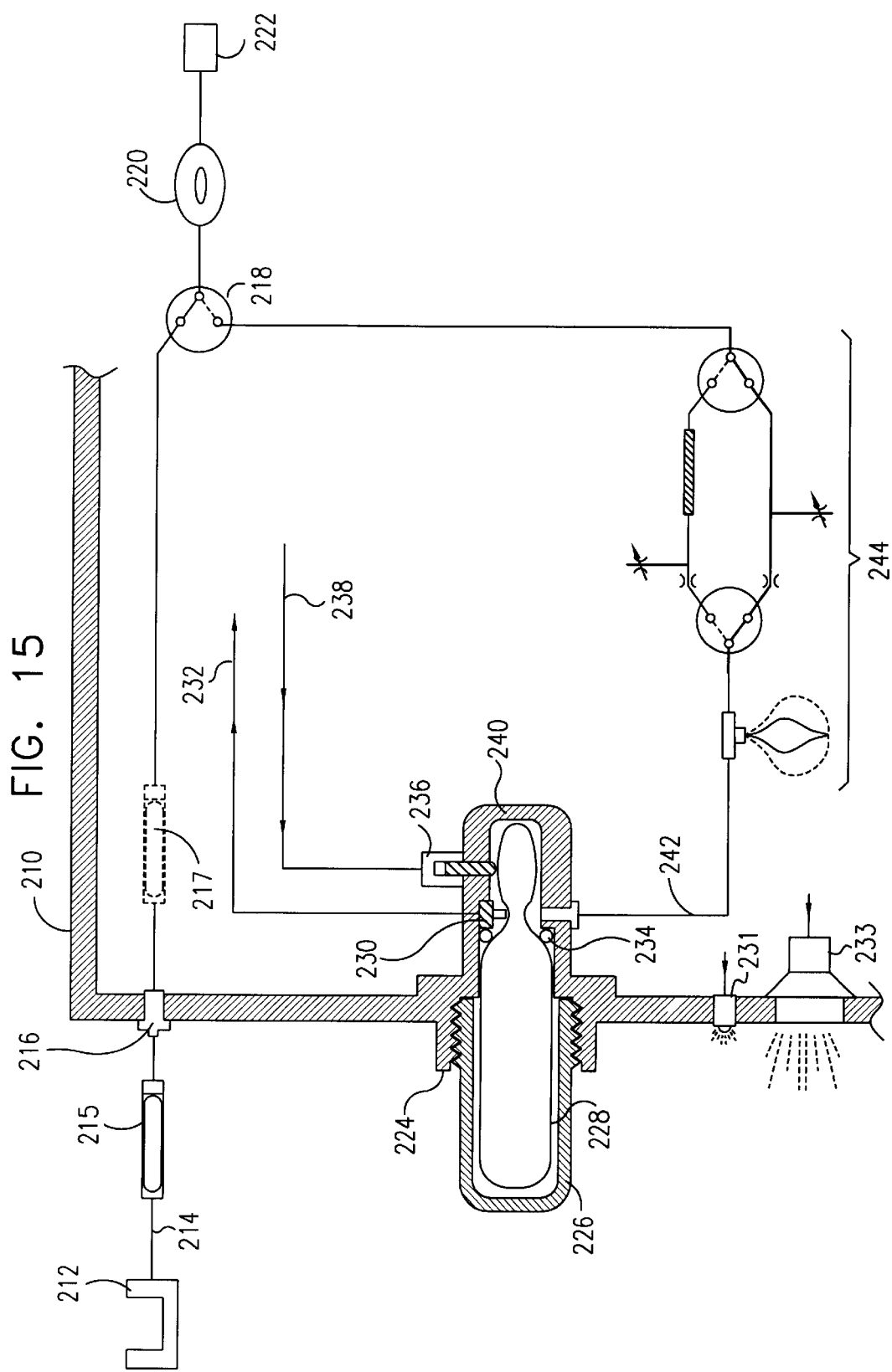
FIG. 15 schematically illustrates a preferred embodiment for the mechanical incorporation in a breath test instrument, of a single-flow porous tube device of the type shown in FIG. 13, for the execution of a calibration check procedure.

Reference is now made to FIG. 15 which schematically illustrates a preferred embodiment for the mechanical incorporation of a single-flow porous tube device for the execution of the service or operator calibration check procedure in a breath test instrument 210. During normal clinical use, the patient's breath samples are collected, preferentially by means of a nasal cannula 212, and conveyed by means of a sample tube 214 and via a fluid filter 215, for removal of excessive moisture and fluids, to the input connector 216 of the breath tester. Alternatively and preferably, an additional fluid filter 217 can be installed inside the instrument in the line conveying the breath sample gas from the input connector ultimately to the gas analyzing system 222. The typical breath collection system provides samples with a flow rate of 250 ml/min, and at a pressure of 50 mbar below ambient pressure, generated by means of a vacuum pump incorporated into the gas analysis system 222. During normal use for breath analysis, these breath samples are routed to the gas analyzer system 222 via the input capnographic sensor 220, by means of a switchable solenoid 218.

Disposed in the front panel of the breath tester is a calibration input connector, preferably in the form of an internally threaded port 224, adapted to receive the externally threaded calibration gas housing 226. According to one preferred embodiment of this calibration gas unit, the calibration gas is contained in a glass ampoule 228 disposed within the housing. The ampoule preferably contains 100% carbon dioxide at a pressure of up to 5 bar, as explained hereinabove. The total volume of calibration checking gas required is 40 ml at STP, which is equivalent to 8 ml at the ampoule pressure of 5 bar. As a result, the gas calibration checking unit is of a conveniently small size. This drawing of the ampoule and its housing shows in more detail the general concept first shown in FIG. 7.

According to another preferred embodiment of the present invention, as the calibration checking gas housing is inserted, a sensor mechanism 230 in the receiving housing detects the presence of the calibration checking gas unit, and transmits a signal 232 to the breath tester control system to enable the calibration checking procedure system. The sensor can preferably be a microswitch, an optical or capacitive sensor, or any other suitable detection device. Alternatively and preferably, the calibration checking procedure may be initiated by means of an operator command from the instrument control panel.

When the calibration checking gas housing is screwed home, an internal gas tight enclosure is formed by means of an O-ring 234, and the calibration checking gas flows into this enclosure when the neck of the ampoule is broken to release the calibration checking gas. The gas tight enclosure is preferably constructed to leave a minimum of dead space around the ampoule neck, so that the ampoular contents are not unduly diluted by residual gas within the gas-tight enclosure. In the preferred embodiment shown, the ampoule is broken by means of a solenoid operated electromechanical mechanism 236 actuated by a signal 238 provided by the breath tester when the calibration procedure is invoked. The ampoule may also be broken automatically by mechanical or other means. In the embodiment shown in FIG. 15, in addition or as a preferred alternative to the solenoid operated mechanism 236, an automatic breakage mechanism is shown in the form of a mechanical stop 240, which breaks the glass neck of the ampoule when the calibration checking gas housing is screwed right home.

An internal tube 242 conveys the calibration checking gas from the gas tight housing to a porous tube flow system 244. The porous tube flow system is preferentially of the type depicted in FIG. 13, though a type such as that depicted in FIG. 14, or any other equivalently functioning type could equally and preferentially be used. The calibration checking gas samples from the porous tube flow system are conveyed to the switchable solenoid valve 218. When a calibration checking procedure is enabled by the breath tester control system, the solenoid valve 218 is switched so that the breath tester inputs the calibrating gas sample, instead of the patient's breath samples.

Figure 16:
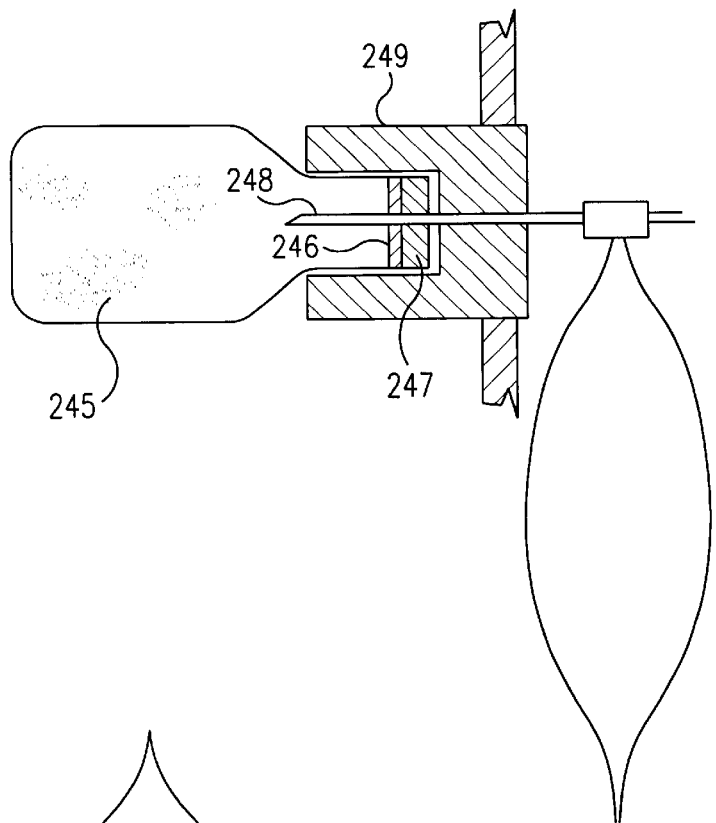
FIG. 16 schematically illustrates another preferred embodiment for the calibration checking gas unit, in which the gas is contained in a metallic housing with a narrow neck for insertion into the calibration input connector on the breath tester front panel.

Reference is now made to FIG. 16 which schematically illustrates another preferred embodiment for the calibration checking gas unit, in which the gas is contained in a metallic housing 245, with a narrow neck for insertion into the calibration checking input connector 249 on the breath tester front panel, in a similar manner to the glass ampoule embodiment shown in FIG. 15. This neck is closed by means of a thin metallic foil 246, preferably of copper or aluminum, hermetically sealed to the metallic housing. The foil is backed with a rubber plate 247. A hollow needle 248 is fixed rigidly in the center of the calibration checking input connector 249, and protrudes therefrom in such a way that, when the calibration checking gas unit is inserted into the connector housing, the needle pierces the rubber plate and the thin metallic foil, so allowing the calibration checking gas to flow through the needle into the breath tester. The narrow bore of the needle acts as a flow restrictor to the calibration checking gas as it flows into the inflatable bag and from there into the porous tube flow system. The gas in the metallic housing is preferably pressurized at 5 bar. The rubber backing plate 247 is operative to provide a hermetic seal between the punctured metallic foil and the needle, so that small movements of the gas calibration checking unit when connected, will not cause leakage of the calibration checking gas during the calibration checking procedure.

The embodiment shown in FIG. 16, being made completely of metal, is able to contain the calibration checking gas without leakage for long periods, providing the calibration checking unit with a long shelf life, typically two years or more. It has an advantage over the glass ampoule embodiment of FIG. 15, in that no glass fragments are produced on use, these being inconvenient, liable to cause injury or damage, or improper connection of the next calibration checking unit if not properly removed.

Figure 17:
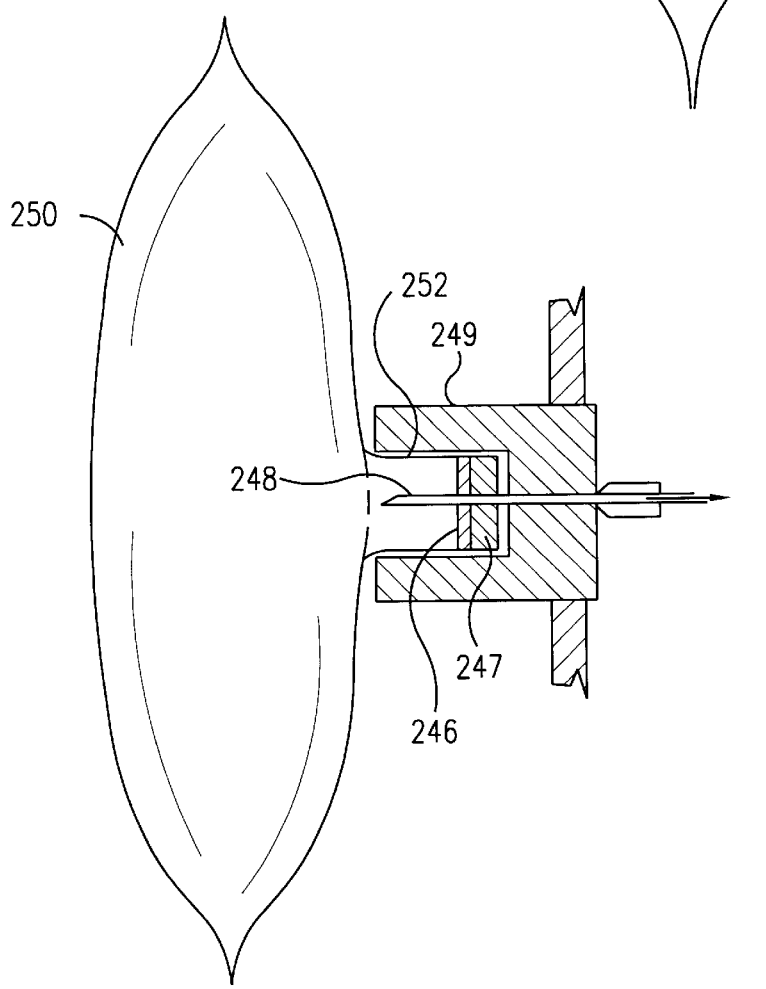
FIG. 17 schematically illustrates another preferred embodiment for the calibration checking gas holder, similar to that shown in FIG. 14, but wherein the gas is contained in a metalized plastic bag.

Reference is now made to FIG. 17 which schematically illustrates yet another preferred embodiment for the calibration checking gas holder, in which the gas is contained in a metalized plastic bag 250. The neck of the bag 252 is similar to that shown in the metallic housing embodiment of FIG. 16, and the bag is connected by means of a similar needle-equipped calibration checking gas input connector 249.

Figure 18A:
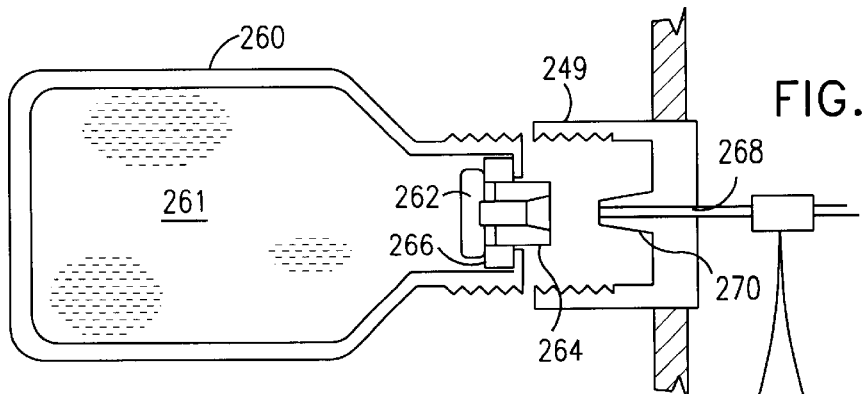
FIG. 18A to FIG. 18C schematically illustrate other preferred embodiments for the calibration gas holder, in which use is made of an aerosol type of container for supplying the calibration gas, with a check valve for containing it.

Reference is now made to FIG. 18A which schematically illustrates another preferred embodiment for the calibration checking gas holder, in which use is made of an aerosol type of container 260 for supplying the calibration checking gas 261. In use, the container screws into a threaded calibration checking input connector 249, from whose center preferably protrudes a conical projection 270, with a narrow gas passage 268 opening into the center of the cone, for conveying the calibration checking gas into the instrument. The gas is held hermetically in the container by means of an aerosol valve assembly, consisting of a valve stem 264, a valve seat 266, and a valve head 262. The valve seat 266 must provide a leak-free seal with the valve head 262, either by use of a layer of properly compliant material, or by the use of an O-ring seal.

Figure 18B:
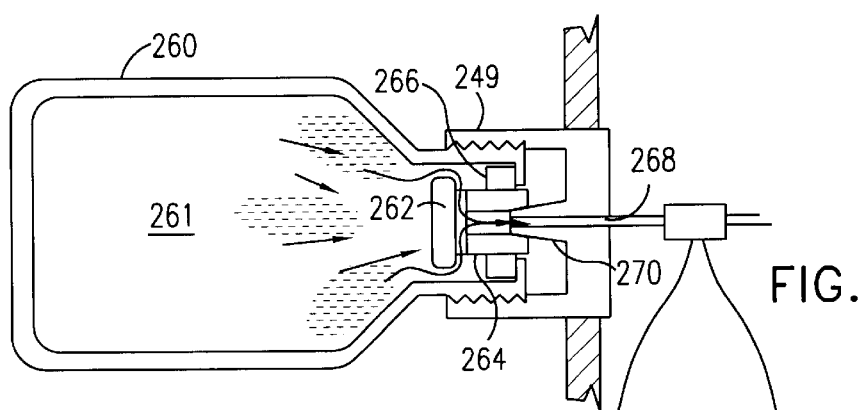

FIG. 18B shows how, as the container is screwed home into the input connector 249, the cone 270 mates with a matching cone in the plunger head 264, and pushes the check valve assembly inwards, thereby allowing the calibration checking check gas to flow through the check valve from the container into the gas passage 268. The matching cones ensure that none of the gas is lost.

Figure 18C:
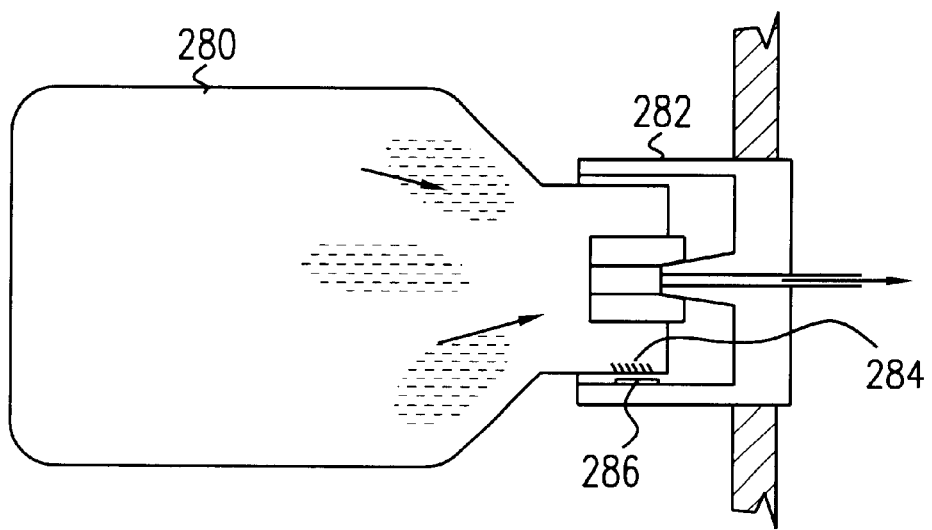

Reference is now made to FIG. 18C, which shows a schematic drawing of a further preferred embodiment for the interfacing of the calibration checking gas container with the input connector, known as the Filterline Recognition System, or FRS. This system includes an electro-optical recognition unit, operative to detect correct placement of the gas container before allowing the calibration checking gas to be released. Confirmation of the correct position also eliminates the possibility of leaks of the calibration checking gas. In addition, the system can also preferably check the identity of the calibration checking gas, and other data such as the serial number of the container or the filling date, to determine its shelf age.

In FIG. 18C is shown a container 280 of calibration checking gas, which is inserted into position in the input connector 282 by means of a pushing action, instead of the screwing action illustrated in FIGS. 18A and 18B. The insertion is preferably performed either manually, or by means of a manually operated mechanism. On the neck of the container is located a reflective label 284, which can be a simple optical reflector, or can contain coded information about the contents, type or age of the gas container. A photoelectric module 286 is mounted in the neck of the input connector. This module consists of a photodiode emitter and a photodetector mounted in close proximity to each other, such modules being well known in the art. The valve in the neck of the container is preferably of the same type as that shown in FIGS. 18A and 18B.

When the gas container is located correctly in position to allow proper and leak-free flow of calibration checking gas into the input connector, optical radiation from the photo-emitter is reflected back from the label 284 into the photo-detector part of the module, thereby providing an enabling signal for the calibration check procedure to commence. According to further preferred embodiments, the photelectric module can be of a type able to read the information on the label for inputting to the breath tester control system.

This FRS system is an additional embodiment of the invention disclosed and claimed in U.S. patent application Ser. No. 08/961,013, entitled "Fluid Analyzer with Tube Verifier", by some of the inventors of the present application.

Figure 19A:
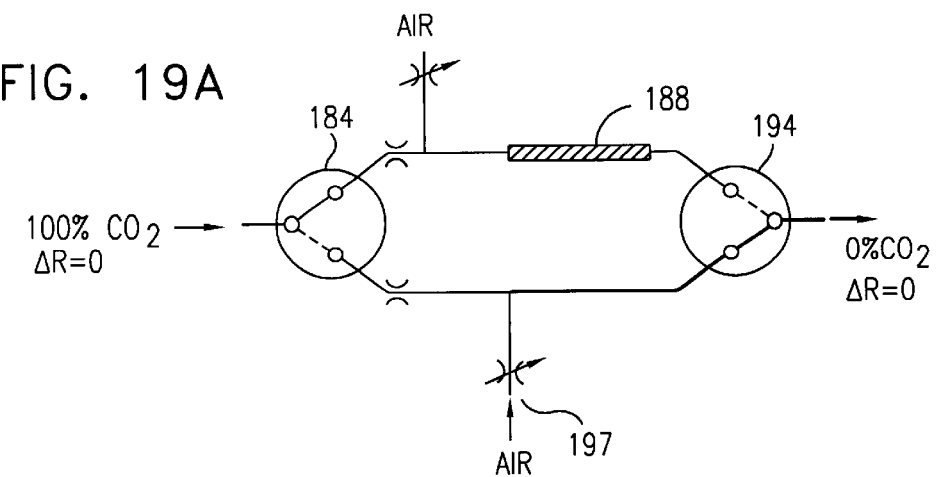
FIGS. 19A to 19C schematically show the operational stages by which a calibration check procedure is performed in the calibration check system shown in FIG. 15.
Figure 19B:
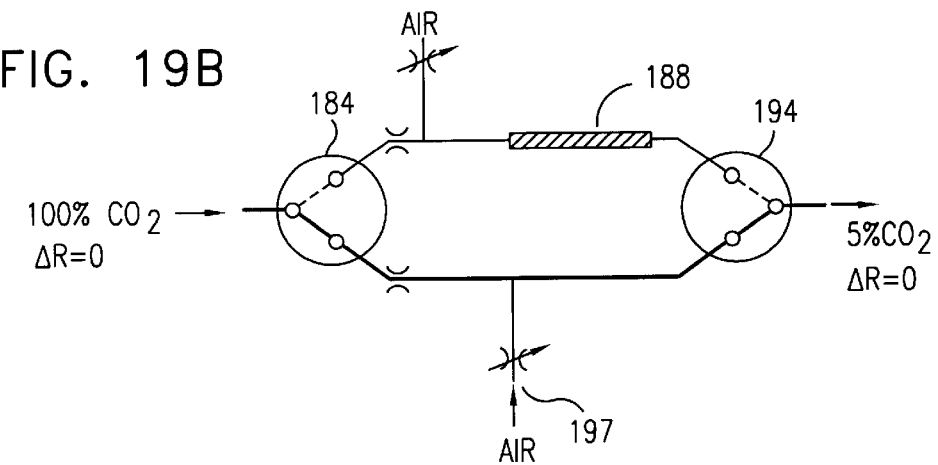
Figure 19C:
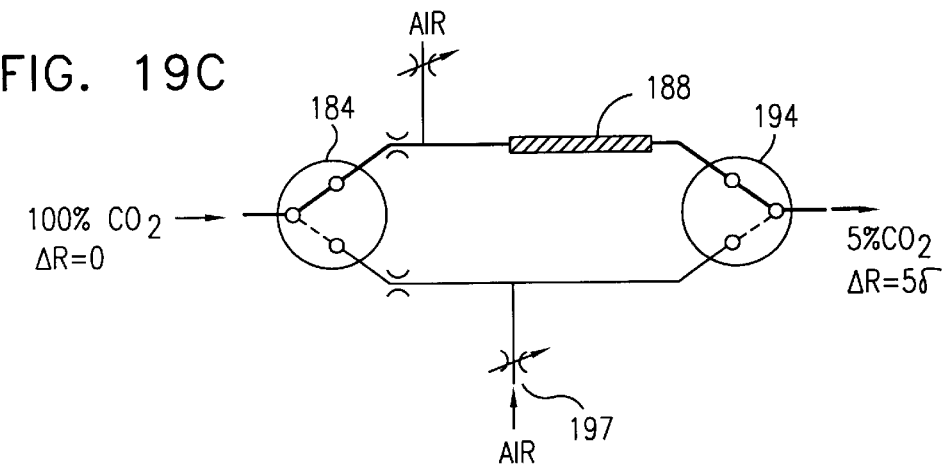

Reference is now made to FIGS. 19A to 19C, which schematically show the operational stages by which a calibration check procedure is performed in the calibration check system shown in FIG. 15. The requirements of the gas samples generated by the calibration device are that they simulate real patient breaths. Three different types of such samples of gas are required for a complete calibration procedure, as designated below. For each of the types of gas, a 150 ml sample is required by the gas analyzer.

(a) 0% carbon dioxide, representing the inhalation stage of the patient's breath. The generation of this sample is illustrated schematically in FIG. 19A.

(b) 5% carbon dioxide with no isotopic ratio deviation (0δ), representing the exhalation stage of a patient's breath before ingestion of the labeled substrate (or of a patient showing a negative result). The generation of this sample is illustrated schematically in FIG. 19B.

(c) 5% carbon dioxide with 5δ isotopic ratio deviation, representing the exhalation stage of a patient's breath showing a raised level. The generation of this sample is illustrated schematically in FIG. 19C.

In FIG. 19A, solenoid valves 184 and 194 are switched such that only gas from the air inlet 197 in the by-pass path is used in generating the calibration sample. The sample thus has the characteristics: 0% $CO_2$, $\Delta R=0$.

In FIG. 19B, solenoid valves 184 and 194 are switched such that undiluted carbon dioxide from the by-pass path is used in generating the calibration sample. The sample thus has the characteristics: 5% $CO_2$, $\Delta R=0$.

In FIG. 19C, solenoid valves 184 and 194 are switched such that only diluted carbon dioxide with an amended isotopic ratio which comes from the path containing the porous tube 188, is used in generating the calibration sample. The sample thus has the characteristics: 5% $CO_2$, $\Delta R = 5\delta$.

The rate of switching of the solenoid 184 simulates the "respiration rate" of the calibration pseudo-breath samples.

The total reservoir requirement for the calibration gas can be calculated from the three calibration gas samples mentioned above.

Sample (a) contains no carbon dioxide calibration gas at all.

Sample (b) uses 150 ml. of gas, of which 5% is carbon dioxide. Requirement is thus 7.5 ml.

Sample (c) uses 150 ml. of gas, of which 20% is carbon dioxide (since the input gas to the porous tube contains 20% $CO_2$). Requirement is thus 30 ml.

Total minimum carbon dioxide requirement is thus 37.5 ml at STP, which dictates the use of a container with 40 ml volume at STP to provide some reserve.

The calibration procedure and unit described in the above preferred embodiments thus provides a check of the system calibration at a level of change in the $^{13}CO_2/^{12}CO_2$ ratio very close to the threshold level above which a breath test is considered to give a definite positive result from the patient's breath samples. For this reason, quite apart from its use as a periodic calibration check of the breath tester, it can also be used as a speedy sensitivity check of the instrument at any time, for determining whether a specific patient's results which are on the borderline of being considered positive, are being correctly measured by the instrument.

Figure 20:
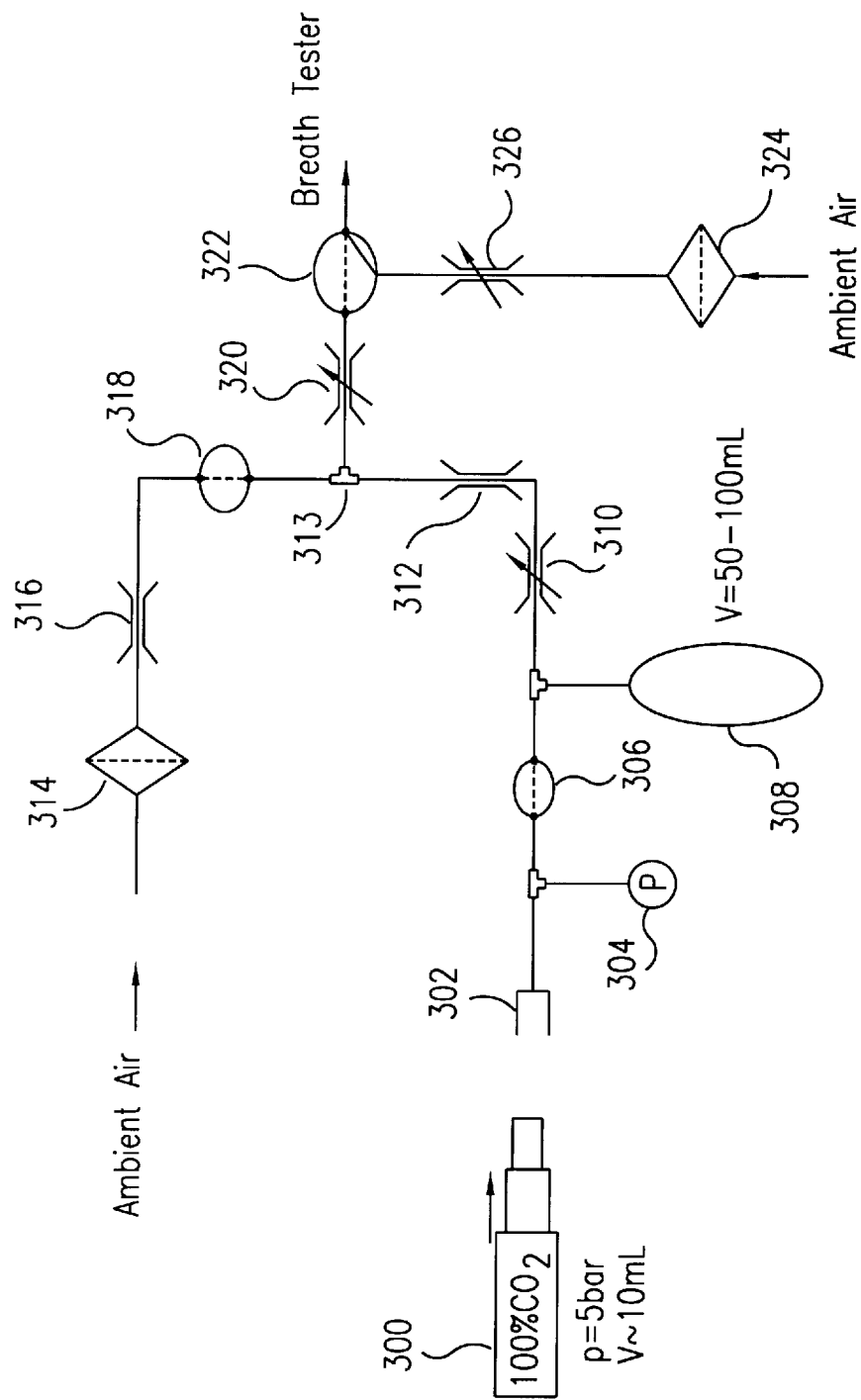
FIG. 20 shows an alternative preferred embodiment for performing a calibration check procedure, differing from that shown in FIG. 15 in that gas with only one known isotopic ratio is provided to the instrument for measurement.

Reference is now made to FIG. 20, which shows an alternative preferred embodiment to that shown in FIG. 15, for performing a calibration check procedure. This embodiment differs in that gas with only one known isotopic ratio is provided to the instrument for measurement. This gas is preferably supplied in a container 300 at an elevated pressure, typically 5 bar, so that the volume of the container is suitably compact. The container 300 is preferably of the aerosol-type, as shown in FIG. 18A, and on insertion into the calibrating gas connector 302 on the breath tester front panel, the calibration gas flows through the check valve into the system, and encounters a solenoid valve 306. This valve is generally shut, to isolate the breath tester from the ambient air, but when the pressure monitor 304 senses the presence of the high pressure gas, it provides a signal for the instrument control to open the solenoid valve 306, allowing the gas charge to enter the system, and to inflate the bladder 308, thus providing a reservoir of 100% calibrating gas, $CO_2$ in the embodiment shown, with a known isotopic ratio $\delta$, and at atmospheric pressure, ready for pneumatic handling by the calibrating system. The solenoid 306 is also useful for providing a long-term air tight seal at the system entry, since the connector 302 is intended for short term use only.

The gas flows via a variable flow restrictor 310, which is used for fine tuning the flow through a fixed flow restrictor 312, to a Tee junction 313, where it is diluted down to a useable 5% concentration by mixing with ambient air, ingested into the system via a dust filter 314, a flow restrictor 316, and a solenoid valve 318 opened when a calibration check is to be performed. The values of the flow restrictors 310, 312, 316 are chosen to ensure the proper dilution ratios to achieve the preferred 5% concentration. From the Tee-junction 313, when the 3-way solenoid valve 322 is appropriately set, the gas flows into the breath tester for measurement of its isotopic ratio. Another flow restrictor 320 ensures the correct flow rate into the gas analyzer. The inhalation stage of the subject's breath is simulated by switching solenoid valve 322 to allow ingest of ambient air into the breath tester, via a dust filter 324 and a flow restrictor 326. By switching the solenoid valve 322, the inhaled and exhaled breaths of the subject can be simulated.

The pressure monitor 304 preferentially fulfills more control functions than that of signaling when a container has been connected. First of all, it can verify that the container connected is indeed a new container, and with the correct full pressure of calibrating gas in it. Additionally, it can provide the calibration control system with the information that a new calibration check container has been installed, and that the breath test counter should be reset to zero, ready for counting the permitted number of tests before a new calibration check is mandated by the system.

As already mentioned, the calibration check processes and the devices described hereinabove are part of a mandatory system check incorporating a calibration check, which should be performed at regular intervals during the use of the breath tester instrument. This is a routine operator calibration check, which is mandated by the need to positively verify the accuracy of the breath tester to avoid the occurrence of false positive or false negative results in patients. The calibration check control system of the breath tester must therefore include a procedure which determines when a new calibration check needs to be performed, and supervises that the test is indeed executed using a new calibration check gas kit.

Figure 21A:
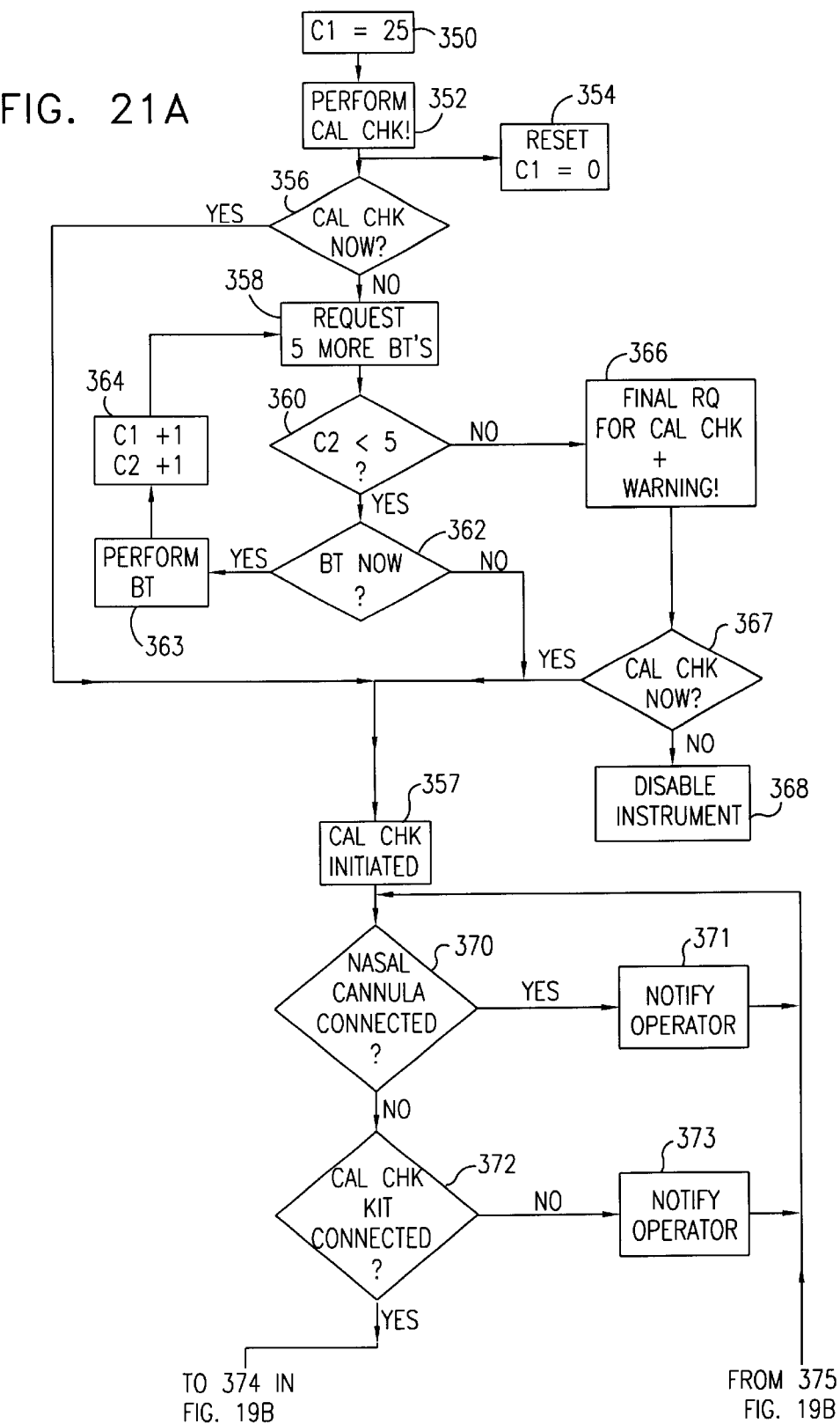
FIGS. 21A–B shows a flow chart, according to a further preferred embodiment of the present invention, of the computational method running within the calibration checking control program, to supervise the demand and execution of the periodic calibration checking tests.
Figure 21B:
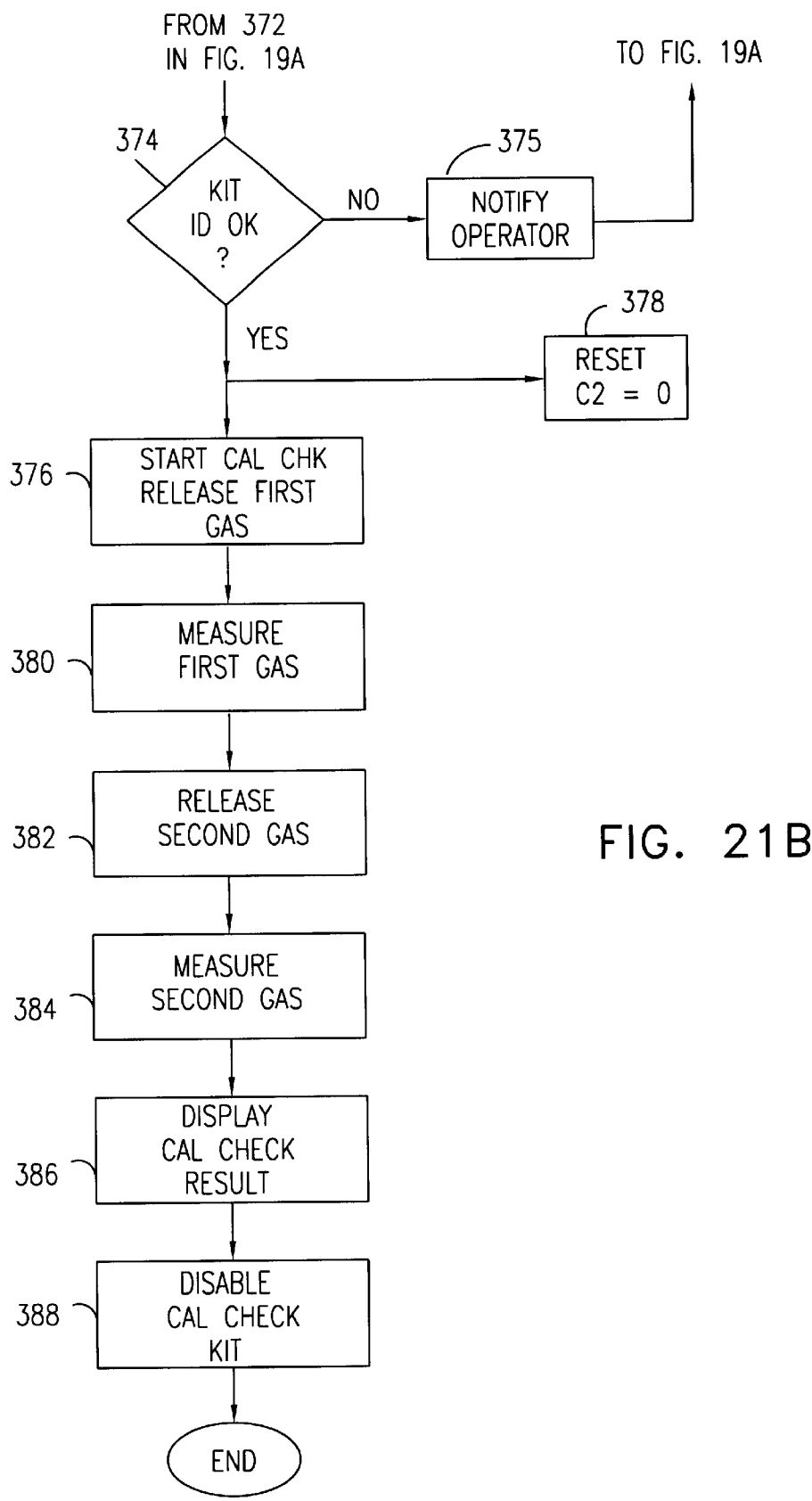

Reference is now made to FIGS. 21A–B, which shows a flow chart, according to a further preferred embodiment of the present invention, of the computational method running within the calibration check control program, to supervise the demand and execution of the periodic calibration checks. A new calibration check is mandated preferably after every 25 breath tests. The main system requirements include that a warning be given to the operator, of the need for a new calibration check procedure after the execution of 25 breath tests from the previous calibration check. The 25th test may, however, fall exactly during the course of a series of related breath tests, or at an inopportune time, such as just one or two tests before the completion of the day's work, when the need to perform a calibration check would cause unnecessary delay to personnel or patients. For this reason, the calculation method is designed to allow an optional five further tests beyond the authorized 25, before the instrument is completely disabled pending a new calibration check.

At step 350, the breath test primary counter C1 reaches a value 25 since it was last reset to zero by execution of the previous calibration check.

At step 352, a message is displayed to inform the operator that a calibration check is due, and that a new calibration check kit should be connected to the breath tester. At the same time, at step 354, C1 is reset to 0.

At step 356, the operator is asked whether to initiate a calibration check now. If the response is affirmative, the calibration check is initiated at step 357.

A negative response indicates that the operator requests, at step 358, the execution of up to a further 5 tests before a calibration check becomes mandatory.

In such a case, at step 360, the procedure initiates a check that there are still some tests remaining of the allowed extra 5. This is done by monitoring that the secondary counter C2 reads less than 5.

If the secondary counter has reached a value of 5, then a final request for a calibration check is issued to the user at step 366, together with a warning that no more tests will be permitted until the calibration check is performed.

At step 367, the operator is asked whether to initiate a calibration check. If the response is negative, then the calculation method disables the instrument at step 368. If the response is in the affirmative, then the calibration check is initiated at step 357.

If the secondary counter, read at step 360, is not yet at 5, the operator is asked at step 362 whether he wishes to perform an additional breath test before the calibration check. If the response is negative, then the calibration check is initiated at step 357.

If the response is in the affirmative, then at step 363, the first of the extra tests requested is enabled. After performing the test, at step 364, both the primary and secondary counters, C1 and C2 are advanced by 1, and at step 358, the calculation procedure is operative to enable the operator to carry on performing more of the five additional tests requested by him.

Once the calibration check is initiated at step 357, the system first checks, at step 370, whether a nasal cannula is connected, which may prevent the ingestion of pure air for the porous tube device of the calibration check kit.

If the response is positive, then at step 371, the operator is notified thereof and requested to remove the cannula, and control is returned to step 370 to check whether the cannula has indeed been removed.

If the response is negative, then at step 372, a check is made as to whether a calibration check kit is attached or not. If the response is negative, then at step 373, the operator is notified thereof and requested to connect a calibration check kit, and control is returned to step 370 to check for the absence of a nasal cannula again, and at step 372, for the presence of a calibration check kit.

If the response is positive, then at step 374, the identity data of the new calibration check kit is interrogated, to ensure that it is the correct kit for the tests being performed, and that it is indeed a new kit.

If the response is negative, then at step 372, the operator is notified of the problem, and is returned to step 370 to recommence the routine for performing calibration check.

If the response at step 374 is positive, then at step 376, the calibration check procedure is commenced by the release of the first calibration gas.

Release of the first gas signals the actual commencement of the calibration check procedure, and the secondary counter C2 is thus reset to zero at step 378.

From this point onwards, the calibration check is described in terms of a two-gas system. At step 380, the first gas is measured, following which, the second gas is released at step 382, and measured at step 384.

At step 386, the result of the calibration check is displayed, and recommended action provided to the operator regarding the need to initiate an operator calibration procedure, as described hereinabove.

At step 388, the identity data of the new calibration check kit is amended by one of the preferred methods described hereinabove to indicate that the kit has been used, and is therefore invalid for further use. The calibration check procedure is thereby terminated.

For a single gas calibration check, using the intermediate chamber system of the breath tester to dilute that one sample down to provide more calibration points if desired, a similar calculation method is used, with slightly amended steps 380 to 384.

Self-diagnostics and Calibration

1. Self-diagnostics

Since the instrument is intended to operate in a point-of-care environment, where there is generally no continuous technician presence, the instrument must have good self-diagnostic capabilities, which define whether it is in good operating condition and fit for use. There are five main levels of activity associated with the operation of the diagnostic system, two levels of diagnostic activity, and three levels of consequential or corrective action, as follows:

(a) Accumulation of a historic database of functional parameters of the instrument operation, such as noise level, drift, correlation of unrelated results, and the like.

(b) Identification of the existence of problem and estimation of its severity. A problem is identified either because of a parameter falling outside the limits of the instrument specification, or because of a systematic change in comparison with the past performance of that instrument.

Once the existence of a problem has been established at level (b), it is dealt with as per levels (c) to (e). The level reached depends on the severity of the problem revealed and its impact on the measurements performed. The levels, in increasing order of severity are:

(c) Automatic application of a correction to measurements being made.

(d) A warning output that instrument maintenance or calibration is required.

(e) Complete disablement of the instrument.

As an example of the different operational significance of each of these levels, the effects of noise present in the measurements is used to illustrate the consequences of each of the above five levels.

(a) The measurements are constantly monitored and the results for a specific time period backwards are stored in a database. The noise level of the results, both in terms of scatter of the actual measurements, and in terms of various operational parameters of the instrument, such as lamp or detector noise are recorded.

(b) The noise level is checked, both for departure from the norm, or from past behavior. If the random noise is below a predefined critical level, the diagnostic method does not define the noise as being sufficiently problematic to prevent the attainment of an accurate measurement. Excessive correlation noise, on the other hand, as will be discussed in the section on instrument calibration below, always directs the instrument into one or other of the recalibration modes.

Identification of what constitutes a critical noise level is dependent on the type of measurement being performed. A measurement which is giving a definite clinical indication of the patient's state of health, showing a strongly positive or strongly negative result, is capable of tolerating a higher level of random noise than a measurement giving a result very close to the threshold level. For results close to the threshold level, a noisy signal could result in a false positive or false negative result, and a much lower critical noise level is therefore required. In this way, the reliability of the breath test measurement is determined as a function of the conditions prevalent during the execution of the breath test itself.

The instrument diagnostic system can be constructed to output a measurement reliability parameter, which is a combination of all of the operational parameters affecting the measurement reliability, as described hereinabove. It could, for instance, be a predefined combination of the closeness of the measured breath test result to the threshold, the noise level encountered during the measurements, and the level of the result itself. The measurement reliability parameter thus operatively defines what constitutes an excessively high noise level, according to the result being obtained at the time the definition is being made.

This parameter, can also be output with the results of the test, in order to give the doctor additional information as to what level of confidence can be attributed to that particular test result.

It should be pointed out that, throughout this specification, the use of the terms "positive" and "negative" to describe the results of breath tests or patients, is taken to mean that the patient shows respectively an elevated or non-elevated DoB (delta over baseline) isotopic ratio. It is appreciated that whether such an elevated DoB is indicative of a state of normal health, or the reverse, is dependent on the particular test being undertaken. For the breath test for *H. pylori,* for instance, it is an elevated DoB that may be associated with the presence of the bacteria. On the other hand, in the breath test for liver function, for instance, a DoB which stays low may be indicative of a diseased state of the liver.

(c) If the noise level is high, but not so high that no meaningful measurements are possible, the diagnostic system applies a compensation procedure to the measurement. A commonly applied compensation procedure is achieved, as an example, by increasing the averaging measurement time of the sample currently undergoing analysis in the gas analyzer.

Another compensation procedure for excessive noise, either instrumental, or a physiological result of the test, is the dependence of the width of the band of threshold levels for the definition of a positive result, on the noise level present, as is discussed in more detail hereinbelow. This compensation procedure has a direct bearing on the measurement reliability parameter output by the instrument.

Yet another compensation procedure for excessive noise is the criterion used for ending the test. Should the noise level be such that a definitive decision concerning the outcome of the test masked by noise fluctuations, a decision can be taken to lengthen the test in order to try to achieve a more definitive result above the noise level.

(d) This level warning is actuated either as soon as a level (c) situation is encountered, or at a higher level of noise severity, depending on the success of the compensation mechanisms in the instrument in achieving an acceptable measurement, with a good level of confidence. At this level, an output is issued by the diagnostic system, warning the user that instrument maintenance or calibration is required, so that the source of the noise can be determined and eliminated.

(e) Once the noise level becomes excessive, and compensation procedures do not enable the achievement of an accurate measurement, a level (e) status is reached. At this stage, the diagnostic system disables the instrument, since. there then exists the danger of the generation of false results.

2. System Checks

The breath tester, according to preferred embodiments of the present invention, is capable of performing independent checks of all of its major system functions by performing a pseudo-breath test on supplied samples of a calibrating gas. In particular, the calibration of the instrument is checked. There are a number of ways in which this may be preferably performed, as described in the section on "Gas calibration checking device" above. The samples can be two physically separate samples of gas mixtures, supplied, for instance, in calibrating cylinders, each gas mixture having a known total $CO_2$ concentration, and a known $^{13}CO_2/^{12}CO_2$ isotopic ratio. The use of two separate calibration checking gases provides information about the absolute gain of the instrument, such that the positions of the two absorption curves are known. This information can then be used to confirm the true position of the $^{13}CO_2$ absorption curve, which, in the instrument calibration procedures to be described below, is assumed to be constant.

Alternatively and preferably, a single gas with a known gas mixture may be used and the intermediate chamber of the instrument used to generate separate samples, each having a different concentration. Even a gas with unknown properties may be used, and the intermediate chamber of the instrument used to generate separate samples, each having the same isotopic ratio but a different concentration.

As an alternative to performing the calibration check by analyzing external sources of gas with known or fixed isotopic ratios, the pseudo-breath test calibration check can be accomplished by using a breath simulator device, which generates pseudo-breath samples with different isotopic ratios from one sample of gas. A breath simulator device is described hereinabove, in connection with FIGS. 13–14. The parameters of the pseudo-breath sample are similar to those encountered in the normal operation of a real breath test, e.g., similar flow rate, similar "respiration" rate, similar $CO_2$ percentage; and similar $^{13}CO_2/^{12}CO_2$ ratio.

The checks performed are of instrument calibration, hardware, software, pneumatics and mechanics. There may be two levels associated with each system check—validation and correction. The former confirms that the system is functioning as specified, and the latter corrects readings in accordance with the results of the diagnostic system output. Alternatively and preferably, if the system check procedures identify the need for calibration, the calibration may be performed at a later time.

Furthermore, the checks may be performed by means of an Internet connection with a central service center, either for on-line diagnostic assistance, or on a periodic basis for routine service checks and maintenance.

2.1 Processing System Self-check

The system incorporates a self-checking facility, operating in a watchdog mode to ensure correct operation of the processing software and hardware. This facility consists of a secondary microprocessor, with its own associated software distinct from the main instrument software. The main system microprocessor generates at regular intervals, a predefined synthesized output sequence. The secondary microprocessor analyses this sequence, and if any deviations from the predefined form are detected, the watchdog system issues a warning and closes down the main processor. The PC is then restarted under the control of the secondary processor, and the reason for the malfunction investigated.

2.2 Hardware Self-check

The complete instrument performs a self check of its hardware, and the software directly involved in operating the hardware. Some of these checks require the use of a known charge of gas in the reference and absorption chambers. Others check the functioning of components of the hardware which operate independently of the specific measurement being made, and therefore do not require the presence of a calibration gas sample.

Approximately sixty parameters are used to characterize the operation of the system. Some of them are monitored continuously during operation of the system, as a real time diagnostic facility. Most of them are monitored only between tests, or when the instrument switches from the stand-by mode to the ready mode. Of the sixty or so parameters, 16 are defined as being critical parameters, and divergence from predetermined allowed values results in interruption in the use of the system. Amongst the critical parameters are:

(a) Light source stability as a function of time (b) Reference cell absorption check (c) Operation of the shutter between reference and sample channels (d) Input capnograph operation (e) Intermediate chamber operation—pneumatics and electronics (f) Feasibility check on values of δ obtained (e.g. negative values, or values with large changes between subsequent breaths actuate the critical parameter flag.)

The component parts of the system with which these parameters are associated are shown in FIGS. 1 and 2, and in more detail in PCT Publication No. WO99/14576, from which FIGS. 1 and 2 are adapted.

To illustrate the use of the critical parameters, the test for light source stability is described in more detail. On initial switch on, the lamp intensity I, as conveyed by an optical fiber from the lamp to a detector, is monitored in the reference channel, in order to determine the lamp stability on warm up. As soon as the time differential of the intensity, $dI/dt$ falls below a predefined level, the lamp is considered to be stable, and an enable signal is output to the instrument control. If the desired stability level is not reached, the instrument waits for a predetermined time for stability to be attained. After the elapse of this time period, a request for lamp maintenance is displayed, and the instrument is not enabled for operation. Similarly, if during operation, $dI/dt$ rises above the predefined level, a disable signal is given to the instrument.

3. System Calibration

The breath test instrument is capable of performing four levels of calibrations, which are operative to ensure that measured differences in isotopic ratios are accurate on an absolute level. These calibration procedures operate by amending the absorption curve parameters used in the gas analyzer for converting optical transmissions into gas concentrations. In this way, they compensate for drifts in the absorption curves, whether due to environmental changes, or to instrumental component changes. Changes in these absorption curves are the most common cause of incorrect calibration in such breath tester instrumentation. These calibrations operate at the software level, within the routines concerned with converting series of optical absorption measurements into isotopic ratio differences. In this respect, they are to be distinguished from the calibration checking procedures described extensively hereinabove, which check the absolute accuracy of isotopic ratios measured, by the use of gases with known isotopic ratios.

The four levels of calibration are denoted:

3.1 Soft calibration
3.2 Self-calibration
3.3 Patient calibration
3.4 Service calibration The first three of these calibration procedures involve no operator or patient intervention, and operate automatically and continually without being requested. Furthermore, the first three of these test procedures, and even one embodiment of the service calibration procedure, are unlike any prior art gas analyzer calibration procedures, in that they use the subject's own breaths, both in order to determine whether calibration is necessary, and in order to perform the recalibration procedure itself. Procedures are known wherein a sample bag of breath provided by the operator or nurse is used as the calibration gas sample, but such a sample is like any unknown, externally provided calibration gas, and certainly requires operator initiation and intervention.

In addition, the first of these calibration procedures is an ongoing process, operating continually in the- background. As a result, trends in the instrument calibration can be better identified than is possible using any external calibration which relies on a procedure performed at a specific point in time, which may, by chance, fall at a moment when a temporary change or an atypical event occurs in the instrument.

A second embodiment of the service calibration procedure indeed utilizes an externally provided gas sample or samples for its calibration procedure. All of the calibration procedures described, except the soft calibration, are based on the measurement of the relationship between the isotopic ratios measured in gas samples of different $CO_2$ concentration derived from samples of gas with the same isotopic ratio.

3.1 Soft Calibration

This calibration is purely software based, and operates continuously in the background of the system, without requiring patient or operator intervention or involvement. This procedure continually monitors the results of breath sample analyses obtained from subjects with results close to the baseline. For instance, for the *H. pylori* breath test, this means subjects who proved negative. According to a preferred embodiment, the system software monitors the results of all of the patients tested over the last 2 to 3 days who showed negative response to the breath test. The measurement points used for this test are those obtained for the baseline measurement taken before the ingestion of the isotopic labeled substrate, and those obtained after the cessation of any oral activity which arises from possible interactions of the labeled substrate with bacteria present within the oral cavity.

Each of these negative patients provides breath samples, each generally having a somewhat different and random level of $CO_2$ concentration, such that each absorption measurement is performed at a slightly different point on the absorption curve. Preferably, breath samples with $CO_2$ concentrations of from 2.3% to 2.7% are used, so that deviation of the absorption curve is checked over a range of values instead of at one point only.

This is in contrast to the routine measurement procedure, where the use of a constant concentration within each test is an important feature in the reduction of the sensitivity of measurement accuracy to the state of the instrument calibration. So long as all of the absorption measurements in one test are performed at one concentration level, any drifts in the isotopic absorption curves affect, to first order, all of the measurements equally, such that any lack of calibration thus becomes a second order effect. There may indeed be an error in the ratio measurement $^{13}CO_2/^{12}CO_2$ because of change in the absorption curve, but the error appears equally in all of the measurements, and thus does not affect, to first order, the changes in ratio detected.

In the soft calibration procedure, all of the samples tested from a single negative patient should, within the noise limits of the measurement, have the same isotopic ratio, despite their having different concentrations. If, however, the ratios measured are not the same, but show a correlation with the sample $CO_2$ concentration, this is symptomatic of a change in the absorption curve from its correctly calibrated value. The "soft calibration" method then applies a correction to the shape or position of the absorption curve, to bring the instrument back into calibration, which is indicated by a lack of correlation between the isotopic ratios and concentrations. The way in which the correction is performed is explained hereinbelow. After correction of the shape of the absorption curve, the data of all of the negative patients over the past 2–3 days is again checked for correlation between concentration and isotopic ratio, to confirm that the recalibration procedure was successful, which is indicated by a reduction in the aggregate correlation level for all of the data. Since this calibration procedure operates continually in the background, it maintains a constant state of recalibration of the instrument with respect to shifts of the absorption curve in the operating concentration range.

If, for a soft calibration procedure for a particular patient, no significant correlation between differing measured isotopic ratios and the concentrations is found, then the system is considered to be correctly calibrated, and no adjustment to the absorption curve parameters is made at that point.

In addition to correlation between isotopic ratio and concentration, the soft calibration process can be programmed to inspect for correlation between isotopic ratio and any other function which could affect the calibration of the instrument. Among such functions are environmental conditions, such as the temperature present within the instrument, which has a noticeable effect on the absorption curves.

3.2 Self-calibration

This procedure, like the soft-calibration, also operates automatically without operator or patient involvement. Unlike the soft-calibration procedure, however, it involves both the instrument hardware and the processing software. The procedure commences at the conclusion of a breath test if two conditions are fulfilled:

(i) that the patient tested showed a negative result, and
(ii) that the total percentage of carbon dioxide in the patient's alveolar breath was reasonably high, preferably 4% or more.

The intermediate chamber operation is adjusted to provide a single accumulated sample with a high $CO_2$ concentration, e.g. 3.5%, such as would be obtained by collection of alveolar breath only. This sample is measured for isotopic ratio, and is then diluted down by the intermediate chamber system to provide preferably two additional samples with lower concentrations, such as 3%, 2%, each of which too is measured for isotopic ratio.

In order to provide more points for making the calibration assessment, the self-calibration procedure also preferably uses the results of data obtained at around the preferred operating point of the absorption curve, taken from the patient's previous breaths. A total of five points is preferably used, three derived from the high concentration single sample and its diluted derivatives, and two more from previous negative breaths taken during the test. The object of this spread of sample concentrations is to cover as large a part of the concentration range of the absorption curve as possible.

The isotopic ratio is checked at each of the five concentrations. Since each of the samples originates either from the same accumulated breath sample, or from other breaths taken from the same negative patient close in time to the collection of the accumulated breath sample, the measured isotopic ratios should be identical. Any divergence is indicative of a drift in the absorption curve, as described above, and the recalibration procedure is thus initiated to eliminate this correlation of isotopic ratio and concentration.

Since this self-calibration procedure takes place after the completion of the breath test, such as for instance, when the next patient is being readied for his test, it does not require virtually any additional instrument dead time.

3.3 Patient Calibration

In a situation where the instrument is not in continuous use, or has not been used for a period of time, or if the initial system check detects a need for an immediate calibration, the system automatically initiates the performance of a patient calibration procedure. In this procedure, the first several breaths of the patient, before administration of the labeled substrate, are collected and diluted down by means of the intermediate chamber, to provide a number of successive samples of different concentration. Each of these samples should have the same isotopic ratio, since they are all taken from a single patient and at the baseline level. The calibration procedure then adjusts the absorption curves, as previously, until the ratios obtained from the samples of different concentration are all the same. A preferred criterion for determining whether recalibration is required is that, for example, the isotopic ratio should vary by less than $3\delta$ (i.e. less than 30 ppm) for changes in $CO_2$ concentration of from 3% to 1.5%.

Since this procedure lengthens the time during which the patient has to supply breath samples, it is less desirable from the point of view of patient tolerance than the self or soft-calibration procedures, but apart from the slightly lengthened sampling time, it too does not involve any conscious patient or operator involvement.

With any of the three above-mentioned calibration procedures, there exists the possibility, according to further preferred embodiments of the present invention, of correcting the results of tests performed in the past, using the newly found calibration data. If, for instance, the test results show a strong correlation between ratio measured and concentrations, and the calibration calculation procedure applies a correction to the absorption curve, it is possible to use this correction not only for future measurements, but also to correct past measurements.

If, the lack of correlation is revealed at the conclusion of a certain test, but the data available from that test is insufficient to perform a complete calibration, or if the breaths available from that test do not cover a full enough range, then the system can recommend the performance of a patient calibration procedure in order to accumulate sufficient accurate data for performing a retroactive calculation of the results of that test. According to this preferred embodiment, the patient need only give a few more breaths at the conclusion of his test, and can then be released.

3.4 Service or Operator Calibration

This is similar to the patient calibration procedure, except that it is technician or operator initiated when the need to perform calibration becomes apparent, or is mandated by external causes, such as following service, or after expiry of the maximum inter-calibration period required to maintain the instrument in accurate condition. In this procedure, the gas used can be either operator breath samples, by means of a method as previously described, or an external container of a calibration gas, such as is included within the periodic system calibration check kit described in the section on the system calibration check hereinabove.

3.5 Calibration Correction Method

Recalibration is required when the physical parameters of the gas analyzer undergo change such that the absorption curves differ from those which existed when the instrument was last calibrated. The significance of this is that the function which correlates the absorption cell transmittance to the detected gas concentration has changed. In this situation, recalibration is achieved by applying a correction to the absorption curves to bring them back to their correct form, such that a specific detected intensity is equivalent to a given gas concentration. This recalibration process is accomplished by means of the calibration correction method, whose stages are now described. The description is first given for a full hardware-involved calibration, such as the self, patient or service calibrations, and then for the soft calibration, which is a software-only procedure.

3.5.1 Regular Calibration Procedure

Figure 22:
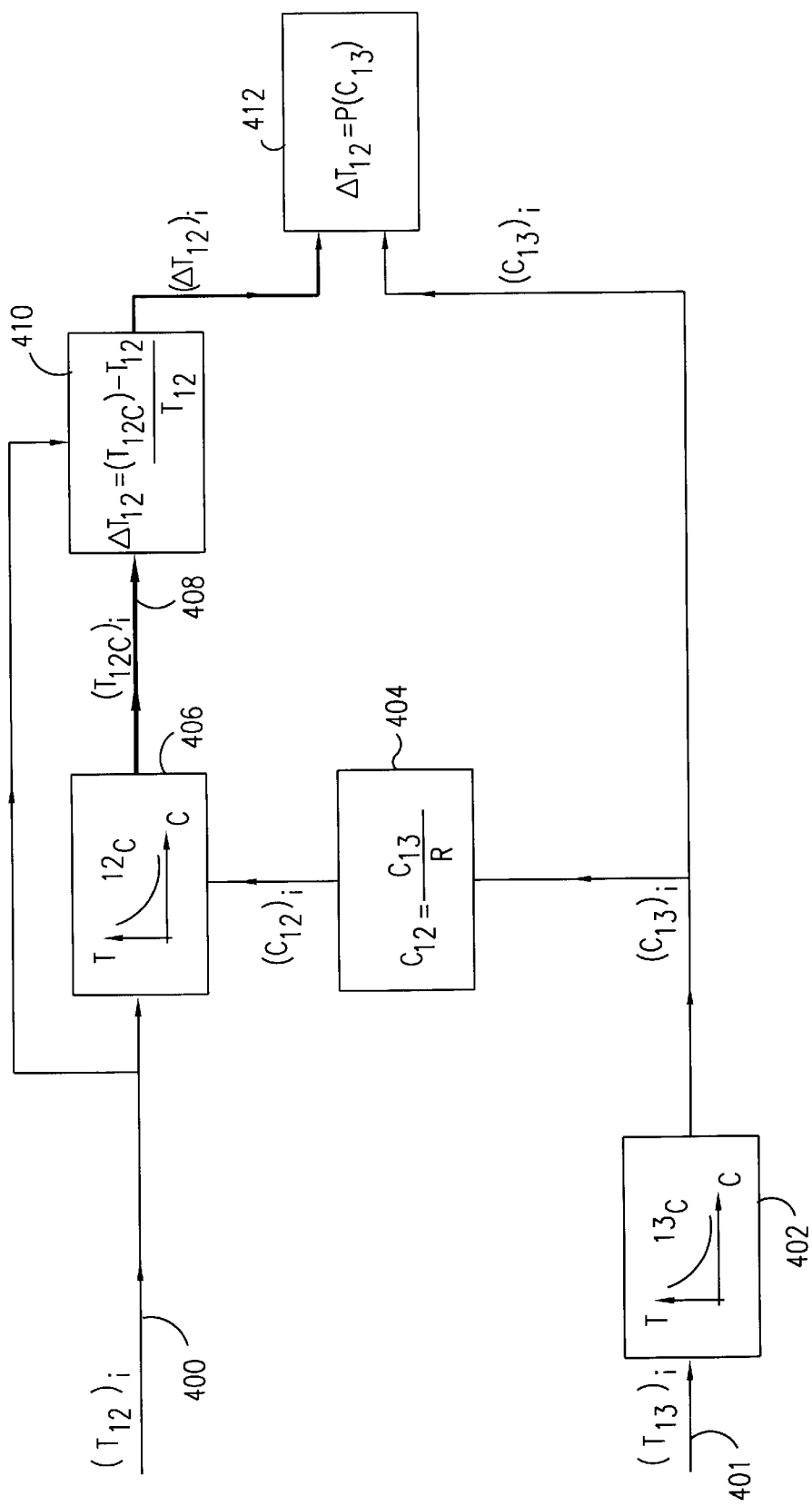
FIG. 22 is a schematic flow diagram of the main steps of a preferred embodiment of the calibration procedure operating in the breath tester.

Reference is now made to FIG. 22, which is a schematic flow diagram of the main steps of the calibration procedure. The input data for the procedure are a series of $^{12}CO_2$ transmittances $\{T_{12}\}i$ 400, and a series of $^{13}CO_2$ transmittances $\{T_{13}\}_i$ 401, known from measurements of different samples of the same gas, each sample having a different concentration $C_{12}$. Since all of these measurements come from the same gas sample, the isotopic ratio for all of the concentrations should be constant.

For each value of $T_{13}$, the value of the equivalent concentration $C_{13}$ is known by fitting the values $T_{13}$ to the given $C_{13}$ absorption curve $T_{13}=F_{13}(C_{13})$, as shown at step 402.

It is now assumed that within the operating range of $CO_2$ concentrations used, the absorption curves for both isotopes T(c) can be described with good accuracy by a single exponent of the form:

$$T(c)=y_0+A\exp(-c/t),$$

where T(c) is the transmission as a function of the concentration c, and $y_0$, A and t are the parameters which define the absorption curve.

Furthermore, it is found empirically that the $^{13}CO_2$ absorption curve is significantly more stable than the $^{13}CO_2$ absorption curve, and that its parameters $y_{13}$, $A_{13}$ and $t_{13}$ can be considered to be essentially independent of changes in environmental conditions. The $^{12}CO_2$ absorption curve is therefore regarded as a fixed function.

The calibration procedure consists of the following steps:
1. At 402, the measured $\{T_{13}\}_i$ values are inserted into the known $^{13}CO_2$ absorption curve, to obtain a series of $\{C_{13}\}_i$ values, where $C_{13}=F^{-1}_{13}(T_{13})$.
2. A series of the unknown $\{C_{12}\}_i$ can then be created at step 404, by using the isotopic ratio R, $C_{12}=C_{13}/R$. The value of R used can be approximated, without loss of effectiveness of the convergence of the calibration process used, by the natural isotopic ratio, $R=(C_{13}/C_{12})$natural.
3. At step 406, the new generated values of $\{C_{12}\}_i$ and the initial values of $\{T_{12}\}_i$, are used to determine new parameters $y_{12}$, $A_{12}$ and $t_{12}$, which more accurately characterize the current status of the $C_{12}$ absorption curve. This can be preferably done by means of a best fit calculation, such as the "minimum of mean squared error" method, as is well known in the art.
4. A series of corrected transmittance values $\{T_{12c}\}_i$ 408 are obtained by insertion of the new generated values for $\{C_{12}\}_i$ into the new $C_{12}$ absorption curve. As expected from the method by which these corrected transmittance values were calculated, a constant isotopic concentration ratio R, is now obtained, as required.
5. At step 410, the differences between the initial input transmittance values $\{T_{12}\}_i$ and the new corrected transmittance values $\{T_{12c}\}_i$ are calculated, and for each concentration $\{C_{12}\}_i$, a normalized error difference $\Delta T_{12}=(T_{12c}-T_{12})/T_{12}$ is obtained. A series of these values, $\{\Delta T_{12}\}_i$, is thus obtained.
6. At step 412, a best fit polynomial, $\Delta T_{12}P(C_{13})$ is generated, using the new values of $\{\Delta T_{12}\}_i$ and the known values of $\{C_{13}\}_i$. The order of the polynomial depends on the number of concentrations used as input data, and is typically of order 3 to 5.

The result of the above calibration procedure is that a new absorption curve is obtained for calculating the $C_{12}$ concentrations. Using this polynomial, each newly measured value of $T_{12}$ is therefore corrected to a more accurate value. The new correction function $\Delta T_{12}=P(C_{13})$, by virtue of the way in which it was derived, ensures that a zero delta value is obtained between samples of gas with different concentrations but with the same isotopic ratio.

According to another preferred embodiment of the calibration procedure, it is possible to use an abbreviated calculation method, wherein the value of the correction polynomial $P(C_{13})$ is changed directly, using the values of $C_{13}$ obtained from the $^{13}CO_2$ absorption curve, instead of generating a new $C_{12}$ absorption curve. According to this method, step 406 in FIG. 22 is by-passed, and the assumption is made that the $^{12}CO_2$ absorption curve too is fixed, like the $^{13}CO_2$ curve. The advantage of using the full calculation procedure, however, as described hereinabove, is that a clearer physical picture of what is changing can be obtained if the changes in the $C_{12}$ absorption curve are followed.

3.5.2 Soft Calibration Procedure

The Soft calibration differs from a full calibration in that only the correction polynomial function $\Delta T_{12}=P(C_{13})$ is optimized. The parameters of the absorption curves for $C_{13}$ and $C_{12}$ remain untouched.

This procedure requires the input of a historic series of $^{12}CO_2$ transmittances $\{T_{12}\}_i$ and $^{13}CO_2$ transmittances $\{T_{13}\}_i$ from tests with negative results, from samples taken either before the ingestion of the labeled substrate (baseline results) or after the subsidence of any oral activity. The transmittances are grouped by the test from which they were obtained.

The procedure includes steps similar to those used for the regular calibration described above, as follows:
1. Using the current $C_{13}$, $C_{12}$ absorption curves and the last known correction polynomial, the deltas and concentrations for the input transmittances are calculated, and the correlation between the $\{C_{13}\}_i$ concentrations and the deltas is determined.
2. A series of $\{C_{12c}\}_i$ is created by inserting the values of $\{C_{13}\}_i$ into the relationship $C_{12}=C_{13}/R$, where R is constant and can be set equal to the natural ratio.
3. The $C_{12}$ absorption curve and $\{C_{12c}\}_i$ are used to find a series of corrected transmittance values $\{T\,C_{12}\}_i$, where $T_{12c}=F_{12}(C_{12c})$. These are the transmittances needed in order to obtain a constant R ratio.
4. A series of normalized differences $\{\Delta T_{12}\}_i$ between the input transmittances $\{T_{12}\}_i$ and corrected transmittances $\{T_{12c}\}_i$ are created, where:

$$\Delta T_{12}=(T_{12c}-T_{12})/T_{12}$$

5. Using $\{\Delta T_{12}\}_i$ and $\{C_{13}\}_i$, a best fit polynomial $\Delta T_{12}=P(C_{13})$ is created, of order 3 to 5 depending on the number of concentrations used as input data.
6. Using the current $C_{13}$, $C_{12}$ absorption curves and the new correction polynomial, the new deltas and new concentrations are determined for the corrected input transmittances, and correlation between these new concentrations and new deltas is determined.
7. If, using the new $P(C_{13})$ correction polynomial, the correlation between the new concentrations and the new deltas is reduced, the old polynomial is replaced with new one.

If the soft calibration procedure was successful, the result is a lower value of correlation between deltas and concentrations. Since the soft calibration operates continuously, adding to the database every new set of negative data obtained, there is need to perform more than a single iterative calibration cycle. So long as the correlation is reduced, the use of the new correction polynomial ensures that the soft calibration is operating in the correct manner, and that the correlation errors continuously converge.

4. Input Capnograph Calibration

In addition to the above mentioned calibration tests of the accuracy of the overall instrument operation, a specific test for the calibration of the capnographic probe at the input to the instrument is also performed. The capnographic probe measures the input breath waveform so that those parts of the waveform which are to be collected or rejected can be correctly defined. Since a capnograph does not have the same high measurement accuracy as the breath tester, a procedure using the results of the breath test measurement, which are highly accurate, is used to calibrate the input capnograph.

The $CO_2$ capnographic probe at the entrance to the system provides a measure of the $CO_2$ concentration. The concentration of the content of the accumulated sample at the end of the filling process is estimated by integration of the capnographically measured concentrations of all of the breath waveform parts collected by the intermediate chamber system. The accuracy of this measurement is dependent on the form of the capnograph's absorption curve, which may have changed because of operating conditions. The concentration of the content of this accumulated sample is now measured in the gas analyzer sample chamber, where a highly accurate measure of the concentration is obtained. This is then used to correct the absorption curve of the capnograph for the actual environmental conditions existent in the system, by correcting the $CO_2$ probe calibration, so that the estimated bag concentration is made equal to the measured concentration.

Patient Preparation and Test Procedure

1. Patient Preparation

Prior to application of breath tests, during the patient history intake, it is advisable and is common practice that the physician should note details about any medications taken by the patient, which could interfere with the results of the test. In particular, the patient is typically asked according to the methods of the prior art, whether he has been taking any antibiotic or other therapeutic drug recently, since these drugs may affect the results of the breath test, depending on what specific breath test is being performed. Some of the prior art describes breath test methods which use two measurement points, based on a single bag of breath samples collected before ingestion, and a single bag thereafter, or at best, three measurement points, based on one sample bag before, and two sample bags collected at different times after substrate ingestion. Using these methods, in order to avoid the danger of false negative results, a time interval of a number of weeks is typically recommended between the cessation of the taking of antibiotic or other specific gastrointestinal therapeutic drugs and the execution of the breath test. For example, operating recommendations given by Alimenterics Inc., of Morris Plains, N.J., the manufacturers of the LARA (Laser Assisted Ratio Analyzer) system for the detection of *Helicobacter Pylori* the upper gastro-intestinal tract, suggest that the taking of antimicrobials, omeprazole (a proton pump inhibitor) and bismuth preparations within 4 weeks prior to performing their breath test, may lead to false negative results The reason for this recommended abstinence period is that the drug may significantly affect the physiological dynamics of the appearance of the isotope labeled component in the patient's exhaled breath, due to suppression of the bacteria responsible for the mechanism giving rise to the elevated isotopic ratio. According to such prior art methods, this may result in a misdiagnosed result, particularly a false negative result because of the reduced reaction level, or because of the delayed physiological response dynamics, and hence arises the need to question the reliability of breath tests performed within a specified time of such drug therapy.

According to preferred embodiments of the method of the present invention, the use of multi-sample, on-line, virtually continuous monitoring of the isotopic ratio in the exhaled breath described in the present application, as opposed to the prior art methods of measuring one, or at most two discrete samples following ingestion of the labeled substrate, enables most changes in the patient response to be more easily detected. Unlike the prior art methods, according to the preferred methods of the present invention, the breath test for *H. pylori* can thus be performed with an acceptable rate of specificity and sensitivity, even when the patient is currently undergoing PPI therapy for the treatment of gastric problems, or antibiotic or other treatment for the eradication of the *H. pylori* infestation. At worst, the knowledge that the subject has undergone such therapy in the period immediately preceding the test, can be used by the physician to assign a somewhat lower "Level of Confidence" parameter to the results, but need not lead to any effective change in their significance.

Furthermore, according to most of the recommended procedures according to prior art breath tests, the patient is advised to fast for a period typically of several hours before the breath test, to eliminate the effects of changes in isotopic ratio arising from particular food intake. It is known, for instance, that diets high in maize content result in a higher baseline $^{13}CO_2$ isotopic ratio than otherwise. Because of the short time required to perform the breath test according to the present invention, there is no need for the patient to fast prior to the test, since any changes in isotopic ratio resulting from particular food intake typically occur at a considerably slower rate than changes measured in the breath test due to *H. pylori* activity. This advantage may be enhanced by the ability of the present invention to monitor changes in the isotopic ratio measured virtually continuously, thus countering the effects of possible different dynamic response to the urea because of uncertainty as to the time from the patient's last food intake. In addition, there is evidence pointing to the fact that the ingestion of a meal results in the covering of part of the stomach lining, such that the *H. pylori* activity is reduced. Even if this is the situation, the ability of the present invention to virtually continuously monitor changes in the isotopic ratio enables more abstruse changes in isotopic ratios to be detected, and thus provides a higher level of confidence to the measurement than other prior art methods.

Reference is now made to FIGS. 23A–23E, which show situations which typically arise during the execution of breath tests, which, according to the prior art methods of discrete breath sample collection and analysis, may have been misdiagnosed as giving false positive or false negative results. The use of the virtually continuous methods of sampling and analysis according to further preferred embodiments of the present invention, enable these cases to be correctly diagnosed.

Figure 23A:
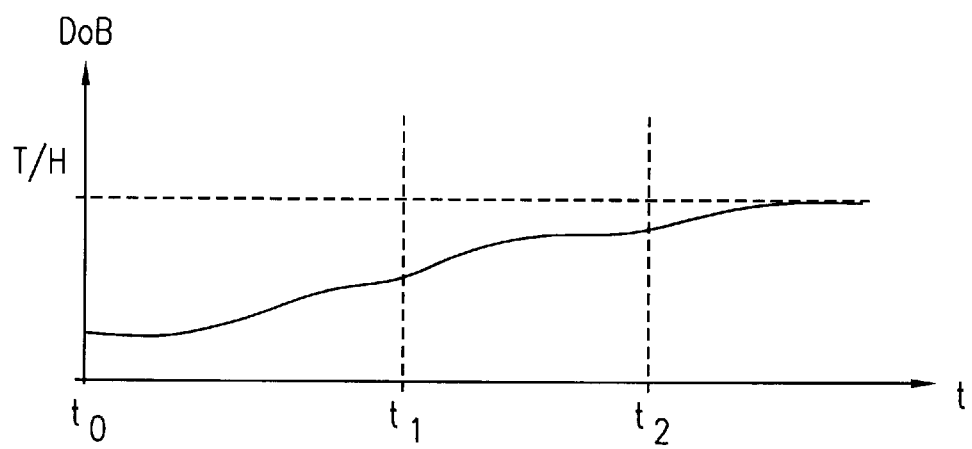
FIGS. 23A to 23E show plots of various breath test results which can be correctly interpreted using methods of virtually continuous sampling and analyzing according to preferred embodiments of the present invention, but which may have been misinterpreted using prior art methods of collecting and analyzing discrete bags of sample breath.

In FIG. 23A is shown a plot of an isotopic ratio which is increasing very slowly, but monotonically. This kind of response can arise when, for instance, the test is performed on a subject too soon after food intake. The absorption of the marked substrate from a full stomach is considerably slower than otherwise, and there is also a strong dilution effect from the other stomach contents. Consequently, even if the subject is definitely positive, the result may be a slow rise in the resulting isotopic ratio. The same effect may be seen in a subject with a poor level of gastric absorption, or in a subject undergoing drug therapy for treatment or eradication of the disease or bacteria being tested for.

According to the prior art methods of collecting a single or at most two sample bags at predefined times after ingestion of the marked substrate, at those times, $t_1$ and $t_2$, the isotopic ratio has not reached the upper threshold level, T/H, the crossing of which would be determined as indicating a positive result. As is seen, even a considerable time after $t_2$, the threshold level is still barely crossed, or may not have been crossed at all, long after the termination of the breath test according to all of the usually accepted protocols. This subject would thus have been determined to be negative.

According to the methods of the present invention, however, the ability of the breath tester to virtually constantly collect and monitor a plurality of breath samples, enables the analysis software of the breath tester to detect the continuous rise in isotopic ratio, and such a subject would thus be more correctly diagnosed as being positive. The use of this method therefore allows more reliable breath testing to be performed. Furthermore, it enables the breath tests to be performed more reliably without the need of pre-test fasting, and on subjects undergoing drug therapy for the treatment or eradication of the clinical state or bacteria being tested for. Furthermore, it allows a result to be obtained earlier than by the prior art, discrete sample bag methods.

Figure 23B:
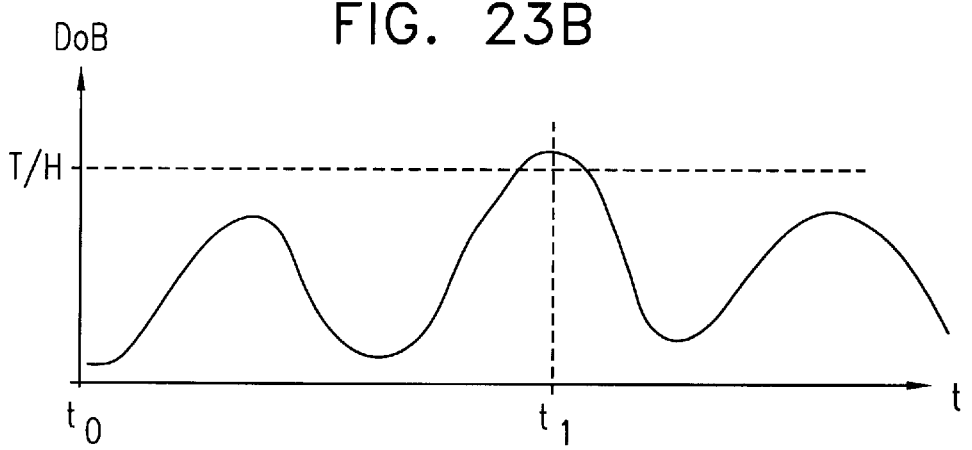

Reference is now made to FIG. 23B, which shows an example of the plot of a breath test of a subject who has a condition which results in an unstable level of metabolized substrate, and hence of isotopic ratio of his exhaled breaths, but who does not show the clinical symptoms of the condition being sought for in the breath test. According to some prior art methods, if a sample bag were, by chance, to be collected for analysis at point $t_1$ in time, the subject would be diagnosed as positive. Use of the methods according to the present invention, would however, result in a correct negative result, since no definite rising trend is detected.

Figure 23C:
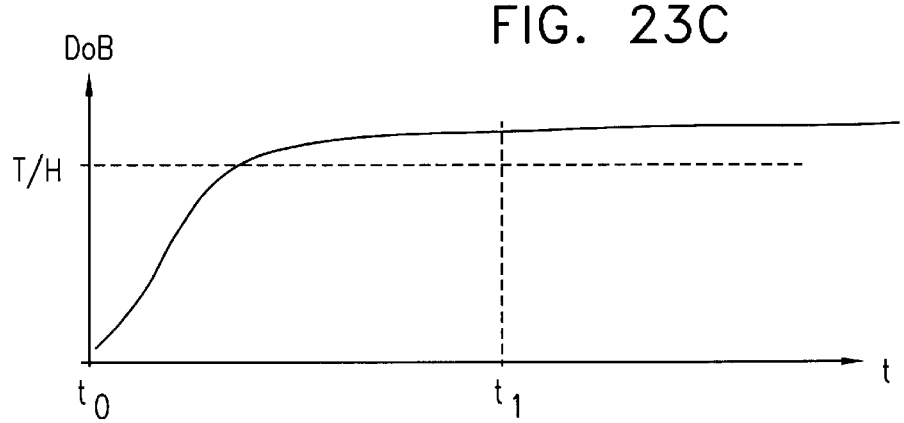

Reference is now made to FIG. 23C, which shows a situation in which the isotopic ratio rises fairly rapidly to over the threshold level T/H, but then reaches a steady plateau level just above the threshold. Such a physiological outcome would be determined as being positive according to a single point prior art test performed at point $t_1$, yet would be correctly interpreted as negative by the analysis methods used in the present invention.

Figure 23D:
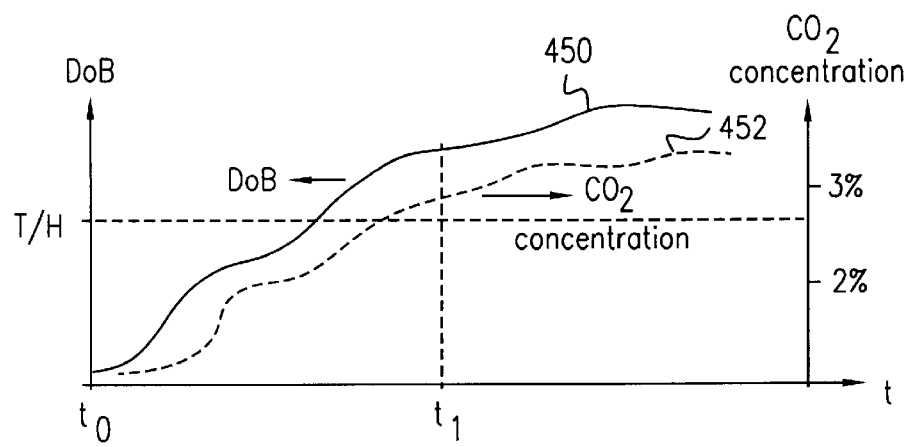

Finally, reference is made to FIG. 23D, which shows a plot 450 of the result of a breath test, which would initially be interpreted as giving a positive result, whether by a prior art discrete bag collection method, at time $t_1$, or by the methods of the present invention using virtually continuous collection and analysis of isotopic ratios. However, on the same graph are plotted the values 452 of the carbon dioxide concentration of the samples measured at each point in time on the graph. It is observed that the concentrations show a strong correlation with the ratios measured at each point in time.

Figure 23E:
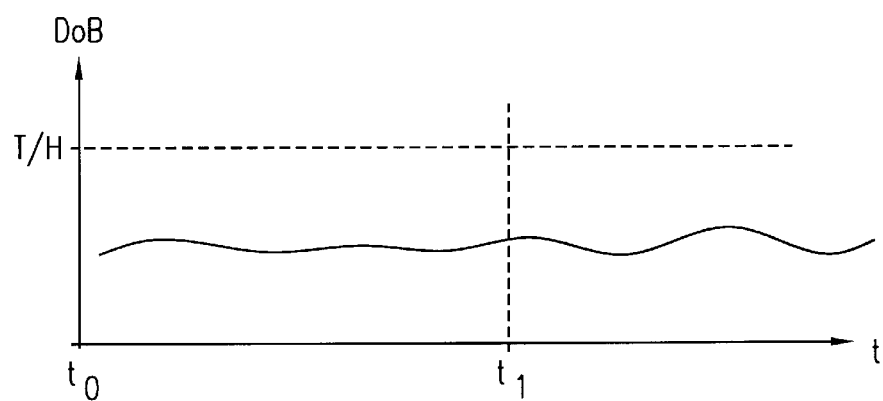

According to the methods of the present invention, the correlation of the concentrations with the isotopic ratios would be detected by one of the self diagnostic routines operating within the instrument, as arising from an incorrect calibration state of the gas analyzer, probably as a result of a shift in one of the absorption curves. A patient calibration procedure would then be performed, to correct the parameters of the absorption curves so as to reduce the correlation discovered, and the results of the test recalculated retroactively, using the original data with the newly calculated absorption curves. FIG. 23E shows the result of this recalculation procedure after the calibration. As is observed, the isotopic ratio is now seen to be low and undulating, and the result of the test is shown in fact to be negative.

2. Substrate Preparation and Administration

According to further preferred embodiments of the present invention, a procedure is practiced for the administration of the marker substrate. This is described in terms of the method used for the breath test for the detection of *H. pylori*, where urea is used as an isotopically labeled substrate. The current state of practice of this procedure is well documented in a number of recent published patent applications, such as WO 98/21579 to A. Becerro de Bengoa Vallejo, entitled "Method and kit for detecting *Helicobacter pylori*" and WO 96/14091 to C. Nystrom et al, entitled "Diagnostic preparation for detection of *Helicobacter pylori*" both hereby incorporated by reference, each in its entirety.

It is known in the art, such as in the above mentioned deBengoa Vallejo PCT Application, that in order to detect the activity of *H. pylori* in as efficient a manner as possible, the pH value of the stomach antrum should be maintained at its natural acidic level, in which environment the *H. pylori* continues its urease activity undisturbed. This can be preferably achieved by giving the patient before administration of the urea, a drink of approximately 200 ml of aqueous citric acid solution, with a pH of 2 to 2.5, instead of the water used in the earliest breath tests. In the article entitled "Citric Acid as the Test Meal for the $^{13}$C-Urea Breath Test" by D. Y. Graham et al., published in The American Journal of Gastroenterology, Vol. 94, pp. 1214–1217, May 1999, there is described the results of breath tests performed on patients after taking citric acid solutions. Results on positive patients were obtained significantly more quickly using 4 grams of citric acid than using only 1 gram or plain water. The use of citric acid has three more added known advantages—firstly citric acid delays gastric emptying, thereby keeping the full amount of urea in the stomach for a longer period, secondly, citric acid assists in counteracting the effects of on-going P.P.I. therapy, as given to a large number of candidates for the *H. pylori* detection breath test, and thirdly, citric acid diminishes the activity of oral bacteria, which are known to cause interference with the breath test.

The known procedure is, therefore, to give the patient a drink of approximately 200 ml of dilute citric acid, before or with the administration of the urea. Since the stability of urea in solution cannot always be guaranteed for long periods, the generally accepted procedure is to provide the urea in powder or tablet form, which is then dissolved in water, and given as a drink.

According to a preferred embodiment of the method of the present invention, the urea is provided in the form of a tablet, which is dissolved directly in the citric acid solution, which is then drunk, or taken by means of a straw. The use of a straw ensures that the urea has minimal contact with the oral cavity, such that the effect of oral bacteria is reduced. This procedure has a number of advantages. Firstly, the use of a pill rather than powder is simpler to package and use. Secondly, the use of a pill makes it clear that all of the urea has dissolved, and therefore, that the whole of the dose is active immediately on ingestion. Thirdly, for some tablet structures, the urea dissolves more readily in the citric acid solution than it does in water. For example, a tablet composed of 50% urea and 50% sodium chloride, with silicate binders and cellulose disintegration agents dissolve completely in a citric acid solution in almost half the time required for dissolution in water, 4 minutes as opposed to almost 8 minutes.

3. Kit Identification

The breath tester instrument according to the present invention can be used for a number of different tests, some of which are described in the "Background" section of this application, and even more in the PCT Publication No. WO 99/12471, mentioned in the background section. Each test uses its own specific kit of isotopically labeled substrate, and possible accompanying solution components, such as the urea and citric acid used in the breath test for the diagnosis of *Helicobacter Pylori* in the upper GI tract. Since each test procedure may also have its own specific test protocol, in terms of elapsed time and detection levels for the gas being detected, it is important that a means be provided for ensuring that the correct kit is being used for the selected breath test, and vice versa. Furthermore, the quantity of substrate and accompanying solvent used can be made dependent on the age, weight, medical history, or even ethnic or geographic origin of the patient, and the breath test parameters are adjusted accordingly. Finally, the pharmaceutical lifetimes of some of the active materials in the kits may be limited, so that it is important to warn the user, or even to disable the instrument, if an attempt is made to use a kit with an expired usage date.

According to a further preferred embodiment of the present invention, the materials for each individual breath test are supplied in a kit together with the disposable oral/nasal cannula or other breath conveyance tube used in performing the test. In the co-pending U.S. patent application Ser. No. 08/961013, "Fluid Analyzer with Tube Connector Verifier", by some of the inventors of the present application, and hereby incorporated by reference, there is disclosed a tube connection verifier, which is operative to ensure that the correct tube is being used for the test being performed by the analyzing instrument, and that the connector is attached correctly. According to this embodiment of the present invention, the connector of the oral/nasal cannula or equivalent, can be coded with an identification code which contains information about which materials are contained in the kit together with that cannula, their quantity, and their date of expiry. Means are provided on the connector of the breath tester instrument, to read the information thus provided when the oral/nasal cannula or equivalent is connected to the instrument. These means can include one or more of optical, electronic, magnetic or mechanical means, including bar code scanning, digital impulses or any similarly effective means. The communication can be either automatic when the connector of the cannula or equivalent is plugged into the breath tester, the data being automatically input to the instrument, or it can be actuated in an interrogation mode when the operator keys into the instrument the test details.

Alternatively and preferably, a tracer or marker material is added to the materials in the breath test kit, and means are provided in the instrument for detecting the marker. According to this preferred embodiment, any of the contents, quantity and expiry date of the breath test material can be automatically identified by the breath test instrument, even if use is not made of a cannula with the relevant coded material information, such as those provided in the kit.

According to a further preferred embodiment of the present invention, a marker added to the substrate in the breath test kit can be used to initiate the analysis of the breaths collected. According to this embodiment, a substance such as labeled glucose is added to the substrate, the substance being very rapidly absorbed by the stomach into the blood stream, and its metabolic by-products appearing very shortly thereafter in the subject's exhaled breath. The detection by the instrument of the labeled marker by-product from the glucose can be used as a signal that the substrate has been ingested, that its absorption in the stomach has commenced, and that it has followed the complete metabolic pathway of the physiological effect being investigated, but being immune to the particular disease, bacteria or physiological malfunction being sought, appears independently of the presence of that disease or malfunction. This signal is used to issue a command to the instrument control system to commence analysis of collected breath samples for the specific by-product of the test being performed. The use of this method is particularly advantageous with breath tests which extend over a long time, since the marker provides a signal as to when to expect the commencement of the appearance of the substrate by-products.

According to other preferred embodiments of the present invention, as an alternative to a solid such as glucose, a gas can be incorporated into the substrate, the gas being released on dissolution of the substrate in the gastric juices, and detected directly in the breath without the need to perform the complete circuit of absorption, metabolism and pulmonary exhalation. As an alternative, the gas can be produced from a parent material which generates the marker gas on contact with the gastric acids.

In all of these embodiments employing marker materials, whether incorporating a gas, or resulting in a direct or an indirect gaseous by-product, if the gas is identical to the gas to be detected in the specific breath test, it is important that the effects of the marker gas be short term, so as not to interfere with the detection of the true by-products of the breath test.

Analysis of Breath Test Results

In the above-mentioned PCT Publication No. WO99/12471, entitled "Breath Test Analyzer", by some of the inventors in the present application, there is disclosed a method whereby the breath test is terminated at a time determined by the results of the test itself. This is similar to the method disclosed hereinabove, whereby the method of virtually continuous collection and analysis of breath samples enables the instrument to determine that a clinically significant outcome has been obtained in accordance with the ongoing results of the test, such that the outcome of the test can be obtained earlier than by means of a sampling method using only a single or two discrete sampling points, as in most of the prior art. According to a further embodiment of the present invention, the breath test instrument is equipped with signaling means for indicating to the operator that the test may be concluded, since a clinically significant result has been obtained. The signal may preferably and alternatively be visual, by means of one or more indicator lights, or audible, by means of tones, or by any other suitable real time indicating method or device. In FIG. 15, are shown on the front panel of the breath test instrument 210, two alternative embodiments for signaling to the operator that a meaningful result has been obtained, one in the form of an indicator lamp 231 and the other a loudspeaker 233. According to a further embodiment of the present invention, different signals may be used for indicating different outcomes of the test, such as different colored light outputs, or different tones, for indicating whether the outcome of the test is positive or negative.

According to further preferred embodiments of the present invention, there are provided a number of methods used in calculating the results of the gas analyses, such that a decision about the results of the breath test are obtained at an earlier time, or with more certainty than by prior art methods.

(a) Oral Activity Determination

One of the advantages of the virtually continuous analyzing of samples, according to the present invention, is that it becomes possible to differentiate between the effects of oral bacterial activity, arising from the direct effect on the substrate of bacteria in the oral, nasal or laryngetic passages, and true gastric effects. When only a single, or at most, a two point measurement after substrate ingestion is made, as in most of the prior art methods, it may be difficult to determine with certainty whether an elevated isotopic $CO_2$ ratio is due to a rise in the isotopic $CO_2$ ratio from a gastric interaction, or whether it is the fall of the isotopic $CO_2$ ratio from the tail-end of oral activity. This may result in a percentage of false positive results.

With the effectively continuous monitoring of the isotopic ratio according to the present invention, a method of calculation can be used which determines whether the isotopic ratio is on a rising or a falling trend, thus discriminating between a true positive gastric result, and the fall-off of oral activity. The method involves plotting the results from the commencement of the test, such that the detection of the characteristic rise and fall of oral activity is completely clear. According to a preferred embodiment of the present invention, a response is regarded as resulting from oral activity, and is therefore ignored, if a characteristic peak of the DoB is detected, in the form of a rising and falling value, exceeding a lower threshold value, and returning to below it, all within a time which is clearly less than the time taken to detect the effects of the true physiological effect being sought after in the breath test. For the breath test for H.Pylori, a typical time frame for the completion of any oral activity is of the order of 8 minutes from ingestion of the labeled substrate. Typical values of the oral activity peak are a rise to about $10\delta$, together with a consequent fall of at least $5\delta$ from the peak value, all within a time of 4 to 8 minutes from the ingestion of the urea.

It should be pointed out that the term "oral activity" is used in this specification to include any physiological side effects which result in an increased isotopic ratio in the subject's exhaled breath unrelated to the sought-after effect being investigated by the breath test, or without traversing the metabolic path involved in the physiological state being investigated.

(b) Isotopic Ratio Change

In the order to determine the increase in the isotopic ratio $^{13}CO_2/^{12}CO_2$ of carbon dioxide in the subject's exhaled breath, the generally accepted method is to measure a baseline level of the background isotope ratio in the subject's breath before administration of any substrate. The fractional increase in isotopic ratio above this baseline is expressed in terms of the known "Delta over Baseline" parameter, or DoB. In generally used prior art methods, the DoB is commonly expressed as a normalized parameter, delta $\delta$, or more strictly, delta per mil, where the delta between the isotopic ratio $R_1$ of a sample 1 and a reference sample $R_R$ is defined as:

$$\delta_1 = 1000 * (R_1 - R_R)/R_R$$

The reference sample traditionally used is a geological rock standard known as Pee Dee Belemnite limestone, and the reference isotopic ratio $R_{pdb}$ is thus the isotopic ratio of carbon, $^{13}C/^{12}C$, as found in naturally occurring PDB limestone, and has the value 1.11273%.

The Delta over Baseline between measurements 1 and 2 is thus given by:

$$DoB = \delta_1 - \delta_2,$$

where, $$\delta_1 = 1000 * (R_1 - R_{pdb})/R_{pdb}$$

$$\delta_2 = 1000 * (R_2 - R_{pdb})/R_{pdb}.$$

Therefore, $$DoB = 1000 * (R_1 - R_2)/R_{pdb},$$

where:

$R_1$ is the isotopic ratio measured on sample 1 at time 1, and $R_2$ is the isotopic ratio measured on sample 2 at time 2.

In normal subjects, the isotopic ratio of baseline breath samples is essentially that of the carbon dioxide resulting from the metabolism of organic compounds originating in the vegetable-originated or animal-originated food consumed by the subject. Since these foodstuffs generally have an isotopic carbon ratio noticeably lower than that typical of naturally occurring carbon dioxide in the air, and also lower than that of PDB, the baseline isotopic ratio of exhaled breath in normal subjects is usually significantly less than $R_{pdb}$, by an amount which can range from somewhat over $15\delta$ to about $27\delta$, depending on the subject. The DoB, according to the generally used definition, is therefore expressed as the fractional difference in isotopic ratio between two measurements, relative to a specific fixed ratio, which is generally somewhat elevated from the typical baseline ratio.

According to another preferred embodiment of the present invention, it is possible in some cases to use the fractional difference in isotopic ratio between any two measurements, relative to a specific fixed ratio, but without the need to have made a baseline measurement. According to this embodiment, since the measurement of change in isotopic ratio is sufficiently sensitive, measurements taken following ingestion of the substrate may be sufficient to detect a sought-after change in isotopic ratio, without knowledge of the baseline level. It is then important to note that when using the various parameters mentioned in this section, and throughout this disclosure, for making calculations of the isotopic ratio change, the term "Delta over Baseline" is to be interpreted broadly to mean the difference in Delta over some previously measured value, without strict adherence to knowledge of the baseline level.

During measurement of isotopic ratios in breath samples, by whatever means, the conditions of measurement in the sample and reference cells can change from those for the correctly calibrated conditions. Some types of breath test, such as fat mal-absorption estimation, gastric emptying rate, or liver finction tests, may extend over a considerable period of time, even running into hours. In such cases, even very slight drift of the instrument during that time may become very significant. Therefore, if there is a systematic error in the measurement of the ratios, due for instance, to incorrect calibration arising from a shift of the gas absorption curves, even though the error in measurement of the change in two ratios close to each other is very small, the value of DoB calculated contains the full systematic error, since each ratio is normalized to a fixed value, $R_{pdb}$, whose value could be quite different from the ratios currently being measured.

In order to avoid this disadvantage, an alternatively defined $\delta'$ has been proposed in Publication No. WO 97/14029, of the PCT application by the Otsuka Pharmaceutical Co., where, for the ratios R between samples 0 and 1:

$$\delta'_1 = 1000 * (R_1 - R_0)/R_0.$$

This definition of $\delta'$ has $R_0$ in the denominator, instead of $R_{pdb}$. The difference between $R_0$, the baseline ratio, and $R_1$, the next point of measurement, is generally much smaller than that between $R_0$ and $R_{pdb}$, as explained above. The value of $\delta'$ is, therefore, much less susceptible to changes in measurement conditions resulting from a shift of the absorption curve, than the value of δ, since δ' is normalized with respect to a ratio $R_0$ close to the ratio $R_1$ being measured. By using this δ', some prior art measurement methods attempt to overcome the problem of the need to compensate for drift in the absorption curves.

On the other hand, since the value of δ' is dependent on the value of $R_0$, the absolute results are dependent on the baseline of the specific subject measured, and can thus vary with such factors as the diet of the subject, or the time elapsed since his last meal, or even his geographic origin, which it is known, can have an effect on baseline level. The difference in baseline levels between different subjects can cover a range of about 10δ, as mentioned above. For this reason, use of a δ' dependent on $R_0$ does not enable absolute numerical comparisons to be made between the results obtained from different subjects.

Reference is now made to Table 1 below, which shows several calculated values of the DoB normalized to $R_0$ in column 2, compared to the traditional DoB normalized to $R_{pdb}$ in column 3. Column 1 is the true isotopic ratio, as measured by mass spectrometry. The parameter RCIR will be explained hereinbelow. It can be seen that as the isotopic ratio of the sample increases, the DoB normalized to Ro diverges from the traditional DoB value normalized to $R_{pdb}$. Though the level of divergence shown at very large isotopic ratios has little clinically significance for a particular test, in statistical studies requiring comparisons of the results of breath tests on a number of different subjects, or for comparison of one subject's results taken at time intervals of typically some weeks, during which time his baseline ratio could be have changed significantly, the difference between the DoB parameters could become relevant, and the classical DoB, referred to $R_{pdb}$, is thus to be preferred.

TABLE 1

| Isotopic ratio | DoB normalized to $R_0$ | DoB normalized to $R_{pdb}$ | RCIR |
| --- | --- | --- | --- |
| 1.097 | 0 | 0 | 0 |
| 1.101 | 3.436 | 3.355 | 3.425 |
| 1.127 | 27.656 | 27.000 | 26.992 |
| 1.165 | 62.139 | 60.666 | 59.458 |
| 1.200 | 93.532 | 91.314 | 88.166 |

In order to overcome the dependence of the measured breath test results on changes in the absorption curves, according to the present invention, the breath test instrument may incorporate various compensation procedures, such as the soft-calibration, self-calibration or patient-calibration procedures, as described hereinabove. When one of these calibration procedures is performed, using for instance, a sample of the breath of a patient not showing meaningful change in isotopic ratio (a "negative" patient), the assumption is made in the calibration method that the isotopic ratio of that breath can be approximated by $R_{pdb}$. The parameters of the absorption curve are adjusted by the iterative calibration procedure, and as expected, the ratio measured is indeed found to be that of $R_{pdb}$. The use of such an assumed approximation to $R_{pdb}$, even though it is known that the true ratio may be 20δ or more below the value of $R_{pdb}$, has only a small effect on the DoB values measured. Thus, for example, if the true ratio of the above mentioned negative patient sample is, in fact, R=1.07% (a typical value for a negative patient), instead of the assumed $R_{pdb}$=1.11273%, then the error in the DoB measured resulting from the use of the $R_{pdb}$ approximation, is only of the order of 3% of the value measured. This means that instead of 5δ, a reading of 5.15δ is obtained, this deviation being quite insignificant. The absolute values of DoB measured thus have minimal dependence on the baseline level of the subject.

Taking the example, at the other extreme, of a subject with an unusually high baseline ratio, even with a baseline ratio as much as 60δ above the assumed value of $R_{pdb}$, by virtue of the iterative calibration method used, the measured DoB values obtained are affected by less than 1δ. Since the spread in baseline isotopic ratio between different subjects is typically considerably below this value of 60δ, the use of the preferred calibration methods of this invention, as described hereinabove, enable accurate breath test results to be obtained, referable to the generally accepted DoB parameter, and independent of the actual baseline of the patient tested.

Even the small deviations in the measured values of the DoB's engendered by the $R_{pdb}$ approximation used in the calibration methods described above, can be compensated for by executing a ratio measurement on a sample with a known isotopic ratio, such as by the execution of a calibration check of the instrument.

According to another preferred embodiment of the present invention, the above-amended definition for δ' is used in an alternative parameter, known as the "Relative Change in the Isotopic Ratio" or RCIR. The parameter RCIR can be preferentially used, instead of the prior art DoB, for determining the increase in the isotopic ratio of exhaled breath. The RCIR parameter is defined by means of the expression:

$$RCIR_n = RCIR_{n-1} + 1000*(R_n - R_{n-1})/R_{n-1},$$

where $R_n$ is the $^{13}CO_2/^{12}CO_2$ isotopic ratio for the measurement n. By definition, at the baseline measurement, $RCIR_0 = 0$.

According to the above definition of RCIR, the normalization is performed with respect to the isotopic ratio at the previous point measured, $R_{n-1}$. An alternative definition can also be used for RCIR, namely:

$$RCIR_n(+) = RCIR_{n-1} + 1000*(R_n - R_{n-1})/R_n,$$

where the normalization is done with respect to the ratio at the current measurement point. Since, during the course of a breath test showing a positive result, $R_n > R_{n-1}$, the results achieved using $RCIR_n(+)$ are closer to those obtained relative to $R_{pdb}$, than results obtained using the previously defined $RCIR_n$.

According to a further preferred embodiment of the present invention, these two types of normalization for RCIR, are used alternately for calculating the results of each measurement, depending on whether the measured isotopic ratio is on the increase or decrease. When the isotopic ratio is rising, $R_{n-1} < R_n$, and the second definition, RCIR (+), is used. For a falling isotopic ratio, in which case $R_n < R_{n-1}$, the first definition, $RCIR_n$, is used. This method of calculation, using alternate RCIR parameters, is advantageous for smoothing the trend of the results when the ratio curve changes direction from increasing to decreasing, or vice versa, or when there is a high level of noise in the measured points, whether from instrumental or physiological sources. The method is also advantageous for compensating for a measured point which is particularly deviant from the general trend of the plotted curve.

A further advantage of the use of RCIR parameters alternately defined according to the trend in direction of the isotopic ratio measured, lies in the accuracy of the results obtained. The use of a single definition RCIR parameter results in either the accentuation or the de-emphasis of the change in the ratio, depending on the direction of the change. Thus, for instance, the use of the first $RCIR_n$ parameter, being normalized to the previous reading $R_{n-1}$, results in the exaggeration of an increasing ratio, since when on the increase, the $R_{n-1}$ in the denominator of RCIR is smaller than $R_n$. Similarly, the use of $RCIR_n$ results in an apparent decrease in the rate of decrease of a falling ratio, since the denominator $R_{n-1}$ is now larger than the present ratio $R_n$. The opposite effect is obtained when using the RCIR(+) parameter, de-emphasizing an increase, and exaggerating a decrease.

As a consequence, if either one or the other of the RCIR parameters are used in the analysis of an executed breath test, an undulating ratio curve will result in an accumulated ratio error. On the other hand, according to the preferred embodiment of the present invention whereby alternate RCIR parameters are used, depending on the trend in the measurements, an undulating curve always reflects the true measured result, and, as a result, for instance, always returns to its original level if the ratio returns to its original value.

Instrumental drift which takes place during the course of a measurement, does not affect the parameter RCIR significantly differently from the affect on the prior art DoB. In the last column of Table I above, are shown values of the RCIR parameter calculated for each isotopic value given. As is seen, the RCIR values follow the values of the classical DoB, with small deviations at high DoB values.

According to another preferred embodiment of the present invention, the RCIR can be used in a method of measurement which largely overcomes a major problem of performing breath tests over comparatively long periods of time, such as those tests mentioned above, which can extend for well over an hour. In such situations, instrumental drifts are common, for example due to changes occurring in the absorption curves with changes in environmental conditions, in particular with change in temperature. In this situation, if a baseline reference is taken near the start of the test, there is no simple way of accurately comparing this baseline measurement with isotopic ratios obtained much later in the test, since the measurement conditions are generally likely to have changed, and the comparison is not therefore valid.

Furthermore, there are optical spectrometric gas analysis methods, including some used in breath tests, in which there is a need to bring the samples to be measured to the same major isotopic component concentration as the baseline sample, so that it becomes possible to directly relate optical transmissions (or absorptions) measured in the sample cells, to the concentrations of the component gases therein. This equality of concentration is achieved by diluting each sample collected, by means of an inert gas, down to a predetermined concentration. The concentration typically chosen is such that it is at the low end of the range of commonly achieved concentrations to be tested, such that a majority of the samples collected in practice, can be diluted down to that same predetermined concentration value.

In the above mentioned Publication No. WO 97/14029, of the PCT application by the Otsuka Pharmaceutical Co., in order to achieve equality in concentration between two samples, a method is described of comparing the concentration of the two sample bags, and diluting the higher concentration one to that of the lower. Unfortunately, it is impractical to apply the method of diluting to the lowest concentration to a large number of samples, each collected in a different sample bag or to an on-line measurement method in which the breath of the subject is effectively monitored quasi-continuously, as is described in the present invention. The comparison of such a large set of samples would require a complicated system of sample handing and temporary storage, since each sample needs to be ultimately compared with every other sample.

Furthermore, since stable measurement conditions generally cannot be maintained during the duration of typical breath tests, as explained above, there is another disadvantage in the method of Otsuka, because of the use of the ratio, $R_0$, to which the changes in isotopic ratio of the samples are referred, which may be remote from the ratio of the measured samples. Likewise, if when comparing the n-th sample to sample n−1, the ratio $R_{n-1}$ is used for normalizing, the trend of the results becomes unduly exaggerated, and any changes over emphasized.

The utilization of alternating RCIR parameters, according to the preferred embodiments described in this invention, largely solves the above-mentioned deficiencies in the Otsuka method, enabling individual pairs of samples, n−1 and n, to be brought to the same concentration, without reference to any other of the pairs. Thereafter, the n+1 sample is measured relative to the new measurement of the n sample, and so on.

Another method of achieving the correct dilution of the samples, commonly used in prior art carbon dioxide breath tests, is by means of a comparison of the $^{12}CO_2$ IR transmission with a reference sample of known concentration. Since for the reasons stated above, comparative absorption measurements may be inaccurate if made at widely differing times, the ability to achieve samples of equal concentration is also affected by those same instrumental stability problems that affect the absorption measurements themselves. Thus, according to methods used hereto, when the samples may have been collected and measured at considerably different times, the accuracy of a breath test is dependent in two separate ways on the ability to perform accurate comparative absorption measurements referred to a baseline sample; firstly, in the ability to dilute the samples accurately to the same concentration, and secondly, in the ability to perform the actual absorption measurement accurately.

There are a number of methods of overcoming this problem. One method is to collect a very large baseline sample, and to divide it into separate individual parts that will suffice to compare each subsequent sample collected as the test progresses, with a part of the original baseline sample, under the conditions prevalent when the subsequent sample is measured, such that the comparison is more accurate. Alternatively, separate samples of the initial baseline sample can be drawn off for each successive breath comparison. These methods are very cumbersome to execute, and generally not easily feasible, because of the practical problem of collecting a large initial baseline sample that will suffice, after division, for each comparative measurement.

An alternative and simpler procedure that has been proposed in U.S. Pat. No. 5,146,294 to R. Grisar et al., is to use a storage container for supplying successive samples of a reference gas, which, between measurements of diluted breath samples, is transferred into the measurement chamber under conditions identical, as far as is possible, to those of the diluted sample breaths. The accuracy of this method would appear to be limited by the accuracy with which the system can be temperature stabilized, and by the accuracy with which the reference samples can be repeatedly measured at the same pressure conditions.

According to another preferred embodiment of the present invention, an alternative reference measurement method is to collect a single initial baseline sample of exhaled breath, and to repeatedly measure this same baseline sample immediately before and/or after measurement of each sample collected during the test, by transporting the baseline sample into and out of the measurement cell between each collected sample measurement. In this way, the baseline sample is measured under conditions similar to those of the collected samples. The execution of this method requires an accurate gas handling system to avoid contamination of the single baseline sample by loss, leakage or dilution.

Alternatively, and even more simply, this single baseline sample may be stored in its own reference cell, and compared with the sample gas in the measurement cell at each measurement of a new collected sample. This has the disadvantage of having to switch the measurement path between different cells in order to perform each measurement.

Calculation methods for performing all of the above procedures can be established using various different definitions of the change in isotope ratio from a fixed point, normalized either to an absolute fixed ratio or to a variable ratio. The isotopic deviation of any measured ratio is then given by any of the following expressions, depending on which reference ratio is used:

$$(R_n - R_{O(n)}) * 1000/R_{O(n)}, \quad (a)$$

or $$(R_n - R_{O(n)}) * 1000/R_{pdb} \quad (b)$$

where $R_n$ and $R_{O(n)}$ are the measured isotopic ratio and the baseline reference respectively measured at the $n^{th}$ measurement point.

When an absolute normalized measurement, such as that to $R_{pdb}$, cannot be achieved, for instance because of excessive instrumental drift, the relative isotopic deviation may then take the form:

$$(R_n - R_{O(n)}) * 1000/R_n \quad (c)$$

Since $R_n \geq R_{O(n)}$, expression (c) is closer to the standard PDB related expression (b), than (a) is.

When the reference ratio is not a baseline measurement, the change in isotopic ratio from this point can be calculated relative to the previous result. Thus, the deviation is obtained by subtracting for the previous result, one of the following terms, depending on the definition used:

$$(R_n - R_{ref(n)}) * 1000/R_{ref(n)}, \quad (d)$$

or $$(R_n - R_{ref(n)}) * 1000/R_{pdb}, \quad (e)$$

Where $R_n$ and $R_{ref(n)}$ are the measured ratio itself and reference ratio respectively measured at the $n^{th}$ measurement point.

When an absolute normalized measurement, such as that to $R_{pdb}$, cannot be achieved, for instance because of excessive instrumental drift, the relative isotopic deviation may then take the form:

$$(R_n - R_{ref(n)}) * 1000/R_n \quad (f)$$

Since $R_n \geq R_{O(n)}$, expression (f) is closer to the standard PDB referred expression (e), than (d) is.

For the first point (baseline), the relative change in isotopic ratio can thus be expressed as:

$$(R_0 - R_{ref(0)}) * 1000/R_{ref(0), \, pdb \text{ or } 0}$$

while for the $n^{th}$ measurement point, it is:

$$(R_n - R_{ref(n)}) * 1000/R_{ref(n), \, pdb \text{ or } n} - (R_0 - R_{ref(0)}) * 1000/R_{ref(0), \, pdb \text{ or } 0}$$

if the measurement is performed relative to a baseline, or:

$$(R_n - R_{ref(n)}) * 1000/R_{ref(n), \, pdb \text{ or } n} - (R_{n-1} - R_{ref(n-1)}) * 1000/R_{ref(n-1), \, pdb \text{ or } n-1}$$

if the RCIR calculation method is used.

According to another preferred embodiment of the present invention, a method is proposed, using the RCIR parameters, which largely overcomes the above-mentioned problems of comparing collected samples with a single baseline sample for breath tests which extend over a long period of time. According to this preferred method, a pair of samples is collected at each measurement point, except the first, where only one sample need be collected, generally a baseline sample. At any successive measurement point, n, one of the pair of samples collected is compared with one of the samples from the (n-1) point, generally collected a comparatively short time previously, while the second is kept for comparison with one of the pair of samples to be collected at the next measurement point, (n+1). At the last measurement point, two samples are collected, but only one need be measured, as the test is terminated at that point.

Though the method of this embodiment has been described in terms of the "collection" of two separate samples at each measurement point, it is to be understood that in practice, there is no need to physically collect two separate samples. It is possible, for instance to collect a single sample, and to use half at each of the two measurement points concerned, or to collect a single sample and to measure it twice, once at each measurement point, or any other suitable variation of the method.

The time between measurement points is comparatively short compared with the total elapsed time of the complete breath test, and can typically range from considerably less than a minute, to over 30 minutes, depending on the type of test being performed. It is thus simpler to maintain the integrity of the sample and the stability of the measurement conditions for the comparatively short period between one measurement point and the next, than from the beginning of the breath test till its end.

In this way, a moving frame of reference is created, whereby comparisons with the previous measurement point are always made under the closest possible measurement conditions, and each measurement point may be referenced back to the previous point, regardless of how the measurement conditions have changed in the interim because of instrumental drift.

Figure 24:
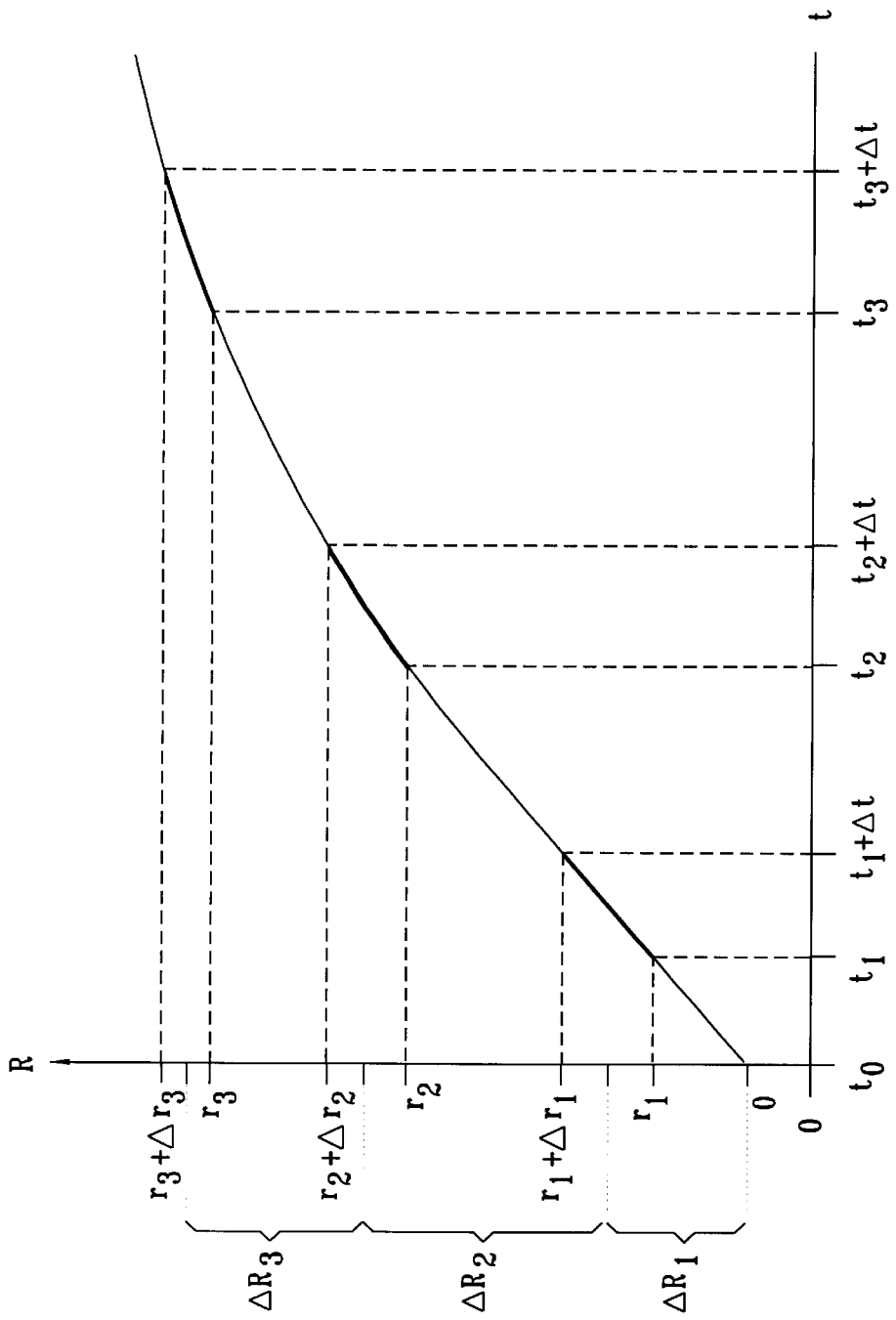
FIG. 24 is a graphic plot illustrating the use of the method of comparing pairs of successively collected sample with each other, rather than with baseline or reference samples.

The computational procedure of comparison of pairs of samples according to this embodiment of the present invention, can be understood by reference to FIG. 24, which shows a typical plot of how a measured isotopic ratio, R, could change as a function of elapsed time, because of instrumental drift, such as results from changes in the absorption curves. The graph shown is for illustrative purposes only. The plot shows the change in the ratio actually measured by the instrument for an idealized fixed ratio, as if the breath test were giving a negative result, with no change whatsoever in the true isotopic ratio. A similar explanation can be given for the more likely situation when the ratio really is changing, but for the sake of simplicity, a fixed ratio is used to explain the method of this embodiment.

Using the prior art methods of comparing the change in isotopic ratio to a baseline reference measurement taken at time $t_0$, the change in isotopic ratio measured at time $t_1$ would be $\Delta R_1$. At the next measurement point, taken at time $t_2$, the change in measured isotopic ratio, as a result of drift in the instrument, would be measured as $\Delta R_2$, and the accumulated change from the baseline level $\Delta R_1 + \Delta R_2$. Similarly, at the third measurement point $t_3$, the measured change in ratio from the previous point is $\Delta R_3$, and the accumulated change from the baseline level $\Delta R_1 + \Delta R_2 + \Delta R_3$. As is seen from the graph, the various values of $\Delta R_n$ can be significant, and the accumulated ΔR even more so, especially for breath tests which continue for a considerable time in comparison to the stability level of the instrument.

According to this preferred embodiment of the present invention, the collection of pairs of samples at each measurement point can reduce this error substantially. Thus, for instance, at time $t_1$, one of the pair of samples collected is used for comparing the ratio measurement at time $t_1$ with the baseline reference sample measured at time $t_0$. The second sample of the pair is kept intact until time $t_2$, and is then used as the reference sample against which one of the pairs of samples collected at time $t_2$ is compared. In this way, the change in measured ratio $\Delta R_2$ due to instrumental drift is nullified, since a sample from time $t_1$ is compared in the instrument with a sample from time $t_2$ under essentially identical conditions, namely those extant in the instrument at time $t_2$. Similarly, comparison of the second sample kept from $t_2$ with one from time $t_3$ enables the apparent shift in ratio $\Delta R_3$ to be effectively nullified. A similar argument applies for all successive measurement points in the breath test.

The above explanation is somewhat simplified in that it assumes that the ratio measurement of each sample takes infinitesimal time, and that both samples are measured simultaneously at each point in time, and thus under identical conditions. In practice, each ratio measurement takes a time $\Delta t$, and at point 2, for instance, the measurement of the ratio of the reference sample kept from time $t_1$ is performed at a time $\Delta t$ earlier than that of one of the pair of samples collected at time $t_2$. During that time $\Delta t$, the drift of the instrument continues, and the result is that the ratio $r_2$ measured at time $t_2$, is different from the ratio measured at time $(t_2+\Delta t)$ by an amount $\Delta r$. However, since the time $\Delta t$ taken for the ratio measurements themselves is generally significantly shorter than the elapsed time between successive measurement points, the use of the sample pair measurement method, according to this preferred embodiment of the present invention, still results in considerably increased accuracy, and considerably increased immunity from instrumental drift.

Furthermore, the sample pair method according to the present invention still results in a significant measurement improvement, even when account is taken of the time taken to dilute each sample down to its target concentration and to measure the concentrations reached, this process being performed so that the samples are compared at identical concentrations. The dilution and concentration measurement process may, in fact, take considerably longer than the time, $\Delta t$, taken to perform the ratio measurement itself. If the dilution and concentration measurement procedure is performed in the interim period between measurement points, both for the reference sample collected from the previous measurement point, and for the sample currently being measured, then when the time to make a ratio measurement arrives, the samples are already diluted to their target concentration, and are ready to be measured immediately, with a time difference between comparative measurements of no more than $\Delta t$.

This preferred method of collection and measurement of pairs of samples, and use of the RCIR parameter for calculation of the relative change in isotopic ratio of the samples, may be advantageous and applicable for all types of breath tests, both those which use bags for sample collection, which are then analyzed at a time and place not necessarily related to the time and place of collection of the samples, and also those which are performed in real time, with the subject connected to the breath test instrument such that his breath is capable of being monitored almost continuously by the breath test instrument.

(c) Baseline Determination Methods

In the known prior art, the baseline is determined by determining the isotopic ratio in a single measurement taken from a single breath sample, or group of samples, obtained before the ingestion of the labeled substrate. This method may produce inaccurate results if the single baseline point obtained is incorrect, due either to drift or a high noise level in the instrument, or to physiological "noise" in the breaths supplied by the patient, when for some clinical reason, successive breaths give significantly different isotopic ratios.

In order to overcome these sources of potential inaccuracy, according to another preferred embodiment of the present invention, a baseline determining method is operative to review the quality of the measured baseline point, and if necessary, to measure one or more additional baseline points before the patient's ingestion of the labeled substrate.

According to a first additional preferred embodiment related to baseline measurement, if the self-diagnostic procedures operative within the instrument indicate that the quality of the point measured is high, such as is determined for instance, by the presence of a low standard deviation of scatter of the separate results making up that first baseline measurement point, or by the achievement of a carbon dioxide concentration close to the target value, then the control system concludes that a single baseline measurement is sufficiently accurate.

According to a further preferred embodiment, a second baseline measurement is taken. If the two measurements are within a predetermined value of each other, then it is assumed that no interference, neither instrumental nor physiological, was operative in the baseline measurement, and a simple mean of the two values is preferably used. If, on the other hand, discrepancy is detected between the two values, or one of the points is suspect as being of poor quality, as determined for instance, by the criteria given above, a number of possibilities present themselves. The point of poor quality can preferably be discarded and only the good point used in defining the baseline level. Alternatively and preferably, the system can request the measurement of a third baseline point. The result of this third baseline point preferably determines which of the results are used. If it is apparent that the first two values are scattered because of a noise problem, then the method takes a simple mean of all three values. Alternatively, if it is apparent from the third measurement that one of the first two values is severely discrepant from the other two, one of the first two values can be rejected as being delinquent.

According to further preferred embodiments of the present invention, the baseline measurements are performed in such a manner as to speed up the progress of the test. Thus, for instance, the second point can preferably be collected before completion of the analysis of the first point. If it becomes clear before completion of the measurement of point number 2, that point number 1 is of poor quality and cannot be used, then the calculation routine requests the collection of a third baseline sample, before completion of the measurement of point No. 2.

According to a further preferred embodiment of the present invention, in order to speed the test up even more, the patient is given the labeled substrate to ingest even before the results of the second measurement is known, but after the collection of the breath sample for the second baseline measurement. In this case, if a check of the quality of the measurement, as determined for instance by the standard deviation of the separate points making up the measurement, or by the accuracy of the achieved $CO_2$ target concentration, reveals that one of the measurements is likely to be of poor accuracy, then that measurement can be discarded in the calculation of the baseline. If both are of good quality, then their average may be used.

(d) Threshold Utilization Methods

A breath test for the detection of a specific clinical state, in common with many other diagnostic tests, relies on the attainment of a specific result or level as the indication of a positive result of the test. The provision of a definitive diagnosis about the absence of the sought-after clinical state, or, in other words, the definition of a negative result, is a much more difficult task. The operational function in a breath test is to determine when a change in the isotopic ratio of a component of breath samples of the subject is clinically significant with respect to the effect being sought. The criterion for this determination, as used in much of the prior art, is whether or not the DoB has exceeded a predefined threshold level, at, or within the allotted time for the test. When the result is positive, the decision is simpler, even though some doubt may still remain when the threshold crossing is not decisive, such as when a slow upward drift of the DoB value is obtained. When, however, the DoB hovers between the baseline and the threshold, with random noise perhaps sending it over the threshold occasionally, it becomes a much more difficult task to make a definite diagnosis that the result is really negative. The interpretation of negative results is of special importance in the commonly used urea breath test for detecting the presence of *H. pylori* in the upper GI tract, because of the widespread prevalence of ulcers and similarly related conditions of the upper GI tract in a significant proportion of the population.

One solution to this problem is to allow the test to continue for a longer time, to determine whether the result does or does not remain negative. This, however, involves patient inconvenience and the unnecessary occupation of expensive instrumentation, which could otherwise be used for the testing of further patients. It is therefore important to devise a means of defining the optimum breath test threshold level which enables definite results to be obtained, and especially negative results, in a minimum of time.

In order to accomplish this objective, and to achieve the highest sensitivity and specificity in the shortest possible measurement time, the breath test analyzer according to another preferred embodiment of the present invention, does not use fixed criteria for determining whether the change in the isotopic ratio of a patient's breath is clinically significant. Instead, the criterion is varied during the course of the test, according to a number of factors operating during the test, including, for instance, the elapsed time of the test, the noise level of the instrument performing the test, and the physiological results of the test.

Furthermore, although the traditionally used measurement of the change in the isotopic ratio has been the level of the ratio over a baseline level, according to other preferred embodiments of the present invention, the measurement could be the change over a previous measurement point other than a baseline level, or the rate of change of the isotopic level, or any other property which can be used to plot the course of the change.

In order to illustrate these novel measurement methods, a preferred embodiment of the present invention is now presented in which a threshold utilization method uses the real time results of the test to determine whether enough data has been accumulated in order to decide that the test is complete. This is accomplished by using a dynamic threshold level, whose value can be changed by the threshold utilization method during the course of a measurement, as a function of one or more of the following quantities:

(i) as a function of the nature of the data accumulated, i.e. whether the test is giving a well-defined result or not, (ii) as a function of the level and trends of the results obtained, (iii) as a function of the standard deviation of the accumulated data, and (iv) as a function of the noise and drift level in the particular instrument being used at that particular time.

In addition, according to a further preferred embodiment, two thresholds may be utilized, an upper and a lower threshold, which converge as the significance of the data collected becomes clearer.

A distinction can be made between a method of determining the use of variable thresholds at the beginning of a test, after the subsidence of oral activity, and as the test proceeds. During the early period of a test, before the accumulation of a large quantity of data, in order for a definitive result to be decided, the points must fall either very definitely above the baseline, which implies a positive result, or must be very close to the baseline, which implies a negative result. As the test proceeds, and the physiological result of a large number of accumulated points of measurement are taken into account, then the threshold criteria to be used should be more statistically based on the data accumulated.

Figure 25:
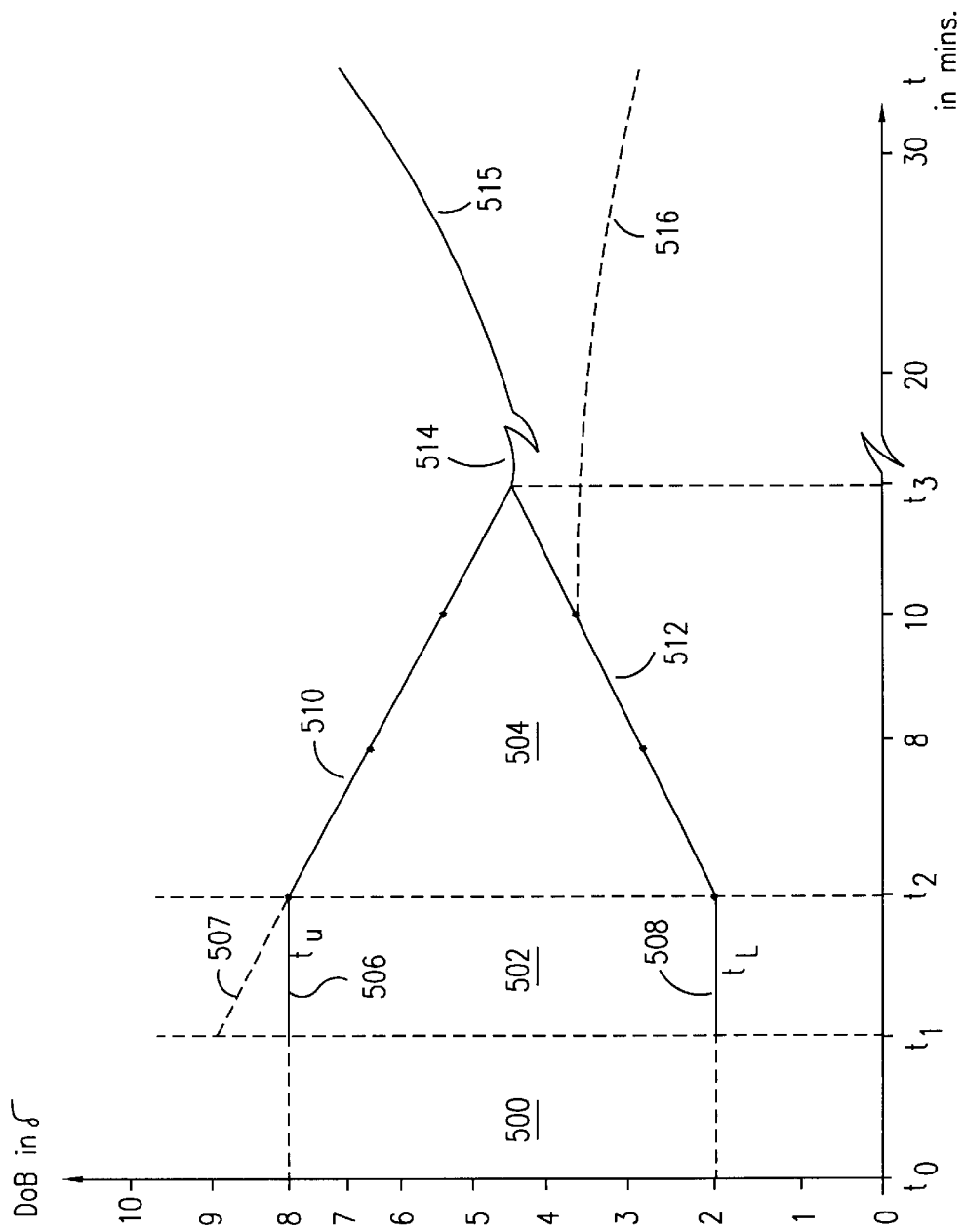
FIG. 25 is a graphic plot of the threshold values used for determining when the change in isotopic ratio can be considered as providing a definitive result, as a function of the time elapsed from ingestion of the isotope labeled substrate.

The result of these two approaches is shown by reference to FIG. 25, which illustrates a preferred method of the use of double and dynamic threshold criteria. In FIG. 25 is shown a plot of the threshold values used as a function of the time elapsed from ingestion of the isotope labeled substrate at time $t_0$. In the region 500 from the beginning of the test at time $t_0$, up to time $t_1$, breath samples are generally not taken into account in determining whether the upper threshold has been reached because of the possible existence of oral activity arising from the breakdown of the substrate by bacteria present in the patient's mouth. If, on the other hand, the oral activity detection system determines that no significant oral activity is present, then rising results may be taken into account in determining when the upper threshold has been crossed, even from time $t_0$. Results close to the baseline may generally always be taken into account, since they are obviously unaffected by the presence of oral activity, if any.

After the elapse of time $t_1$, when oral activity, if any, has subsided and all of the breaths collected are taken into account for calculation of the test results, two threshold levels are used, an upper threshold $T_u$ 506, and a lower threshold $T_l$ 508. Throughout the whole of the region 502, when very little data has been accumulated, widely different values of $T_u$ and $T_l$ are used, 8δ and 2δ in the preferred embodiment shown in FIG. 25. A result below 2δ is regarded as a negative result, while one above 8δ is regarded as a positive result. Results falling within the region between $T_u$ and $T_l$ are indefinite and require the accumulation of more data. According to further preferred embodiments, the threshold levels need not be constant in this region, but could commence widely apart at time $t_1$, and slowly converge with time, as shown by the alternative upper threshold curve 507.

An important aspect of this embodiment is that already by the time $t_1$ has been reached, which could be as little as 4 minutes from the ingestion of the urea, it is possible to make a definite positive or negative diagnosis, if the results obtained are sufficiently deviant from the expected baseline, 8δ and 2δ in the preferred embodiment described. A preferred criterion for a definite diagnosis is that if two points are obtained above the upper threshold, to the exclusion of any points below the lower threshold, then the diagnosis is positive. Similarly, the existence of two points below the lower threshold, to the exclusion of any points above the upper threshold, is a sufficient criterion to provide a negative diagnosis. A more stringent and preferred criterion for a negative diagnosis, bearing in mind the difficulties mentioned above in determining whether a result is truly negative, is the presence of any 3 or 4 successive points after the urea administration, falling either below the lower threshold or with an average below this threshold, and a standard deviation of less than 1δ and with a slope of less than 0.1δ per minute, and with no significant instrument drift or trend. Expressed qualitatively, this implies that for a measurement which shows the DoB plot to be fairly flat, and on an instrument known historically to be stable in operation, then a negative result can be determined sooner than by any prior art method. The speed with which a diagnosis can be provided thus distinguishes the breath test of the present invention from those of prior art instruments and methods, both for positive and for negative results After elapse of a time $t_2$, shown at 6 mins in the embodiment of FIG. 25, when a sufficient number of points have been accumulated, the standard deviation of the results should have dropped, and the physiological result of the test, if conclusive in either direction, should be evident enough that the thresholds may be closed up gradually, and even moved in the direction which provides the highest sensitivity and specificity for the test in progress. The time $t_2$ from which this threshold closure begins to operate, and the rate of closure itself of the thresholds 510, 512, and the rate of change of any level common to both of them, are determined by the data themselves, or are predetermined. Points with standard deviations which converge rapidly from the best-fit curve, result in speedy threshold closure and movement, and vice versa for slowly converging standard deviations. After a time $t_3$, which too is determined by the degree of scatter of the points, the two thresholds converge into one threshold 514, at the traditionally used level of 5δ in the embodiment shown, and from that time on, a diagnosis is made on the basis of the result falling above or below this threshold.

If, on the other hand, the data points remain scattered, and their average level close to 5δ, a fault message is displayed and the test concluded without a meaningful result.

In use, the threshold utilization method shown in FIG. 25 operates as follows. A subject with a rising DoB result who is not above 8δ after 6 minutes, is evaluated again after 8 minutes with a threshold of 7δ, and if not over this new threshold, again after 10 minutes with a 6δ threshold, until the traditional 5δ is reached. Likewise, a subject showing a non determined DoB trend, who is not below 2δ after 6 minutes is evaluated again after 8 minutes with a threshold of 3δ, and if not below this new threshold, again after 10 minutes with a 4δ threshold, until the traditional 5δ is reached.

As the time of the test proceeds, and the data accumulated more accurately reflects the physiological reality of the breath test mechanism, whereby the DoB of positive subjects rises as time proceeds, then according to a further preferred embodiment of the present invention, the threshold used 515 is allowed to rise slowly with the continuation of the test time.

According to yet another preferred embodiment, the lower threshold can remain independently existent instead of coalescing with the upper threshold to form a single threshold level. This is shown in FIG. 25 by alternative and preferable lower threshold 516, which either remains constant at a certain upper level, shown at 4δ in the example illustrated, or slowly falls with time, as the differentiation between a negative result and a positive result becomes more pronounced.

The validity of the use of variable thresholds according to the above preferred embodiments has been verified by comparisons of the results obtained with a breath tester incorporating such threshold embodiments, with results obtained by means of a monitoring test method. For the case of the *H. Pylori* breath test, such a standard monitoring method is by the endoscopic collection of a biopsy from the stomach of the patient, followed by a histological examination of the tissue, or a culture of the bacteria present.

According to a further preferred embodiment of the present invention, the threshold values used are made dependent on the self-diagnostic outputs of the system. For an instrument giving poor results, such as having a high noise level, or a systematic noise pattern, or a trend in the results, the threshold utilization method uses wide initial threshold values, namely a comparatively high upper threshold and a low lower threshold. For an instrument giving good results, such as having a low noise level or a low level of drift, the upper and the lower threshold levels and also the difference between them can all be lowered, and the number of points falling below the threshold required to define a negative result can then be decreased. In this way, it becomes possible to define a test result as being negative or positive earlier than with a fixed threshold.

According to a further preferred embodiment of the present invention, a threshold utilization method is used for determining whether sets of points measured can be considered to give a definitive test result. A best fit polynomial, preferably of second order, is constructed to functionally approximate the plot of the points obtained in one test. Only those points measured following the effective cessation of oral activity are used in the construction of this polynomial. A weighted standard deviation of those points from the calculated polynomial curve is then calculated. The weighting is performed such that for points less than, for example, 5δ above the baseline, the deviation from the polynomial curve is taken as is. For points of over 5δ above the baseline, since the effect of random noise on such a measurement is far less significant, the calculation method takes only 20% of the deviation of the point from the polynomial as the effective error value for the purpose of calculating the weighted standard deviation. If this weighted standard deviation is greater than 1.5σ, the measurement is regarded as problematic because of the high scatter of results.

In addition to the standard deviation criterion, there are other preferred criteria on the basis of which the measurement may be rejected as being inconclusive. An example of one such preferred criterion is for instance if at least 2 out of 5 points measured fall within the threshold limits, such as from 3δ to 7δ above the baseline, while at the same time, the last measured point is less than 10δ above baseline, indicating that there is no strongly positive result. Even though the final point alone would seem to indicate a positive result, the calculation routine rejects the measurement, as extant at that point in time, because of the uncertainty introduced by the previously mentioned "2 out of 5" criterion.

In some parts of this specification, the procedures and computational methods have been described in terms of the urea breath test for the detection of *Helicobacter Pylori* in the upper gastrointestinal tract. It is to be understood that this test is only an example of many diagnostic tests which can be performed by means of breath testing, and that the invention is not meant to be limited to the preferred explanatory examples brought from the *H. pylori* detection breath test.

Spectrally Stable Improved Infra-red Lamp Source

The spectral stability of the lamp source used in the gas analyzer of breath test instrumentation is of importance, because of the high resolution and selectivity required to accurately determine the concentration of one isotopic species in the presence of another. Lack of good spectral stability may cause small changes occurring in the source spectrum to be erroneously interpreted as intensity changes resulting from changes in isotopic concentration.

A number of factors affect the spectral stability of the electrode-less cold gas discharge infra-red lamp source, of the type used in the breath test instrumentation according to the present invention. These factors include temperature, electrode position and time. The first two are factors of the operating conditions and geometry of the lamp, and if well understood, can be well controlled. The third factor mentioned, namely change over time, is much more problematic, since such changes are due to long term changes in the composition of the gas fill. It is thought that a major cause for long term changes in the lamp output and spectrum is the result of the gradual break down of the IR-active molecule in the discharge. In the case of the carbon dioxide lamp, the carbon dioxide dissociates into carbon monoxide and oxygen. In the course of the first few minutes of lamp operation, an equilibrium of the above molecules is reached, but over a longer period of operation, this equilibrium level changes as CO and $O_2$ are adsorbed on the walls of the lamp envelope. Impurities also reduce the $CO_2$ level still further.

Up to now, the majority of the prior art on the subject of the changes with time in the operating conditions of electric discharges in carbon dioxide has been primarily concerned with the change in power output which occurs as the $CO_2$ level changes. This has been the main point of interest because of the importance of avoiding a decay over time in the power levels of $CO_2$ lasers, and especially of sealed-off $CO_2$ lasers.

However, in the case of discharge lamps, whose emitted radiation is a result of non-coherent, spontaneous emission from an excited state to the ground state, changes in $CO_2$ concentration also affect the emission spectrum by means of a process known as self-absorption. In $CO_2$ lasers, on the other hand, this phenomenon is, for all practical purposes, non-existent. The phenomenon of self-absorption operates in the following way. The $CO_2$ molecules in the lamp not only emit radiation when excited, but they also absorb radiation when in the ground state, by means of induced absorption. The lamp itself thus operates as an absorption cell to its own emitted light as this light passes through the lamp's own gas fill to the output window. The $CO_2$ lines are absorbed at their centers, and their shapes thus change by means of the process known as self-absorption.

The effect of self absorption on NDIR spectroscopy measurements can be significant. Even when Doppler broadened, the lines emitted from the lamp are much narrower than the absorbing lines in a gas sample at atmospheric pressure. As a result, the region of coincidence on the absorbing lines is of approximately constant magnitude. Hence, although there is no change in absorption characteristics for any individual emission line for different degrees of self-absorption, the change in the distribution of the individual line intensities does cause an overall change in the absorption characteristics. As a result, changes in self-absorption create a change in the emitted line strength distribution of the first order band group, i.e. the weaker absorbing lines of the Boltzman distributed intensities traverse the lamp with little attenuation, even in the presence of the high $CO_2$ concentrations inside the lamp, but the strongly absorbing lines of the Boltzman distributed intensities are strongly attenuated.

These changes in line intensity distribution are similar in their effect on the absorption characteristics to changes in distribution resulting from changes in relative group/order (isotope) strength, or Boltzman distribution changes resulting from changes in temperature.

Expressed mathematically, the lamp output radiation after absorption in the gas cell is given by:

$$I = \Sigma e^{-\alpha 1jdc}I_{1j} + \Sigma e^{-\alpha 2jdc}I_{2j}$$

where $I_1$ and $I_2$ are for the first and second order respectively, and are defined over their line intensities $I_{nj}$. This relationship follows from the well-known Beer-Lambert law.

Defining a distribution ratio $X = \Sigma I_{1j}/(\Sigma I_{1j} + \Sigma I_{2j})$, which is the output ratio between first and second order of line distribution j, the transmission $t_{(c)}$ is given by:

$$t_{(c)} = t_{1(c)}X + t_{2(c)}(1-X)$$

for any given concentration c.

When the lamp $CO_2$ concentration changes with time, this distribution ratio changes and hence, also the absorption characteristics of the complete optical system, consisting of the emitting lamp together with the absorbing cell. Under these conditions, it becomes difficult to distinguish such changes from the changes in gas concentration being measured.

Although self-absorption can be anticipated from theory, it is difficult to demonstrate directly. This is mainly because the typical line width of the lamp is less than 0.006 cm$^{-1}$. The only instrument currently available which is capable of resolving such a narrow width is an FTIR (Fourier transform infra-red) spectrometer, with a mirror movement of at least 2 meters. The self absorption fine structure is even more difficult to resolve.

Experiments have been performed to observe the effect in discharge lamps, by using an FTIR spectrometer with possibly one of the optimum resolutions currently attainable. Comparisons between aged and new lamps for changes in line shape clearly show the effect. Other effects such as changes in Boltzman distribution, or changes in the ratio of first and second order lines, are shown to be negligible in comparison.

It is well-known in the art that one method of encouraging the recombination of dissociation products of molecules broken down under the effect of electrical discharges, to reproduce the parent gas molecule from which they originally dissociated, is by the use of catalysts. In the case of the $CO_2$ discharge, the carbon monoxide and oxygen molecules within the lamp envelope can be recombined under the influence of suitable catalysts, to reform the $CO_2$ molecules from which they dissociated. In sealed-off laser $CO_2$ laser technology, such catalysts are widely used to maintain the level of $CO_2$ in the laser cavity, in order to prevent a decay in the laser power output which would occur if the percentage of dissociated $CO_2$ were to increase with time.

As mentioned above, the effect of self-absorption is effectively non-existent in $CO_2$ laser discharges, as also in other systems not lasing directly to the ground state. In the $CO_2$ laser, the stimulated emission of the laser light is produced by a decay transition from a metastable state down to a short-lived excited state. It is this transition which produces the familiar $CO_2$ 10.6 μm wavelength radiation. Since the lasing transition is not to the ground state, the large population of ground state molecules do not absorb the lasing transition energy, and for this reason, self-absorption is effectively non-existent in such laser discharges.

In gas discharge lamps of the type disclosed in U.S. Pat. No. 5,300,839, on the other hand, the IR radiation is created by spontaneous emission in the wavelength region of 4.3 μm, by transition of the IR active molecules from rotational-vibrational excited states, directly to the ground state. No metastable states are involved in this transition scheme. Since a high proportion of the $CO_2$ molecules populate the ground level, the spontaneous radiation associated with the transition to this ground level is readily absorbed by these ground state molecules, by the process of induced absorption. This results in appreciable self-absorption of the radiation. In this respect, discharge lamps are significantly different from the stimulated emission of laser discharges operating in the same molecular system, in that they show a significant self absorption effect.

The previously known catalyst technology used in laser discharges is aimed exclusively at maintaining the laser gain, the laser efficiency and the power output level of the emission from the laser. To the best of the Applicants' knowledge, no mention has been made or suggested, that such catalysts be used to maintain the spectral stability of the discharge, since the mechanism of self-absorption by which this could be performed, is not applicable to lasers. Furthermore, to the best of the Applicants' knowledge, catalysts have never been used, or their use suggested for stabilizing the emission spectra of gas discharge lamps.

There is thus provided, in accordance with a preferred embodiment of the present invention, a method for increasing the spectral stability of cold gas discharge infra-red lamp sources, by the use of a catalyst to reduce the changes with time in the concentration of excited gas molecules in the lamp active in emitting to ground state levels, thereby resulting in a reduction in the changes in self-absorption.

A number of catalysts are known for reproducing $CO_2$ from CO and $O_2$, such as platinum with tin oxide, sputtered gold and silver coatings. The method of providing the catalytic coating on the interior of the discharge lamp envelope, in order to increase the lamp's spectral stability, depends on the material used for the catalyst. According to one preferred embodiment of the present invention, the method consists of sputtering the gold in a finely divided form onto the inside of the lamp envelope, such that it forms a non-conducting film, with a very high surface to volume ratio. Other metals such as Iridium, Rhodium, Palladium and Nickel can also be used as catalysts. Other methods of applying the catalyst besides sputtering may also be used, such as chemical or vapor deposition.

Figure 26:
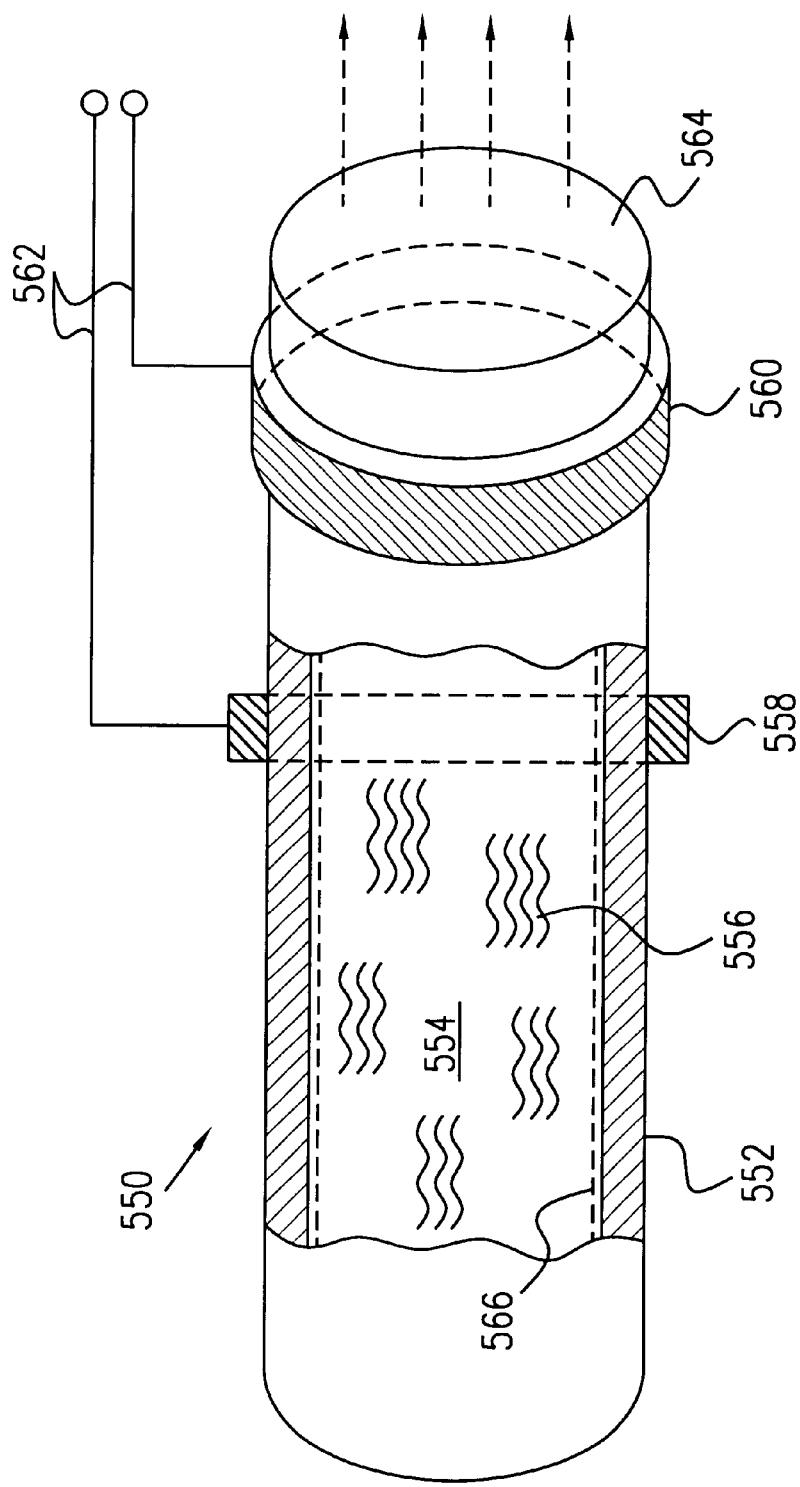
FIG. 26 is a schematic drawing of an improved electrically-excited gas discharge lamp, constructed and operative according to another preferred embodiment of the present invention.

Reference is now made to FIG. 26, which is a schematic drawing of an improved electrically-excited gas discharge lamp 550, constructed and operative according to another preferred embodiment of the present invention. The basic elements of the lamp construction are similar to those disclosed in U.S. Pat. No. 5,300,859. The envelope 552 of the lamp defines an internal volume 554 which contains a gaseous mixture 556 including one or more IR-active gaseous species. The gas is preferably excited by two electrodes 558, 560, disposed outside of the envelope, and supplied with RF-exciting power via a pair of cables 562. After being raised to an excited state, the IR-active gaseous species decays by means of a spontaneous emission directly to the ground state, and the emitted radiation is output by means of an optically transparent window 564 at one end of the lamp envelope. According to this preferred embodiment of the present invention, on the inner wall of the lamp envelope is a layer of catalyst 566, operative to maintain a constant level of the dissociation products of the IR-active gaseous species, such that the self absorption of the emitted radiation is kept at a constant level, and spectral stability of the lamp output maintained, as explained in detail hereinabove.

The catalyst is chosen to ensure an equilibrium between the IR-active gaseous species and its dissociation products. In this respect, it should be noted that unlike prior art use of catalysts in lasers, where the catalyst is optimally operative to keep dissociation of the IR-active species to a minimum, in order to keep laser output power to a maximum, according to the present invention, the catalyst need only maintain a constant equilibrium level of the IR-active species in order to achieve its aim of maintaining constant self-absorption and hence constant spectral stability. The catalyst may be applied by any of the methods known in the art, by chemical, sputtered or vapor deposition, or by any other suitable means. The catalyst may be of any of the types mentioned hereinabove.

Since the catalyst reduces the breakdown of $CO_2$, it is possible to reduce the need for a large ballast volume of gas, and thus to produce a lamp of considerably reduced size. Such a lamp is advantageous for use in portable systems. Such a smaller lamp has a better surface to volume ratio with respect to the active media and the activated $O_2$ molecules require a shorter path length to reach the coating, and hence have a higher probability of reaching the catalytic coating in the required activated state. In U.S. Pat. No. 5,300,859, lamp volumes of the order of 60 ml. are disclosed. This volume was required to ensure an adequate reservoir volume to ensure long lamp life. If lamps of smaller volume were used, the increased effect of the absorption of dissociated carbon monoxide and oxygen on the increased surface of the walls in relation to the gas volume, would result in the lamp discharge decaying very rapidly. The use of a catalyst on the lamp walls, according to a further embodiment of the present invention, allows significantly smaller lamps to be constructed, without negatively affecting their lifetime or spectral stability. It is possible to achieve lamp volumes of 6 ml or less, which provide similar lifetimes to those of the prior art 60 ml volume lamps, while maintaining the same level of spectral stability. This is of significant advantage for use in the breath tester, where two lamp sources are typically required, whose mutual stability is dependent on the maintenance of both of them under similar environmental conditions, something that is simpler to achieve with more compact lamps.

Since the catalyst reduces the breakdown of $CO_2$, the use of a catalyst according to the present invention, makes it feasible to produce a lamp with a lower $CO_2$ pressure. In U.S. Pat. No. 5,300,859, $CO_2$ percentages of the order of 10% are recommended for optimum output and lifetime considerations. According to preferred embodiments of the present invention, the use of a catalyst allows the operation of the lamp with lower $CO_2$ concentrations in the lamp gas mixture, down to 5%. This results in lower self-absorption effects, with consequent higher intensity central lines of the absorption spectrum, as explained hereinabove. This provides very deep absorption curves with a high extinction ratio in the gas analyzer measurement cell, permitting use of a shorter cell path and a more compact instrument without losing detection sensitivity or selectivity. This is of high importance when measuring the very low concentration levels of the minority isotopic component in a breath test.

It will be appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A method of performing a breath test, comprising the steps of:
    using a predetermined criterion for determining when a change in a measurement of an isotopic ratio of at least one breath sample of a subject is clinically significant; and allowing said criterion to change during said breath test.

2. The method according to claim 1 and wherein said change in said measurement comprises the deviation of said isotopic ratio from a measurement of at least one previous sample of said subject.

3. The method according to claim 2 and wherein said measurement of at least one previous sample of said subject is a baseline measurement.

4. The method according to claim 1 and wherein said change in said measurement comprises the rate of change of said isotopic ratio.

5. The method according to claim 1 and wherein said criterion is a function of the elapsed time of the test.

6. The method according to claim 1 and wherein said criterion is a function of the noise level of the instrument performing said test.

7. The method according to claim 1 and wherein said criterion is a function of the physiological results of said test.

8. A breath test method, comprising the steps of:
    performing a first measurement of the isotopic ratio of at least a first breath sample of a subject;
    performing a second measurement of the isotopic ratio of at least a second breath sample of said subject; and
    determining when said second measurement shows sufficient deviation from said first measurement that a clinically significant result of the breath test may be concluded;
    wherein the level of said sufficient deviation is allowed to undergo variation during said breath test.

9. The method according to claim 8 and wherein said first measurement of the isotopic ratio of at least a first breath sample of said subject is a baseline measurement.

10. The method according to claim 8 and wherein said level of sufficient deviation is at least a function of the elapsed time from ingestion of an identifying substrate by a subject.

11. The method according to claim 8 and wherein said level of sufficient deviation is at least a function of the physiological results of the analysis of at least one of said samples.

12. The method according to claim 8 and wherein said level of sufficient deviation is at least a function of the nature of the results obtained in said breath test.

13. The method according to claim 12 and wherein said nature of the results is at least a function of the standard deviation of the spread of results in said breath test.

14. The method according to claim 12 and wherein said nature of the results is at least a function of the noise level present in said results.

15. The method according to claim 12 and wherein said nature of the results is at least a function of the instrumental drift present in said results.

16. The method according to claim 8 and wherein said level of sufficient deviation covers a range of values between an upper threshold and a lower threshold.

17. The method according to claim 16 and wherein said upper threshold and said lower threshold converge as the test proceeds.

18. The method according to claim 8 and wherein said first measurement of the isotopic ratio of at least a first breath sample of a subject is performed only after significant subsidence of oral activity.

19. The method according to claim 16 and wherein the presence of at least two measurements above said upper threshold within a predetermined time is indicative of a positive result of said breath test.

20. The method according to claim 16 and wherein the presence of at least two successive measurements above said upper threshold is indicative of a positive result of said breath test.

21. The method according to claim 16 and wherein the presence of at least two measurements above said upper threshold in combination with the absence of measurements below said lower threshold is indicative of a positive result of said breath test.

22. The method according to claim 16 and wherein the presence of at least two measurements below said lower threshold within a predetermined time is indicative of a negative result of said breath test.

23. The method according to claim 16 and wherein the presence of at least two successive measurements below said lower threshold is indicative of a negative result of said breath test.

24. The method according to claim 16 and wherein the presence of at least two measurements below said lower threshold in combination with the absence of any measurements above said upper threshold is indicative of a negative result of said breath test.

25. The method according to claim 16 and wherein the presence of at least two successive measurements falling below the upper threshold, with less than a predetermined difference in the value of delta between said three measurements, and with less than a predetermined average slope between them, is indicative of a negative result of said breath test.

26. The method according to claim 16 and wherein the presence of at least two successive measurements falling below the lower threshold, with less than a predetermined average slope between them, is indicative of a negative result of said breath test.

27. A breath test method for determining the presence of a clinically significant state in a subject, comprising the steps of:
    performing measurements of the changes from a baseline of an isotopic ratio in a plurality of samples of exhaled breath of said subject, following the effective cessation of oral activity; determining a polynomial which approximates the functional plot of said measurements with time;
    calculating a weighted standard deviation of said measurements from said polynomial, wherein for measurements over said baseline by more than a predetermined amount, a predefined fractional part of the measurement is taken, while for measurements not over said baseline by more than said predetermined amount, the measurement is taken in its entirety; and determining whether said weighted standard deviation exceeds a predetermined level.

28. A breath test method comprising the steps of:

performing a measurement of the isotopic ratio of at least a first breath sample of a subject; and determining when said measurement shows sufficient deviation from a baseline measurement that a clinically significant result of the breath test may be concluded;

wherein said deviation comprises an upper and a lower threshold band of uncertainty, and wherein the extent of this band is dependent on at least one of the parameters selected from the group consisting of the elapsed time of said breath test, the standard deviation of the physiological spread of results, the dynamics of the physiological change in isotopic ratio, the number of points measured in the breath test, the environmental conditions present during the breath test, and the noise and/or drift levels of the instrument executing the breath test.

29. A method for determining the reliability of a breath test, comprising the steps of:

obtaining results from said breath test;

defining a reliability parameter by combining at least one of the criteria selected from the group consisting of the instrument noise and/or drift level, the standard deviation of the physiological spread of results, the dynamics of the physiological change in isotopic ratio, and the time elapsed since ingestion of a labeled substrate; and using said reliability parameter to assess the results of said breath test according to a predetermined reliability criterion.

30. The method according to claim 29 and wherein said reliability parameter is taken into account in determining when a clinically significant result has been obtained in said breath test, in order to terminate said test.

31. The method according to claim 29 and wherein said reliability parameter is output with the result of the breath test.

32. A breath test instrument comprising:

tubing for collecting breath from a subject; and a gas analyzer for determining isotopic ratio in said gas;

wherein said gas analyzer monitors changes in an isotopic ratio of a gas in exhaled breath samples of said subject virtually continuously, and determines that said test has a clinically significant outcome in accordance with the ongoing results of said test.

33. A breath test instrument according to claim 32, further comprising a signal for indication that a clinically significant outcome of a breath test has been determined.

34. A breath test instrument according to claim 33, and wherein said signal is a visible signal.

35. A breath rest instrument according to claim 33, and wherein said signal is an audible signal.

36. A breath test instrument according to claim 35, and wherein said signal also indicates the nature of the clinically significant outcome of said breath test.

37. A breath test instrument according to claim 32, such that the outcome of said test is substantially independent of dynamic physiological effects occurring in said subject as a result of background conditions.

38. A breath test instrument according to claim 37, and wherein said background conditions are the result of treatment with a drug therapy.

39. A breath test instrument according to claim 37, and wherein said background conditions are the result of food intake in a period prior to the performance of the breath test.

40. A breath instrument according to claim 39, and wherein the need for a pre-test fast by the subject is obviated.

41. A breath test instrument according to claim 32, and wherein the outcome of said test on said subject undergoing treatment with a gastro-intestinal drug therapy, is obtained more reliably than using corresponding breath tests which do not monitor said changes in an isotopic ratio substantially continuously.

42. A breath test instrument according to claim 32, and wherein the outcome of said test is obtained more reliably than would be obtained by corresponding breath test instruments which do not monitor said changes in an isotopic ratio substantially continuously.

43. A breath test instrument according to claim 32, and in which said outcome of said test is obtained sooner than would be obtained by corresponding breath test instruments which do not monitor said changes in an isotopic ratio substantially continuously.

44. A breath test instrument according to claim 32, and in which said ongoing results of said test enable a positive result to be determined even when said isotopic ratio does not clearly exceed a predetermined threshold level.

45. A breath test instrument according to claim 32, and in which said ongoing results of said test enable a negative result to be determined even when said isotopic ratio exceeds a predetermined threshold level.

46. A breath test instrument according to claim 45, and in which said negative result is determined even when said isotopic ratio exceeds said predetermined threshold level because of instrumental drift.

47. A breath test instrument according to claim 32, and in which said ongoing results of said test enable a negative result to be determine by the detection of correlation between said isotopic ratio and instrumental drift.

* * * * *

UNITED STATES PATENT AND TRADEMARK OFFICE
CERTIFICATE OF CORRECTION

PATENT NO. : 6,656,127 B1
DATED : December 2, 2003
INVENTOR(S) : Ben-Oren et al.

It is certified that error appears in the above-identified patent and that said Letters Patent is hereby corrected as shown below:

<u>Title page,</u>
Item [75], Inventors, please delete "Boaz Givron" and insert -- Boaz Giron -- therefor.

Signed and Sealed this

Eighteenth Day of January, 2005

JON W. DUDAS
*Director of the United States Patent and Trademark Office*